United States Patent
Yates et al.

(10) Patent No.: US 11,710,317 B2
(45) Date of Patent: Jul. 25, 2023

(54) SYSTEMS, METHODS, AND COMPUTER-PROGRAM PRODUCTS FOR ASSESSING ATHLETIC ABILITY AND GENERATING PERFORMANCE DATA

(71) Applicant: Recruiting Analytics LLC, Atlanta, GA (US)

(72) Inventors: Corey Leon Yates, Roswell, GA (US); Alfonzo Thurman, II, Snellville, GA (US)

(73) Assignee: Recruiting Analytics LLC, Atlanta, GA (US)

( * ) Notice: Subject to any disclaimer, the term of this patent is extended or adjusted under 35 U.S.C. 154(b) by 308 days.

(21) Appl. No.: 17/002,331

(22) Filed: Aug. 25, 2020

(65) Prior Publication Data

US 2021/0275059 A1    Sep. 9, 2021

Related U.S. Application Data

(60) Provisional application No. 63/011,976, filed on Apr. 17, 2020, provisional application No. 62/987,809, (Continued)

(51) Int. Cl.
*A61B 5/11* (2006.01)
*A63B 24/00* (2006.01)
(Continued)

(52) U.S. Cl.
CPC .......... *G06V 20/42* (2022.01); *A61B 5/117* (2013.01); *A61B 5/1118* (2013.01); (Continued)

(58) Field of Classification Search
CPC .......... A61B 5/1128; A61B 2503/10; A63B 24/0003; A63B 24/0021; A63B 24/0062; (Continued)

(56) References Cited

U.S. PATENT DOCUMENTS 6,710,713 B1 * 3/2004 Russo ............... A63B 24/0021
                                                     348/157
9,486,693 B2 * 11/2016 Regan ............... A63B 71/0616
(Continued)

FOREIGN PATENT DOCUMENTS

KR    20180063777 A  *  6/2018    ............. A63B 71/06

OTHER PUBLICATIONS

Sanford, R., Gorji, S., Hafemann, L. G., Pourbabaee, B., & Javan, M. (2020). Group Activity Detection from Trajectory and Video Data in Soccer. In Proceedings of the IEEE/CVF Conference on Computer Vision and Pattern Recognition Workshops (pp. 898-899).

(Continued)

*Primary Examiner* — Christle I Marshall
(74) *Attorney, Agent, or Firm* — Shook, Hardy & Bacon L.L.P.

(57) ABSTRACT

Methods, systems, and computer-program products used for assessing athletic ability and generating performance data. In one embodiment, athlete performance data is generated through computer-vision analysis of video of an athletic performing, e.g., during practice or gameplay. The generated performance data for the athlete may include, for example, maximum speed, maximum acceleration, time to maximum speed, transition time (e.g., time to change direction), closing speed (e.g., time to close the distance to another athlete), average separation (e.g., between the athlete and another athlete), play-making ability, athleticism (e.g., a weighted computation and/or combination of multiple metrics), and/or other performance data. This performance data may be used to generate and/or update a profile associated with the athlete, which can be utilized for recruiting, scouting, comparing, and/or assessing athletes with greater efficiency and precision.

20 Claims, 48 Drawing Sheets

Related U.S. Application Data filed on Mar. 10, 2020, provisional application No. 62/985,316, filed on Mar. 4, 2020.

(51) Int. Cl.
| | |
|---|---|
| *G06V 20/40* | (2022.01) |
| *G06V 40/20* | (2022.01) |
| *A61B 5/117* | (2016.01) |
| *G06T 7/246* | (2017.01) |

(52) U.S. Cl.
CPC ........ *A61B 5/1128* (2013.01); *A63B 24/0003* (2013.01); *A63B 24/0021* (2013.01); *A63B 24/0062* (2013.01); *G06T 7/248* (2017.01); *G06V 40/25* (2022.01); *A61B 2503/10* (2013.01); *G06T 2207/30221* (2013.01)

(58) Field of Classification Search
CPC ........ G06V 20/42; G06V 40/25; G06V 20/52; G06V 40/23; G06T 2207/30221
See application file for complete search history.

(56) References Cited

U.S. PATENT DOCUMENTS

| | | | |
|---|---|---|---|
| 9,824,281 B2 | 11/2017 | Roshtkhari et al. | |
| 9,977,966 B2* | 5/2018 | Zakaluk | G06T 7/73 |
| 10,402,655 B2 | 9/2019 | Roshtkhari et al. | |
| 10,430,953 B2 | 10/2019 | Roshtkhari et al. | |
| 11,157,742 B2* | 10/2021 | Zhang | G06N 3/08 |
| 2006/0132487 A1* | 6/2006 | Sada | G06T 7/20 |
| | | | 345/427 |
| 2011/0013836 A1* | 1/2011 | Gefen | G06T 7/248 |
| | | | 382/171 |
| 2017/0109015 A1* | 4/2017 | Krasadakis | G06F 16/335 |
| 2018/0336704 A1 | 11/2018 | Roshtkhari et al. | |
| 2019/0091541 A1 | 3/2019 | Schulte et al. | |
| 2019/0251366 A1 | 8/2019 | Zhong et al. | |

OTHER PUBLICATIONS

Gavrilyuk, K., Sanford, R., Javan, M., & Snoek, C. G. (2020). Actor-transformers for group activity recognition. In Proceedings of the IEEE/CVF Conference on Computer Vision and Pattern Recognition (pp. 839-848).

Mehrasa, N., Zhong, Y., Tung, F., Bornn, L., & Mori, G. (2017). Learning person trajectory representations for team activity analysis. arXiv preprint arXiv:1706.00893.

Zhai, M., Chen, L., Mori, G., & Javan Roshtkhari, M. (2018). Deep learning of appearance models for online object tracking. In Proceedings of the European Conference on Computer Vision (ECCV) (pp. 0-0).

Zhong, Y., Xu, B., Zhou, G. T., Bornn, L., & Mori, G. (2018). Time perception machine: Temporal point processes for the when, where and what of activity prediction. arXiv preprint arXiv:1808.04063.

Liu, G., & Schulte, O. (2018). Deep reinforcement learning in ice hockey for context-aware player evaluation. arXiv preprint arXiv:1805.11088.

Schulte, O., Khademi, M., Gholami, S., Zhao, Z., Javan, M., & Desaulniers, P. (2017). A Markov Game model for valuing actions, locations, and team performance in ice hockey. Data Mining and Knowledge Discovery, 31(6), 1735-1757.

Schulte, O., Zhao, Z., Javan, M., & Desaulniers, P. (Mar. 2017). Apples-to-apples: Clustering and ranking NHL players using location information and scoring impact. In Proceedings of the MIT Sloan Sports Analytics Conference.

Silva, R. M., Davis, J., & Swartz, T. B. (2018). The evaluation of pace of play in hockey. Journal of Sports Analytics, 4(2), 145-151.

Homayounfar, N., Fidler, S., & Urtasun, R. (2017). Sports field localization via deep structured models. In Proceedings of the IEEE Conference on Computer Vision and Pattern Recognition (pp. 5212-5220).

Fani, M., Neher, H., Clausi, D. A., Wong, A., & Zelek, J. (2017). Hockey action recognition via integrated stacked hourglass network. In Proceedings of the IEEE Conference on Computer Vision and Pattern Recognition Workshops (pp. 29-37).

Roy Tora, M., Chen, J., & Little, J. J. (2017). Classification of Puck Possession Events in Ice Hockey. In Proceedings of the IEEE Conference on Computer Vision and Pattern Recognition Workshops (pp. 91-98).

Khodabandeh, M., Vahdat, A., Zhou, G. T., Hajimirsadeghi, H., Javan Roshtkhari, M., Mori, G., & Se, S. (2015). Discovering human interactions in videos with limited data labeling. In Proceedings of the IEEE conference on computer vision and pattern recognition workshops (pp. 9-18).

Deng, Z., Zhai, M., Chen, L., Liu, Y., Muralidharan, S., Roshtkhari, M. J., & Mori, G. (2015). Deep structured models for group activity recognition. arXiv preprint arXiv:1506.04191.

Horton, M. (2020). Learning feature representations from football tracking. MIT Sloan Sports Analytics Conference.

Keane, E., Desaulniers, P., Bornn, L., & Javan, M. (2019). Data-driven lowlight and highlight reel creation based on explainable temporal game models. MIT Sloan Sports Analytics Conference.

Yu, D., Boucher, C., Bornn, L., & Javan, M. (2019). Playing Fast Not Loose: Evaluating team-level pace of play in ice hockey using spatio-temporal possession data. arXiv preprint arXiv:1902.02020.

Czuzoj-Shulman, N., Yu, D., Boucher, C., Bornn, L., & Javan, M. (2019). Winning Is Not Everything: A contextual analysis of hockey face-offs. arXiv preprint arXiv:1902.02397.

Roshtkhari, M. J., & Levine, M. D. (2016). Chapter 2.3: Tracking Without Appearance Descriptors. Abstract. In Handbook of Pattern Recognition and Computer Vision (pp. 239-254).

\* cited by examiner

Scheme of transition time calculation

Selecting correct data and dropping off the outliers

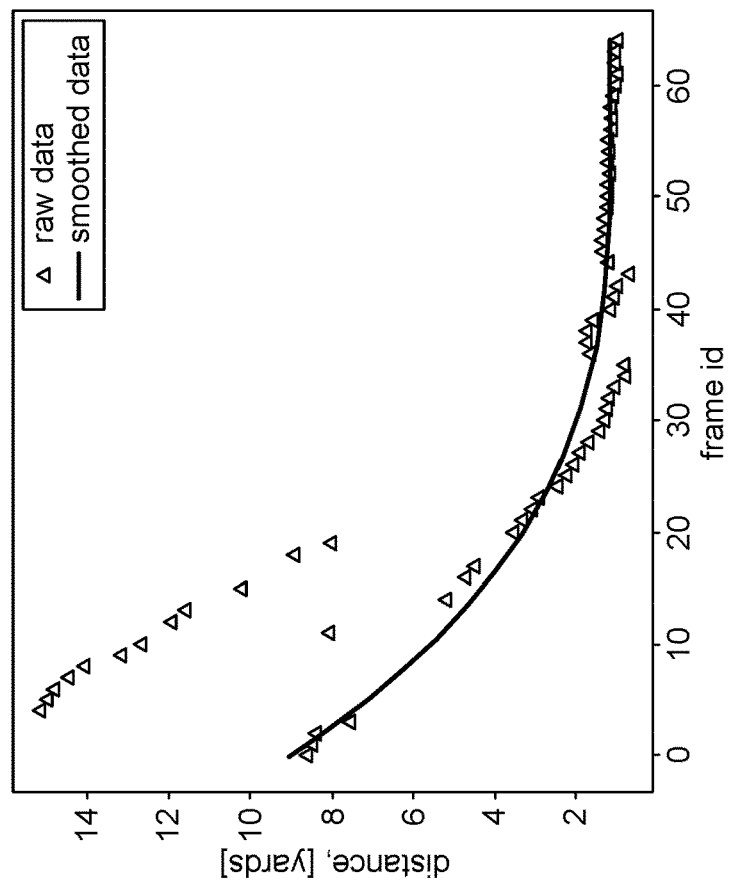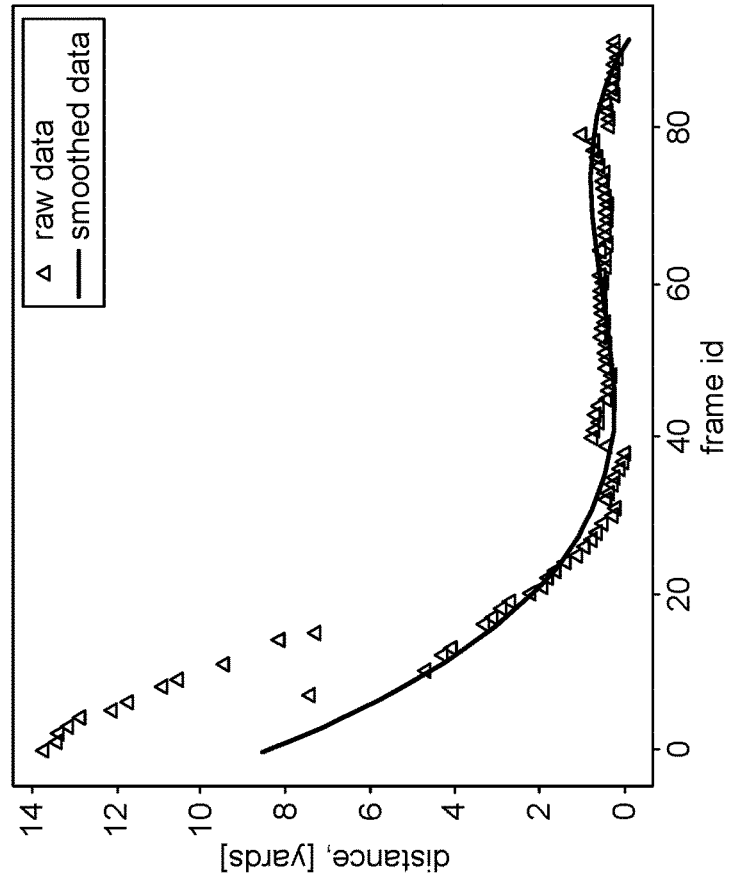
FIG. 22
Examples of distance smoothing

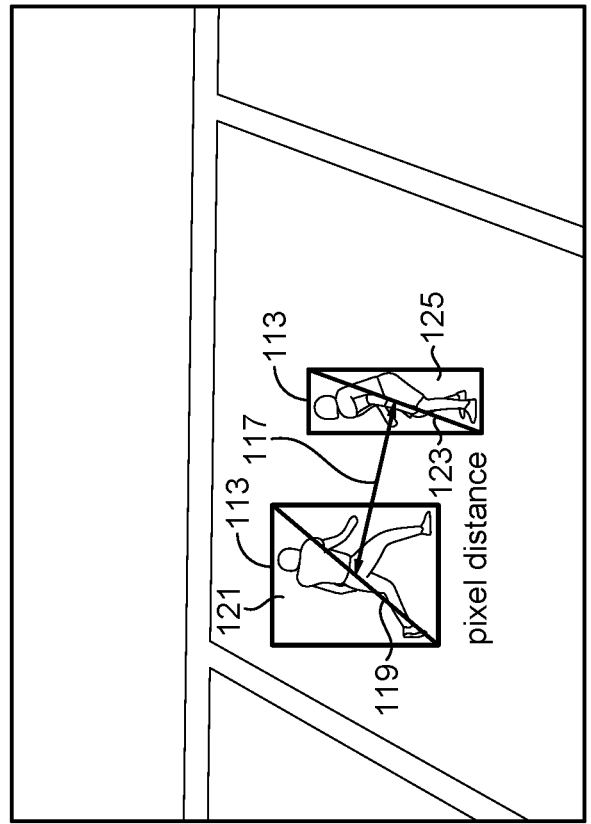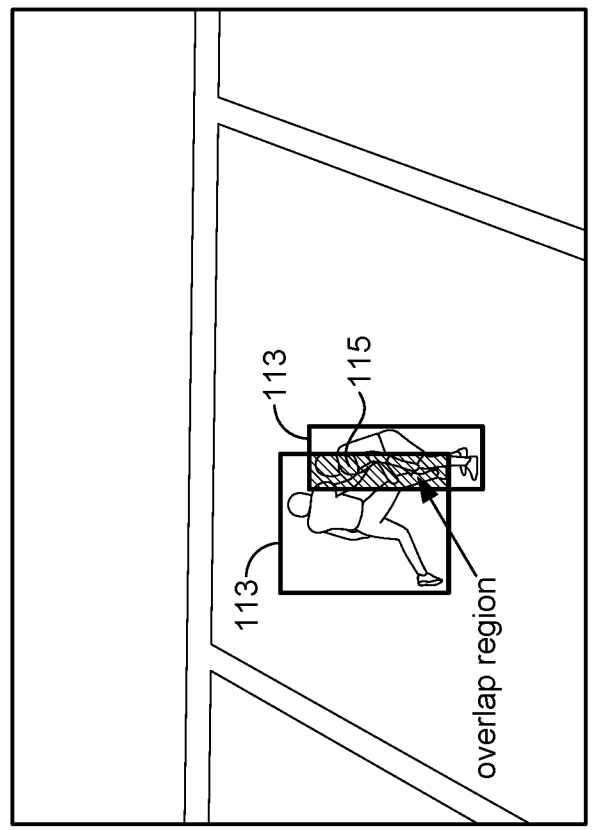
FIG. 23

Home   Fit Finder   My Board   Reports   ⓐ My Account ⌄

Welcome, Horace. Let's Get Started...

MY PROSPECTS
Go to My Board to view the imported Prospects that match athletes in our database.

[ View My Board ]

CREATE A REPORT
Create a Report and really see how your Prospects stack up amongst their peers.

[ Create A Report ]

DISCOVER NEW PROSPECTS
Discover new Prospects & find the right one for your program in Fit Finder.

[ Go to Fit Finder ]

Activity for Today, August 12, 2019

Social Engagement    Top Prospects

Top Prospects by:    Classification [Choose... ⌄]    Position [Choose... ⌄]

Film Grade Score ⓘ  Playmaking Ability ⓘ  Athleticism Score ⓘ  Last Name ⓘ
[Select... ⌄]       [Select... ⌄]         [Select... ⌄]        [Select... ⌄]

1. Jacob Matthews
Jacob Matthews '22
6'4 250 | Linebacker
Atlanta, Georgia
⚭ 83%  77%  96%
Offers Film Athleticism Playmaking
View Profile > | + My Watchlist | + My Board

2. Elliot Bauers
Joshua Walker
6'4 250 | Linebacker
Atlanta, Georgia
⚭ 61%  77%  96%
Offers Film Athleticism Playmaking
View Profile > | + My Watchlist | ★ My Board

3. Horace D. Williams
Jacob Matthews '22
6'4 250 | Linebacker
Atlanta, Georgia
⚭ 83%  77%  96%
Offers Film Athleticism Playmaking
View Profile > | + My Watchlist | + My Board

4. Alfonso Cory
Jacob Matthews '22
6'4 250 | Linebacker
Atlanta, Georgia
⚭ 83%  77%  96%
Offers Film Athleticism Playmaking
View Profile > | + My Watchlist | + My Board

5. Mario Morris
Jacob Matthews '22
6'4 250 | Linebacker
Atlanta, Georgia
⚭ 83%  77%  96%
Offers Film Athleticism Playmaking
View Profile > | + My Watchlist | + My Board Create Dashboards using your own Prospects.
[ Go to Fit Finder ]

UnderCruited
Discover talent before anyone else even begins to see potential. Make your next play, your best play.

Learn More

3 NFL Players          Michael S.        1 of 3 >
No Power 5 offers      UnderCruited QBs

| NFL Player | UnderCruited Player |
|---|---|
| All Players ⌄ | Michael Surrows ⌄ |
| 6'4, 250lbs | 6'4, 250lbs |
| Quarterback(s) | Quarterback |
| 22.4% | 22% |
| Athleticism Average | Athleticism 12-19-2018 |
| 48.8% | 50% |
| Playmaking Average | Playmaking 12-19-2018 |
| Schools & NFL Teams | School & Grad Year |
| ⚭ ⚭ | ◯ Class of '22 |
| 3 Colleges  3 Teams | ABC High School |

View Player Profile

FIG. 24A

Home    Fit Finder    My Board    Reports    @ My Account ˅

Welcome, Horace. Let's Get Started...

In order to get the most value out of Recruitment Analytics, you have to search for prospects using Fit Finder and then add them to Your Board, from there you can create reports and watch their performance over time and amongst their peers.

[ View My Board ]

Activity for Today, August 12, 2019

Social Engagement    Top Prospects

---

Most Important
Via Twitter Activity

Classification: Choose... ˅
Position: Choose... ˅

Film Grade Score ⓘ    Playmaking Ability ⓘ    Athleticism Score ⓘ    Last Name ⓘ
Select... ˅    Select... ˅    Select... ˅    Select... ˅

> Athleticism Score
> Explanation of athleticism score.
> Lorem ipsum dolor sit amet, consectetur adipiscing elit.

1. Jacob Matthews

Jacob Matthews '22 ···
6'4 250 | Linebacker
Atlanta, Georgia
⚭ 83%  77%  96%
Offers  Film  Athleticism  Playmaking
View Profile > | + My Watchlist | + My Board Geoffrey King ··· 📌
6'4 250 | Linebacker
Atlanta, Georgia
⚭ 61%  77%  96%
Offers  Film  Athleticism  Playmaking
View Profile > | + My Watchlist | ✪ My Board

3. Horace D. Williams

Jacob Matthews '22 ···
6'4 250 | Linebacker
Atlanta, Georgia
⚭ 83%  77%  96%
Offers  Film  Athleticism  Playmaking
View Profile > | + My Watchlist | + My Board

4. Alfonzo Cory

Jacob Matthews '22 ···
6'4 250 | Linebacker
Atlanta, Georgia
⚭ 83%  77%  96%
Offers  Film  Athleticism  Playmaking
View Profile > | + My Watchlist | + My Board

5. Marion Morris

Jacob Matthews '22 ···
6'4 250 | Linebacker
Atlanta, Georgia
⚭ 83%  77%  96%
Offers  Film  Athleticism  Playmaking
View Profile > | + My Watchlist | + My Board Create Dashboards using your own Prospects.
[ Go to Fit Finder ]

---

UnderCruited

Discover talent before anyone else even begins to see potential. Make your next play, your best play.

Learn More

3 NFL Players          Michael S.     1 of 3 >
No Power 5 offers     UnderCruited QBs NFL Player           UnderCruited Player
All Players ˅        Michael Surrows ˅

6'4, 250lbs          6'4, 250lbs
Quarterback(s)       Quarterback 22.4%                22%
Athleticism          Athleticism
Average              12-19-2018

48.8%                50%
Playmaking           Playmaking
Average              12-19-2018

Schools & NFL Teams   School & Grad Year
                      Class of
⚭ ⚭                  ○ '22
3 Colleges 3 Teams    ABC High School View Player Profile

Home   Fit Finder   My Board   Reports   My Account ⌄

← Unsaved Search ✎  (Edit Unsaved Search)

Lorem ipsum dolor sit amet, consectetur adipiscing elit, sed do eiusmod tempor incididunt ut labore et dolore magna aliqua. Ut enim ad minim veniam, quis nostrud exercitation ullamco laboris nisi ut aliquip ex ea commodo consequat.

| FBS Offers | Film Grade | Position | Vertical | Star Rating | 40 Yard | Height |
|---|---|---|---|---|---|---|
| 5+ OFFERS × | 5+ OFFERS × | 5+ OFFERS × | 5+ OFFERS × | 5+ OFFERS × | 5+ OFFERS × | 5+ OFFERS × |
| 5+ OFFERS × | | | 5+ OFFERS × | 5+ OFFERS × | | |
| Weight | Classification | Region | SAT Req. | Custom Search | Short Shuttle | GPA Req. |
| 5+ OFFERS × | NOTHING SELECTED ✎ | 5+ OFFERS × | 5+ OFFERS × | 5+ OFFERS × | 5+ OFFERS × | 5+ OFFERS × |
| 5+ OFFERS × | | | 5+ OFFERS × | 5+ OFFERS × | | |

← 18 Undercruited Results    (Return to Full Results)

18 prospects from your search match 12 NFL Players with no power 5 offers.

Sort By: First Name A-Z ⌄    Display Count: 12 Per Page ⌄

12 NFL Players with no power 5 offers.
Select one or more NFL players below to view prospects with similar athleticism and playmaking abilities

| ✓ Jacob Morrison LA Rams | Maurice Simms KC Chiefs (8 Results) | Jacob Morrison Houston Texans (8 Results) | Elliot Wiseman NY Giants (12 Results) | Paulo Simmons Philly Eagles (2 Results) |

← 5 OF 12 RESULTS → 1 [2] [3]

6 Prospects similar to (Jacob Morrison ×)

| 55% Overall % | 6'4 250lbs DB Height Weight Position | 55% Athleticism | 44% Playmaking | 46% Avg. Completion | 1.8 Yards Avg. Yards of Separation | 17 mph Top Speed | 0.28 sec Time to Top Speed |

| UC Jacob Matthews '22<br>6'0 210 \| Linebacker<br>Atlanta, Georgia<br>⊙ 22% \| 57% \| 96%<br>Offers \| Film \| Athleticism \| Playmaking<br>View Profile > \| + My Watchlist \| + My Board | UC Geoffrey King<br>6'4 250 \| Linebacker<br>Atlanta, Georgia<br>⊙ 61% \| 77% \| 44%<br>Offers \| Film \| Athleticism \| Playmaking<br>View Profile > \| + My Watchlist \| + My Board | UC Jacob Matthews '22<br>6'4 250 \| Linebacker<br>Atlanta, Georgia<br>⊙ 22% \| 53% \| 96%<br>Offers \| Film \| Athleticism \| Playmaking<br>View Profile > \| + My Watchlist \| + My Board |
| UC Michael Jerry Adams<br>6'0 210 \| Linebacker<br>Atlanta, Georgia<br>⊙ 83% \| 77% \| 44%<br>Offers \| Film \| Athleticism \| Playmaking<br>View Profile > \| + My Watchlist \| + My Board | UC Jacob Matthews '22<br>6'0 210 \| Linebacker<br>Atlanta, Georgia<br>⊙ 22% \| 77% \| 45%<br>Offers \| Film \| Athleticism \| Playmaking<br>View Profile > \| + My Watchlist \| + My Board | UC Jacob Matthews '22<br>6'0 210 \| Linebacker<br>Atlanta, Georgia<br>⊙ 61% \| 55% \| 43%<br>Offers \| Film \| Athleticism \| Playmaking<br>View Profile > \| + My Watchlist \| + My Board |

← 6 OF 6 RESULTS →

Unsaved Search ← Player Profile    152

Lorem ipsum dolor sit amet, consectetur adipiscing elit, sed do eiusmod tempor incididunt ut labore et dolore magna aliqua. Ut enim ad minim veniam, quis nostrud exercitation ullamco laboris nisi ut aliquip ex ea commodo consequat.

148

88% Film Grade
FBS – Power 5

53% Athleticism Score
FBS – Regional

92% Playmaking Score
FBS Elite

Jacob M. Matthews
Linebacker '22
Madra High School, Atlanta, Georgia

▷ Watch Game Film (3:32)
+ to My Board     + to Watchlist     + Notes

Most Recent Tweet
"I can't wait to get back on the field after this win!" #gomadras
@jmfootballgod

150

▭ Details

| Senior | Senior | Quarterback | 16 \| 10/07/2021 | 278lbs | 6ft, 4in |
|---|---|---|---|---|---|
| Class | Class | Position | Age / DOB | Weight | Height |
| View Details ⭕⭕⭕⭕⭕ Top 5 Schools | View Details ⭕⭕⭕⭕⭕ FBS Offers | No Commits Commitments | No Decommits Decommitments | ⭕ 2 Visits College Visits | |

150

📊 Statistics   Lorem ipsum dolor sit amet, consectetur

| 0.5 sec | 46% | 1.8 Yards | 17 Yards | 0.28 sec |
|---|---|---|---|---|
| Avg. Transition Time | Avg. Completion | Avg. Yards of Separation | Top Speed | Time to Top Speed |
| ▭55% FCS – Regional | ▭88% FBS Elite | ▭55% FCS – Regional | ▭88% FBS Elite | ▭88% FBS – Regional |
| 3 | 0.6 sec | 32% | 64.3 | 3 |
| Explosive Plays Allowed | Avg. Closing Speed | Catch Rate | QB Passer Rating | Avg. Yards After Catch Allowed |
| ▭88% FBS Elite | ▭88% FBS Elite | ▭88% FBS Elite | ▭23% Below Average | ▭55% FCS – Regional |

SYSTEMS, METHODS, AND COMPUTER-PROGRAM PRODUCTS FOR ASSESSING ATHLETIC ABILITY AND GENERATING PERFORMANCE DATA

CROSS-REFERENCE TO RELATED APPLICATIONS

This Non-Provisional Patent Application claims priority benefit of U.S. Provisional Patent App. No. 63/011,976, filed Apr. 17, 2020, titled "Systems, Methods, and Computer Program Products for Analyzing, Categorizing, and Ranking Athletes," and claims priority benefit of U.S. Provisional Patent App. No. 62/987,809, filed Mar. 10, 2020, titled "Systems, Methods, and Computer Program Products for Analyzing, Categorizing, and Ranking Athletes," and claims priority benefit of U.S. Provisional Patent App. No. 62/985,316, filed Mar. 4, 2020, titled "Systems, Methods, and Computer Program Products for Analyzing, Categorizing, and Ranking Athletes," all of which are incorporated herein by reference in the entirety.

TECHNICAL FIELD

The field relates to assessment of athletic ability.

BACKGROUND

The traditional process of recruiting athletes typically relies on individual, human-based assessment. This is often difficult and burdensome. The time and cost associated with recruiting, and the limited availability of useful data from which to base decisions, creates challenges. This is particularly true in college sports, where the number of athletes that must be reviewed is often significant relative to the resources available. For example, one recruiter may need to review hundreds of athletes in a relatively short period of time and make a decision on which athlete is the most suitable. In the end, even with a significant investment of time and resources, desirable candidates may be missed. Therefore, an improved process for assessing athletic ability is needed.

SUMMARY

This summary is intended to introduce a selection of concepts in a simplified form that are further described below in the detailed description section of this disclosure. This summary is not intended to identify key or essential features of the claimed subject matter, nor is it intended to be used as an aid in isolation to determine the scope of the claimed subject matter.

In brief, and at a high level, this disclosure describes, among other things, systems, methods, and computer-program products used for assessing athletic ability and generating athlete performance data that can be leveraged for recruiting, evaluating, comparing, and/or scouting purposes, among other uses. The performance data may be generated by an automated or semi-automated athlete assessment system that uses the athlete performance data to generate or update athlete profiles that can be searched, allowing athletes uniquely suited for a particular position, sport, and/or organization to be more easily identified. The athlete profiles may further be utilized for different forms of athletic assessment, e.g., recruiting (e.g., for college or professional sports organizations) and/or scouting, among other uses. The athlete assessment system may also be used to identify best-fit matches based on selected parameters, and may further generate alerts based on updates to an athlete's performance data and/or profile. The athlete assessment system may also utilize a computer-vision system to generate performance data from video analysis. For example, in one embodiment, athlete performance data is generated through computer-vision analysis of an athlete performing, e.g., in practice or gameplay. The generated performance data for the athlete may include, for example, maximum speed, maximum acceleration, time to maximum speed, transition time (e.g., time to change direction), closing speed (e.g., time to close the distance to another athlete), average separation (e.g., between the athlete and another athlete), play-making ability, athleticism (e.g., a weighted computation and/or combination of multiple metrics), and/or other performance data. This performance data may be used to generate and/or update a profile associated with the athlete. The athlete's profile may incorporate additional information, such as the athlete's height, weight, vertical jump, sprint time, sport, position, current organization, past organization(s), social media information, test scores, and/or any other information desired to be included in the athlete's profile. These generated athlete profiles may be integrated with a technology platform that provides a user-interface through which suitable athlete candidates, e.g., for a particular sport, position, and/or organization, can be searched and identified from a pool of possible athletes with greater efficiency, and precision, than a traditional human-based assessment process. For example, in one aspect, a computer system provides a user-interface that allows desired athlete parameters to be selected, and then a selection of athletes matching those parameters can be generated for recruitment consideration.

In one embodiment, a computer-implemented method for generating athlete performance data using computer-vision analysis is provided. The method comprises accessing a video, the video comprising a plurality of frames depicting an athlete, each of the plurality of frames having an associated time-stamp; identifying, using a computer-vision system, a location of the athlete in each frame of the plurality of frames; identifying, using the computer-vision system, a location of a reference element in each frame of the plurality of frames; identifying, using the computer-vision system, a number of pixels between the athlete and the reference element in each frame of the plurality of frames to thereby determine a pixel-distance between the athlete and the reference element in each frame; converting, using the computer-vision system, each pixel-distance to a corresponding physical distance; generating performance data for the athlete using the converted physical distance at each time-stamp; and updating a profile associated with the athlete to include the generated performance data.

In another embodiment, one or more computer-readable media having computer-executable instructions stored thereon are provided that, when executed by one or more computer processors, perform a method for generating athlete performance data through computer-vision analysis. The method comprises accessing a video, the video comprising a plurality of frames depicting an athlete, each of the plurality of frames having an associated time-stamp; identifying, using a computer-vision system, a location of the athlete in each frame of the plurality of frames; identifying, using the computer-vision system, a location of a reference element in each frame of the plurality of frames; identifying, using the computer-vision system, a number of pixels between the athlete and the reference element in each frame of the plurality of frames to thereby determine a pixel-distance between the athlete and the reference element in each frame; converting, using the computer-vision system, each pixel-distance to a corresponding physical distance; generating performance data for the athlete using the converted physical distance at each time-stamp; and updating a profile associated with the athlete to include the performance data.

In another embodiment, a computer system configured for generating athlete performance data using computer-vision analysis is provided. The computer system comprises at least one processor and one or more computer-readable media having computer-executable instructions stored thereon that, when executed by the at least one processor, perform a method for generating athlete performance data. The method comprises accessing a video, the video comprising a plurality of frames depicting an athlete, each of the plurality of frames having an associated time-stamp; identifying, using a computer-vision system, a location of the athlete in each frame of the plurality of frames; identifying, using the computer-vision system, a location of a reference element in each frame of the plurality of frames; identifying, using the computer-vision system, a number of pixels between the athlete and the reference element in each frame of the plurality of frames to thereby determine a pixel-distance between the athlete and the reference element in each frame; converting, using the computer-vision system, each pixel-distance to a corresponding physical distance; generating performance data for the athlete using the converted physical distance at each time-stamp; and updating a profile associated with the athlete to include the performance data.

In another embodiment, a computer-implemented method for generating athlete performance data in automated or semi-automated fashion using an athlete assessment system is provided. The method comprises accessing, by the athlete assessment system, a video, the video comprising a plurality of frames depicting an athlete; automatically identifying, by the athlete assessment system, a location of the athlete in each frame of the plurality of frames; automatically identifying, by the athlete assessment system, a location of a reference element in each frame of the plurality of frames; automatically identifying, by the athlete assessment system, a number of pixels between the athlete and the reference element in each frame of the plurality of frames to thereby determine a pixel-distance between the athlete and the reference element in each frame; automatically converting, by the athlete assessment system, each pixel-distance to a corresponding physical distance, e.g., using a calibration factor and/or a perspective transformation matrix; automatically generating, by the athlete assessment system, performance data for the athlete utilizing at least the converted physical distance in each frame; automatically updating, by the athlete assessment system, a profile associated with the athlete to include the generated performance data; and enabling identification of the athlete based on the generated performance data associated with the profile of the athlete.

In another embodiment, an automated or semi-automated athlete assessment system is provided. The system comprises at least one computer processor; at least one computer memory; and one or more computer-readable media having computer executable instructions stored thereon that, when executed by the at least one processor, perform a method comprising accessing, by the athlete assessment system, a video, the video comprising a plurality of frames depicting an athlete; automatically identifying, by the athlete assessment system, a location of the athlete in each frame of the plurality of frames; automatically identifying, by the athlete assessment system, a location of a reference element in each frame of the plurality of frames; automatically identifying, by the athlete assessment system, a number of pixels between the athlete and the reference element in each frame of the plurality of frames to thereby determine a pixel-distance between the athlete and the reference element in each frame; automatically converting, by the athlete assessment system, each pixel-distance to a corresponding physical distance, e.g., using a calibration factor and/or a perspective transformation matrix; automatically generating, by the athlete assessment system, performance data for the athlete utilizing at least the converted physical distance in each frame; automatically updating, by the athlete assessment system, a profile associated with the athlete to include the generated performance data; and enabling identification of the athlete based on the generated performance data associated with the profile of the athlete.

As used herein, an "athlete" may be one associated with any sport, including football, global football (i.e., soccer), baseball, basketball, lacrosse, track or running, hockey, water sports, or another sport.

BRIEF DESCRIPTION OF THE DRAWINGS

The systems, methods, and computer-program products described herein that are used for assessing athletes and generating performance data are described in detail with reference to the attached drawing figures, which are intended to illustrate non-limiting examples, wherein:

FIG. 22 depicts graphs representing athlete closing speed, generated using computer-vision analysis, in accordance with an embodiment of the present technology;

FIG. 23 depicts a computer-vision process for determining athlete separation, in accordance with an embodiment of the present technology;

FIGS. 24A-24B collectively depict a user-interface of a technology platform used for athlete assessment and/or recruiting and/or scouting, in accordance with an embodiment of the present technology;

FIGS. 25A-25B collectively depict the user-interface of FIGS. 24A-24B with different athlete information presented, in accordance with an embodiment of the present technology;

FIG. 28 depicts another user-interface associated with a technology platform used for athlete assessment and/or recruiting and/or scouting, in accordance with an embodiment of the present technology;

FIGS. 29A-29B collectively depict another user-interface associated with a technology platform used for athlete assessment and/or recruiting and/or scouting, in accordance with an embodiment of the present technology;

DETAILED DESCRIPTION

Figure 1:
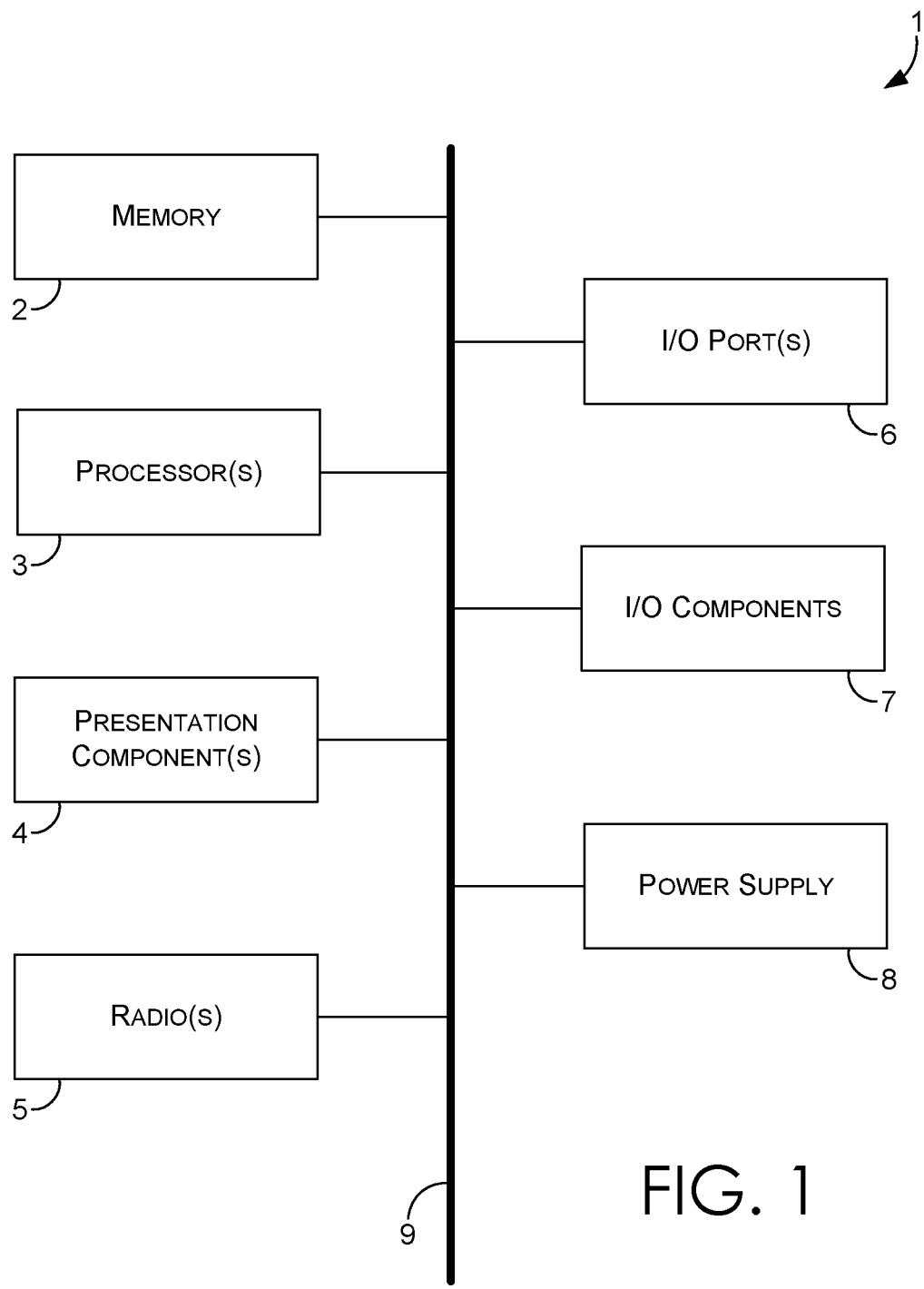
FIG. 1 depicts an example computing system suitable for supporting operation of the embodiments described herein.

This description is provided in order to meet statutory requirements. However, this description is not intended to limit the scope of the invention. Rather, the claimed subject matter may be embodied in other ways, to include different steps, combinations of steps, different features, and/or different combinations of features, similar to those described herein, and in conjunction with other present or future technologies. Moreover, although the terms "step" or "block" may be used herein to identify different elements of methods employed, the terms should not be interpreted as implying any particular order among or between various elements except when the order is explicitly stated.

In general, and at a high level, this disclosure describes, among other things, systems, methods, and computer-program products used for assessing athletic performance and generating performance data for athletes that can be leveraged for recruitment purposes. The embodiments described herein allow for many types of athlete performance data to be generated through video analysis. The generated performance data may further be used to create profiles for athletes, allowing athletes with preferred characteristics to be identified more efficiently and accurately, with reduced reliance on human-based athletic assessment, among other benefits. Detailed examples of the technology are described below with reference to FIGS. 1-45B.

The subject matter of this disclosure may be provided as, at least in part, a method, a system, and/or a computer-program product, among other things. Accordingly, certain aspects disclosed herein may take the form of hardware, or may be a combination of software and hardware. A computer-program that includes computer-useable instructions embodied on one or more computer-readable media may also be used. The subject matter herein may further be implemented as hard-coded into the mechanical design of computing components and/or may be built into a computing system or technology platform used for assessing athletic performance and generating athlete performance data.

Computer-readable media may include volatile media, non-volatile media, removable media, and non-removable media, and may also include media readable by a database, a switch, and/or various other network devices. Network switches, routers, and related components are conventional in nature, as are methods of communicating with the same, and thus, further elaboration is not provided here. By way of example, and not limitation, computer-readable media may include computer storage media and/or non-transitory communications media.

Computer storage media, or machine-readable media, may include media implemented in any method or technology for storing information. Examples of stored information include computer-useable instructions, data structures, program modules, and/or other data representations. Computer storage media may include, but is not limited to, RAM, ROM, EEPROM, flash memory or other memory technology, CD-ROM, digital versatile discs (DVD), holographic media or other optical disc storage, magnetic cassettes, magnetic tape, magnetic disk storage, and other storage devices. These memory components may store data momentarily, temporarily, and/or permanently, and are not limited to the examples provided herein.

Referring now to FIG. 1, a block diagram of an example computing device 1 suitable for supporting operation of the embodiments described herein is provided. It should be noted that although some components depicted in FIG. 1 are shown in the singular, they may be plural, and the components may be connected in a different, including distributed, configuration. For example, computing device 1 might include multiple processors and/or multiple radios. Also shown in FIG. 1, computing device 1 includes a bus 9 that may directly or indirectly connect multiple components together, including memory 2, processor(s) 3, presentation component(s) 4, radio(s) 5, input/output (I/O) port(s) 6, input/output (I/O) component(s) 7, and power supply 8, if any such components are applicable or used.

Memory 2 may take the form of the memory components described herein. Thus, further elaboration will not be provided here, but memory 2 may include any type of tangible medium that is capable of storing information, such as a database. A database may include any collection of records, data, and/or other information. In one embodiment, memory 2 may include a set of computer-executable instructions that, when executed, facilitate various functions or steps associated with the subject matter described herein. These instructions will be referred to as "instructions" or an "application" for short. The processor 3 may actually be multiple processors that may receive instructions and process them accordingly. The presentation component 4 may include a display, a speaker, a screen, a portable digital device, and/or other components that can present information through visual, auditory, and/or other tactile cues (e.g., a display, a screen, a lamp, a light-emitting diode (LED), a graphical user interface (GUI), and/or a lighted keyboard).

The radio 5 may facilitate communication with a network, and may additionally or alternatively facilitate other types of wireless communications, such as Wi-Fi, WiMAX, LTE, Bluetooth, and/or VoIP communications, among other communication protocols. In various aspects, the radio 5 may be configured to support multiple technologies, and/or multiple radios may be configured and utilized to support multiple technologies.

The input/output (I/O) ports 6 may take a variety of forms. Example I/O ports may include a USB jack, a stereo jack, an infrared port, and/or other proprietary communications ports. The input/output (I/O) components 7 may comprise one or more keyboards, microphones, speakers, touchscreens, and/or any other item useable to directly or indirectly input data into the computing device 1. The power supply 8 may comprise batteries, generators, fuel cells, and/or any other component that may act as a power source to supply power to computing device 1 and to any other connected components described herein.

To generate athlete performance data, a number of processes may be used. For example, athlete data may be obtained from different sources and compiled, analyzed, and/or transformed, and then used to generate, or update, a unique profile, and/or associated scores, statistics, and/or rankings associated with the athlete. In one example, performance data for an athlete may be obtained through computer-vision analysis of video depicting the athlete during an athletic performance, e.g., during practice or gameplay. This information may be, in additional aspects, combined with other athlete information, such as the athlete's height, weight, speed, academic characteristics, sport, playing position, geographic location, and/or other data. In additional aspects, athlete performance data and profiles that are generated and/or updated using the aspects described herein may be implemented with a technology platform that allows athletes with certain desirable characteristics or capabilities to be identified, with reduced reliance on human-based assessment, among other benefits. For example, based on a particular athlete need, a pool of athlete profiles may be identified, and provided, based on which of those athletes are suited for a particular position, team, sport, or overall organization. The data used to generate an athlete profile may include computer-generated data, and/or data obtained and/or generated using artificial intelligence ("AI") or machine learning ("ML"). This data may be used to compute desired metrics (e.g., rankings, scores, comparisons, recommendations, and the like) for use in providing strategic recommendations for candidate athletes.

In numerous embodiments of the technology described herein, AI and/or ML may be used in combination with computer vision to obtain, review, and/or analyze athlete data, e.g., images and/or video of candidate athletes. The use of computer analysis, such as AI-powered and/or ML-powered image and video analysis, allows certain information, such as top speed, average separation, play completion, and/or other characteristics to be determined from raw video footage. This information may then be utilized to generate a unique profile, as well as rankings, statistics, and/or scores for the athlete, according to certain categories. For example, using the technology described herein, recommendations for best athlete, best pool of athletes, best athlete based on position, best pool of athletes based on position, film and/or data grades, play-making ability, and/or overall athleticism rankings may be generated and used as a recruiting tool. This approach allows significant volumes of raw player data (e.g., extended film of athletes during gameplay or practice) to be reviewed and leveraged to produce valuable profiles/recommendations, thereby saving time and money while also producing more valuable recruiting information. These technological improvements may be used with or without the use of player-attached hardware, such as sensors or radio frequency identification ("RFID") tags. This may reduce or limit the equipment complexity and cost of obtaining useful performance data for athletes.

Figure 2:
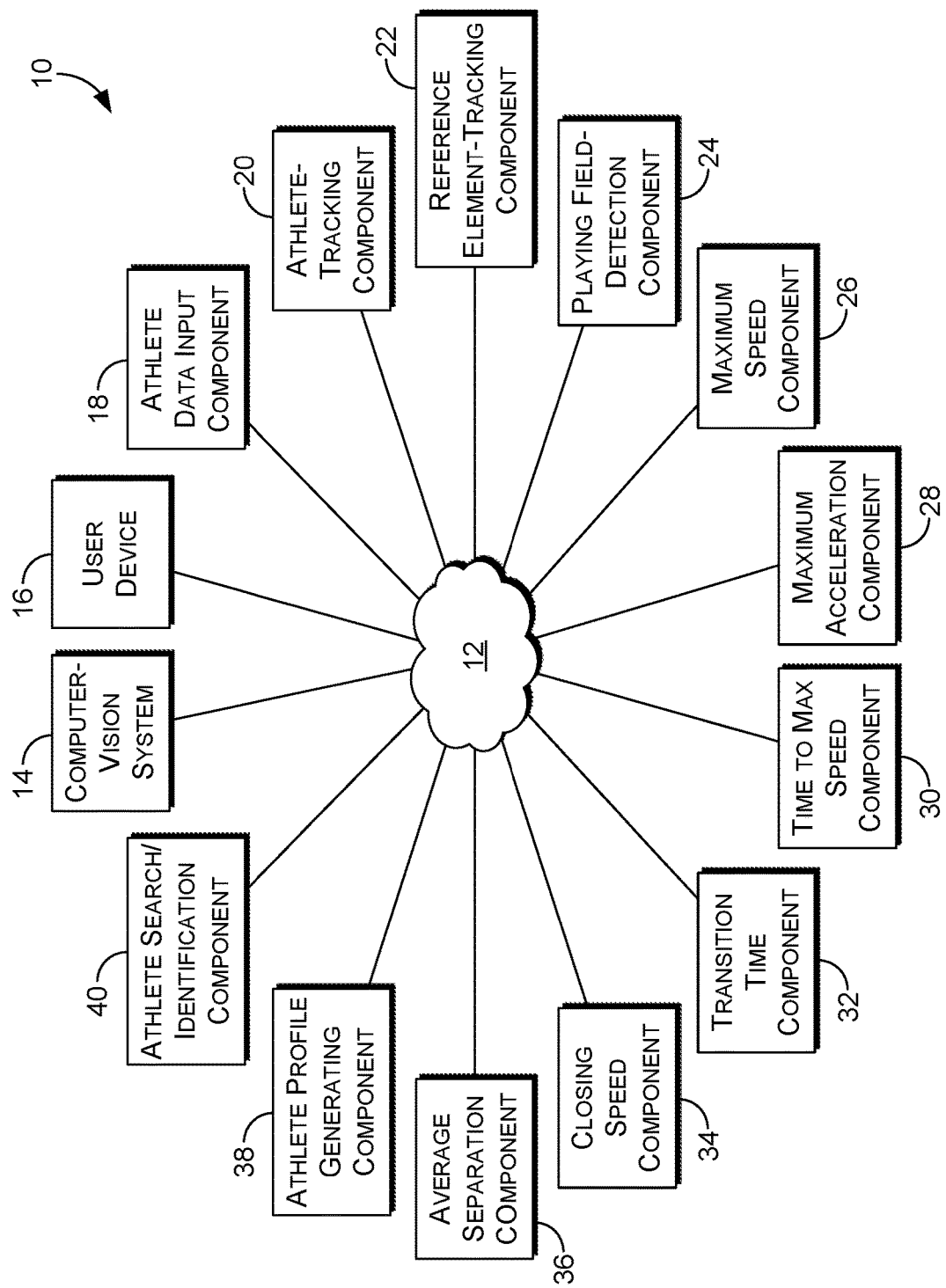
FIG. 2 depicts an example network of components useable for assessing athletic ability and generating performance data, in accordance with an embodiment of the present technology.

Referring now to FIG. 2, an example system 10 used for assessing athletic ability and generating performance data that can be leveraged for athlete assessment, recruiting, and/or scouting is provided, in accordance with an embodiment of the present technology. The system 10 shown in FIG. 2 includes a selection of components that are connected over a network 12. Further, while a number of different components are represented in FIG. 2, more, fewer, or different components may be used in different aspects, and accordingly, the selection represented in FIG. 2 is intended to illustrate only one non-limiting example. Further, any combination of these components may collectively form an athlete assessment system, e.g., one that operates in automated or semi-automated fashion to perform the different operations described herein.

FIG. 2 depicts a computer-vision system 14 connected to the network 12. The computer-vision system 14 may actually represent a combination of data-capturing and/or data-processing components that operate to track, analyze, and/or generate performance data for an athlete through analysis of video of the athlete. The computer-vision system 14 may include, for example, one or more processors, memories, sensors, algorithms, and/or other software and/or hardware that operate to obtain and/or generate performance data for an athlete.

To illustrate one example process, the computer-vision system 14 may access, e.g., receive or upload, a video of an athlete depicting an athletic performance. For the purposes of this description, an "athletic performance" or "athletic activity" may include any athletic circumstance, e.g., such as practice, gameplay, athletic testing, or another circumstance. The video that is accessed may include a plurality of frames each depicting the athlete during the athletic activity. The computer-vision system 14 may identify the athlete, allowing the athlete to be tracked throughout the different frames of the video. The identification of the athlete in the video may be automatic, or semi-automatic, e.g., being performed by a computer processor, or may be provided through some form of manual direction. For example, in one instance, a tag, box, or other designator may be associated with the athlete in the video, thereby allowing the computer-vision system 14 to track the athlete throughout the plurality of frames.

The computer-vision system 14 may be configured to identify one or more reference elements in an environment, e.g., an area or space, in which the athlete is performing, as shown in the frames of the video. The reference element(s) may be fixed elements, e.g., fixed geometric objects located in the environment, such as physical structures, boundaries, lines, and the like, and/or may be moveable elements, e.g., other athletes in the environment that change position, and/or may be game implements, such as a game ball (e.g., a football, a basketball, a baseball, a golf ball, a tennis ball, a soccer ball, a hockey puck, or another game ball), or an athlete-associated object (e.g., a baseball bat, a tennis racket, a hockey stick, a golf club, or the like). The reference elements may be identified, and tracked, similar to the process used to identify and track an athlete. The computer-vision system 14 may further be configured to detect, once the athlete and the reference element(s) are identified, a pixel distance between the athlete and the reference element(s) in each frame. Then, each pixel distance may be converted to a corresponding physical distance (e.g., feet, yards, meters, etc.) in the environment. The conversion may be performed using a calibration factor, which may include a mathematical function that changes the pixel-distance into corresponding physical distance based on a conversion equation that takes into account a depth value in the frame. The conversion may also be performed using a perspective transformation matrix. The resulting physical distance between the athlete and the reference element(s) at each time-stamped frame may be used to generate different types of athlete performance data. This performance data may be used to determine, for example, a maximum speed, a time to maximum speed, a maximum acceleration, a transition time, a closing time, or other metrics through frame-by-frame analysis of time, direction, and distance traveled by the athlete, as described in further detail below.

FIG. 2 also depicts a user-device 16 connected to the network 12. The user-device 16 may represent one of multiple devices through which the system is accessed, directed, and/or used. For example, the user-device 16 may be a computer, or a mobile device, such as a tablet, mobile phone, or another hand-held device. The user-device 16 may further include a graphical user-interface ("GUI"). The GUI may display data, and/or receive inputs, in different aspects. For example, the user-device 16 may be a computer that can be used to access and search performance data for athletes, and/or access and search athlete profiles. The user-device 16 may also be configured to receive user-selected parameters, thereby allowing athletes with characteristics corresponding to the selected parameters to be identified and presented to the user.

FIG. 2 also depicts an athlete data input component 18 ("ADI component 18") that is connected to the network 12. The ADI component 18 is a component that allows for input of data that may be used to generate or update an athlete's profile. For example, an athlete's height, weight, sport, position, age, performance statistics (e.g., from competitive gameplay) and/or other athlete data may be input into the system using the ADI component 18. The input data, in another aspect, may also be used to select parameters through which athlete profiles are sorted, allowing suitable athlete candidates to be identified, and presented, based on the selected parameters. The inputs for these selections may be, for example, text boxes, drop-down lists, buttons, and/or other modifiable features that allow desired parameters to be designated.

FIG. 2 also depicts an athlete-tracking component 20 that is connected to the network 12. The athlete-tracking component 20 may form part of, and/or may operate in conjunction with, the computer-vision system 14, in one aspect. The athlete-tracking component 20 may be configured to detect, identify, and/or track an athlete in frames of a video depicting the athlete during an athletic performance. For example, the athlete-tracking component 20 may be configured to tag, or designate, an athlete in a video, allowing the athlete location and relative position to be tracked throughout the frames of the video. This may allow the athlete's direction, speed, and acceleration to be determined, among other metrics. In one aspect, the athlete is tracked using a shape that is associated with the athlete (e.g., a box, or circle), which is tracked in each frame of the video.

FIG. 2 also depicts a reference-element tracking component 22 that is connected to the network 12. The reference-element tracking component 22 may form part of, and/or may operate in conjunction with, the computer-vision system 14. The reference-element tracking component 22 may, like the athlete-tracking component 20, be configured to detect, identify, and/or track one or more reference elements depicted in frames of a video. In addition, one or more of the tracked reference elements may be fixed elements, such as fixed geometric structures, boundaries, markers (e.g., lines, solid or dashed), or the like, and/or one or more of the tracked reference elements may be non-fixed elements, such as other athletes performing along with the tracked athlete. The reference-element tracking component 22 may be configured to tag, or otherwise designate, the reference elements in the frames of the video, allowing them to be tracked, e.g., for use in determining relative positioning.

FIG. 2 also depicts a playing field detection component 24 that is connected to the network 12. The playing field detection component 24 may form part of, and/or may operate in conjunction with, the computer-vision system 14. The playing field detection component 24 is configured to detect and/or identify an environment, e.g., a space and/or area, including characteristics and features thereof, in which an athlete is performing in frames of a video. The detected aspects may include the reference elements discussed in the preceding section. In one aspect, the athlete-tracking component 20, the reference element detection component 22, and the playing field detection component 24 may be at least partially integrated, and may operate together, to facilitate the generation of athlete performance data from video analysis.

FIG. 2 also depicts a maximum speed component 26 that is connected to the network 12. The maximum speed component 26 may form part of, and/or may operate in conjunction with, the computer-vision system 14. The maximum speed component 26 may be configured to generate and/or compute a maximum speed of an athlete from video of the athlete performing. For example, a pixel-separation between an athlete and any identified reference elements may be determined for each frame of a video depicting the athlete and the identified reference elements. Then, the pixel-separation in each frame may be converted into a corresponding physical distance. The conversion may be performed using a calibration factor, which may use a mathematical function to change pixel-distance into real world distance based on a conversion equation that takes into account depth values in the frame. The conversion may also be performed using a perspective transformation matrix. The actual physical distance identified in each frame, in combination with a corresponding time stamp of each frame, may be used to determine a distance traveled over time, or between frames. The maximum distance traveled per time interval or between frames may be used to determine the maximum speed of the athlete in the video. This information may be used to generate or update an athlete profile, allowing the athlete's maximum speed to be used as an identifiable, or searchable, characteristic of the athlete.

FIG. 2 also depicts a maximum acceleration component 28 that is connected to the network 12. The maximum acceleration component 28 may form part of, and/or may operate in conjunction with, the computer-vision system 14. The maximum acceleration component 28 may be configured to generate and/or compute a maximum acceleration of an athlete from video analysis of the athlete. For example, a pixel-separation between the athlete and any identified reference elements may be determined for each frame of a video that depicts the athlete and the identified reference elements. Then, the pixel-separation may be converted into a corresponding physical distance as described above. The speed of the athlete at each frame may be determined based on the change in position between frames, and then, the acceleration of the athlete may be generated and/or computed based on the change in velocity over time, to determine the maximum acceleration achieved by the athlete in the video. This information may be used to generate or update an athlete profile, allowing the athlete's maximum acceleration to be used as an identifiable, or searchable, characteristic of the athlete.

FIG. 2 also depicts a time to maximum speed component 30 that is connected to the network 12. The time to maximum speed component 30 may form part of, and/or may operate in conjunction with, the computer-vision system 14. The time to maximum speed component 30 is configured to generate and/or compute a time it takes for an athlete to go from a velocity of zero, or from a first velocity, to a maximum velocity in frames of a video. The starting velocity may also be interpolated and/or extrapolated to zero, if desired. Initially, the speed of the athlete at different frames may be generated and/or computed, as described in the preceding section. Then, a maximum speed of the athlete in the video may be determined, as described in the preceding section. Then, starting from a velocity of zero, or starting from some initial velocity, the time elapsed for the athlete to achieve a maximum speed is determined. This information may be used to generate or update an athlete profile, allowing the athlete's time to maximum speed to be used as an identifiable, or searchable, characteristic of the athlete.

FIG. 2 also depicts a transition time component 32 that is connected to the network 12. The transition time component 32 may form part of, and/or may operate in conjunction with, the computer-vision system 14. The transition time component 32 is configured to generate and/or compute a time it takes for an athlete to complete a change in direction. This process may include determining when the athlete is traveling in a first direction, i.e., along a first vector, in the frames of the video, and then determining when the athlete is traveling in a second direction, i.e., along a second vector, in the frames of the video, and then determining the number of frames required to complete the directional change and from that the time elapsed. In addition, multiple transitions may be tracked and used to generate an average transition time for an athlete, in an additional aspect. This information may be used to generate or update an athlete profile, allowing the transition time or average transition time to be used as an identifiable, or searchable, characteristic of the athlete.

FIG. 2 also depicts a closing speed component 34 that is connected to the network 12. The closing speed component 34 may form part of, and/or may operate in conjunction with, the computer-vision system 14. The closing speed component 34 is configured to generate and/or compute a time required for an athlete to close a distance. For example, a time required to close a distance between the athlete and an identified reference element, e.g., a goal line, or the time required to close a distance between the athlete and another athlete, e.g., during a play, may be determined. To provide one example, a frame of a video at which an athlete starts moving in the direction of another athlete or an object may be determined. The distance between the athlete and the other athlete, or object, may be determined by identifying a pixel-distance, and converting the pixel-distance to a physical distance, e.g., using a calibration factor and/or transformation matrix as described herein. The frame of the video at which the athlete has closed the distance may then be determined. Then, a number of frames and their associated time stamps may be used to generate and/or compute a closing time for the athlete. In addition, multiple closing times may be generated and/or computed to allow an average closing time for the athlete to be determined. This information may be used to generate or update an athlete profile, allowing the closing time or average closing time to be used as an identifiable, or searchable, characteristic of the athlete.

FIG. 2 also depicts an average separation component 36 that is connected to the network 12. The average separation component 36 may form part of, and/or may operate in conjunction with, the computer-vision system 14. The average separation component 36 is configured to determine an average distance between an athlete and another athlete during a period of time, e.g., during a play. This metric may demonstrate the athlete's ability to complete a play by maintaining distance from another athlete. In one aspect, the pixel-separation between an athlete and another athlete during an athletic performance may be determined across multiple frames of a video. The determined pixel-separations may be converted into corresponding physical distances as described herein, and these distances may then be averaged to determine an average separation over a number of frames, or a period of time.

FIG. 2 also depicts an athlete profile generating component 38 that is connected to the network 12. The athlete profile generating component 38 may form part of, and/or may operate in conjunction with, the computer-vision system 14. The athlete profile generating component 38 is configured to generate, compile, and/or store performance data and other information associated with an athlete. This allows a profile associated with the athlete to be dynamically updated, so that when a user, e.g., an athlete recruiter, desires to locate athlete candidates based on selected parameters, the athlete profiles generated by the athlete profile generating component 38 may be searched to locate suitable candidates with reduced reliance on human-based assessment.

FIG. 2 also depicts an athlete search/identification component 40 that is connected to the network 12. The athlete search/identification component 40 is configured to enable athlete profiles, e.g., those generated by the athlete profile generating component 38, to be searched, allowing suitable athlete candidates to be located with greater efficiency and/or precision using the system 10. For example, through the user-device 16, user-desired athlete parameters may be selected, such as an athlete's maximum speed, maximum acceleration, time to maximum speed, closing speed, transition time, and/or other user-selectable athlete parameters. In addition, the different metrics for each athlete that are retuned by the system 10 may be given corresponding weights, thereby allowing them to be used to calculate an athleticism score. For example, for a particular sport, or position, certain characteristics (e.g., maximum speed, maximum acceleration, etc.) may be weighted more heavily, thereby allowing the athleticism score to be more influenced by those metrics.

Figure 3:
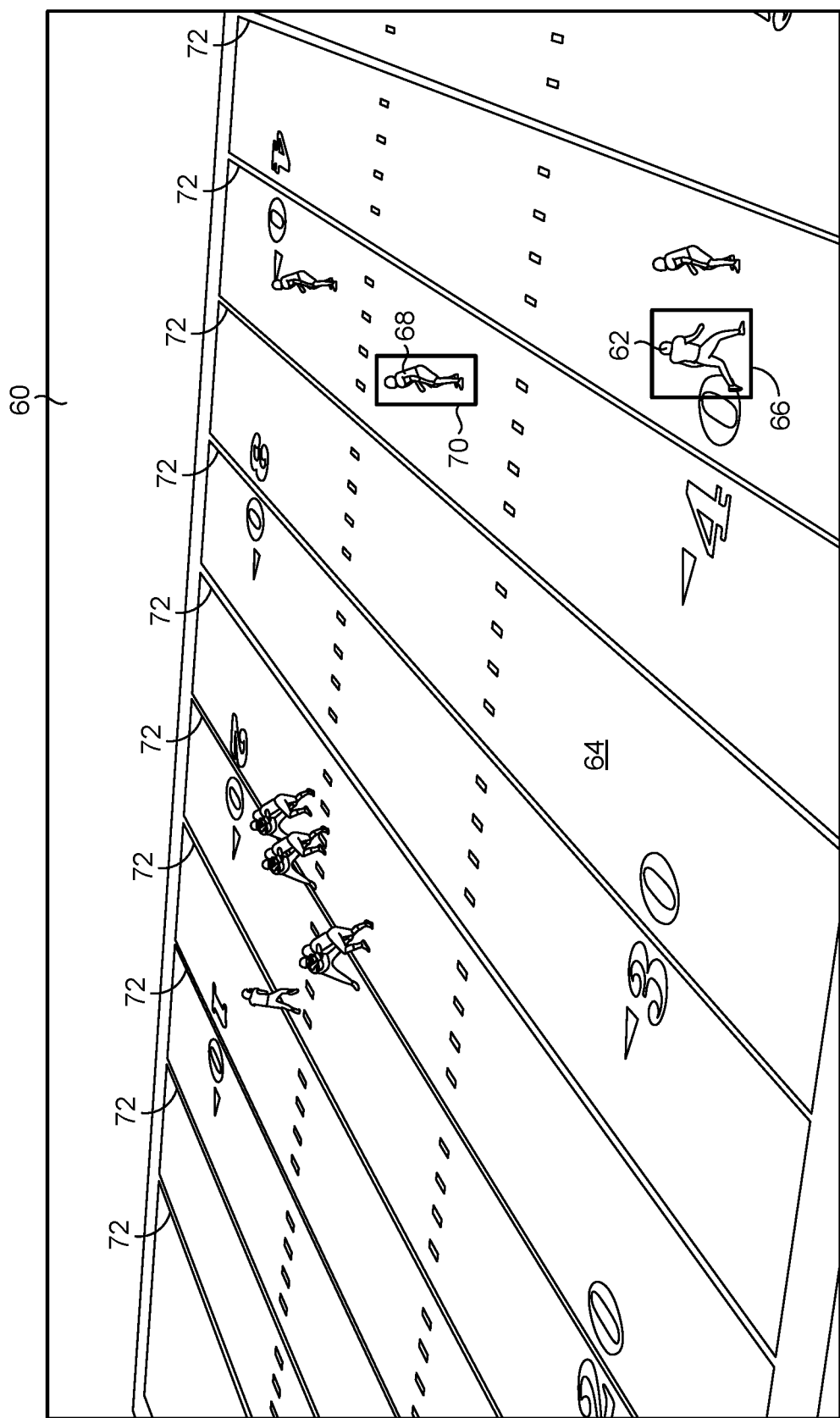
FIG. 3 depicts part of a computer-vision analysis used to generate athlete performance data, in accordance with an embodiment of the present technology.

Referring now to FIG. 3, part of a computer-vision process used for athlete analysis is provided, in accordance with an embodiment of the present technology. FIG. 3 depicts a frame 60 of a video showing an athlete 62 during athletic activity. The athlete 62 may be a high-school athlete, a college athlete, a professional athlete, or another athlete candidate. In the frame 60, an environment 64, i.e., a gameplay area or space, is shown. In addition, a designator 66, e.g., a digital boundary box, is associated with the athlete 62 by a computer-vision system. The designator 66 allows a location of the athlete 62 in the environment 64 to be tracked by the computer-vision system throughout a plurality of frames of the video.

FIG. 3 depicts, within the environment 64, other elements that may be detected, and tracked, by the computer-vision system frame-by-frame. For example, for the purposes of illustration, another athlete 68 is shown in the environment 64. Like the athlete 62, the athlete 68 has a designator 70, e.g., a digital boundary box, associated with it by the computer-vision system. The designator 70 allows a location of the athlete 68 in the environment 64 to be tracked by the computer-vision system. This also allows the relative positioning of the athlete 62 and the athlete 68 to be tracked frame-by-frame. For example, a pixel-separation between the athlete 62 and the athlete 68 may be determined in each frame, and then each pixel-separation may be converted to a corresponding physical distance, e.g., using a calibration factor and/or a perspective transformation matrix, thereby allowing each pixel-distance to be converted to a correct physical distance in the corresponding portion of the environment 64.

FIG. 3 further depicts a non-limiting selection of reference elements 72 shown in the environment 64. The reference elements 72 may, for example, be fixed elements located in the environment 64, the location of which is determined by the computer-vision system. The identifying, locating, and tracking of the reference elements 72 may allow for calculation of athlete speed, acceleration, direction, and/or other characteristics through determination of relative positioning over time. The reference elements 72 may be fixed elements such as markers (e.g., field markers, goal posts, or other fixtures) or may be fixed markings (e.g., field lines, boundaries, indicators, and the like). In different aspects, the environment 64 may be any athletic area, e.g., a field, practice area, or other space in which some form of athletic activity occurs.

Figure 4:
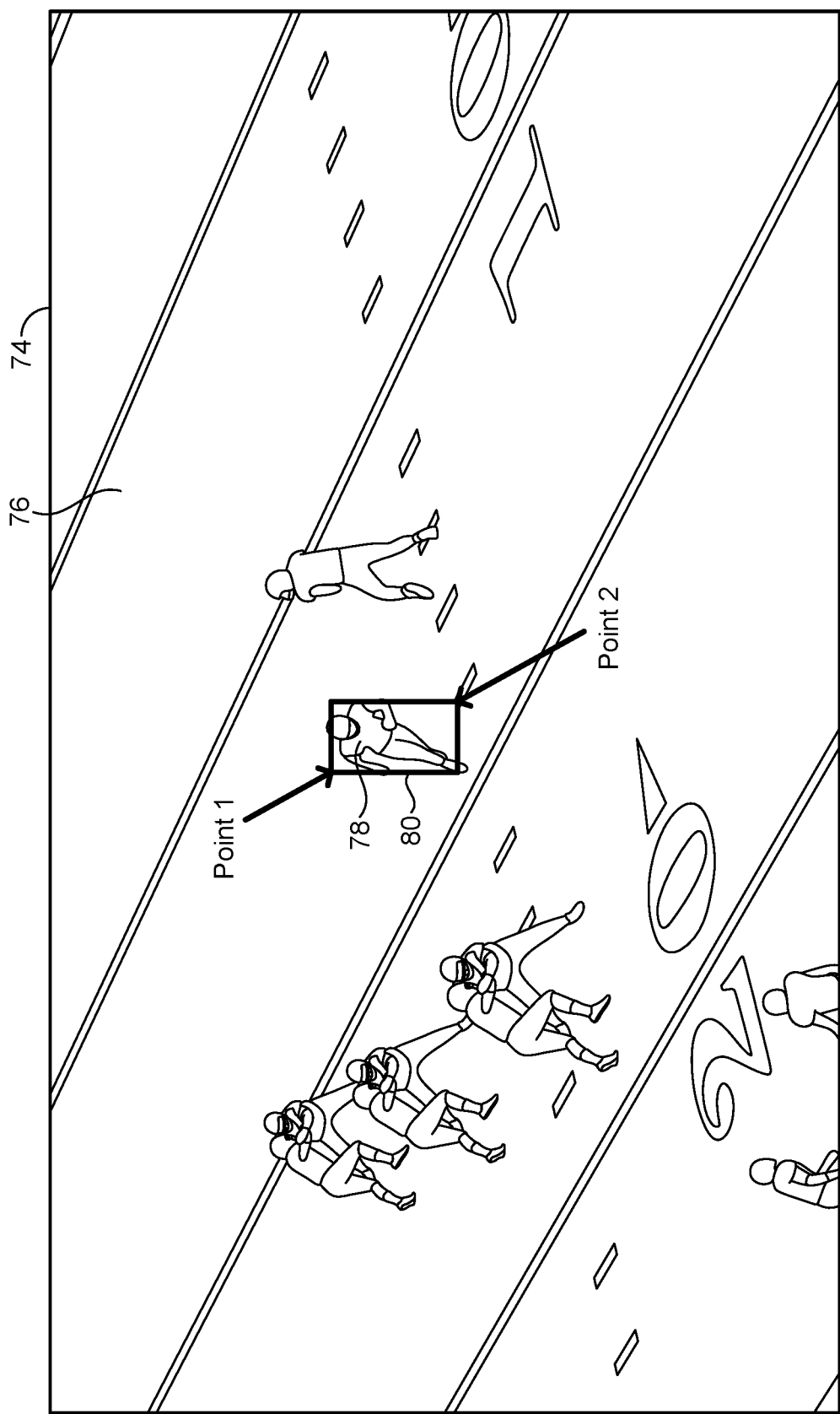
FIG. 4 depicts another part of a computer-vision analysis used to generate athlete performance data, in accordance with an embodiment of the present technology.

Referring now to FIG. 4, another part of a computer-vision process used for athlete analysis is provided, in accordance with an embodiment of the present technology. FIG. 4 depicts, once again, a frame 74 of a video. Within the frame 74 is an environment 76 in which an athlete 78 is located. FIG. 4 further shows the athlete 78 designated, e.g., tagged, with a designator 80. In FIG. 4, this designator is represented, for example purposes, as a digital bounding box. The designator 80 shifts in the frames of the video along with the position of the athlete 78, i.e., as the athlete moves, thereby allowing the computer-vision system to maintain tracking of the athlete 78. This designating or tagging process may be performed by the computer-vision system, e.g., based on recognition of the athlete 78, e.g., through a unique identifier associated with the athlete 78, and/or may be performed, at least in part, through a manual process. For example, the technology platform associated with the computer-vision system may allow a user of the platform to designate, e.g., tag, the particular athlete 78, and connect a stored profile with the athlete. Throughout the frames of the video, the different positions and directions of travel of the designator 80 may be used to track the movement of the athlete 78.

Figure 5:
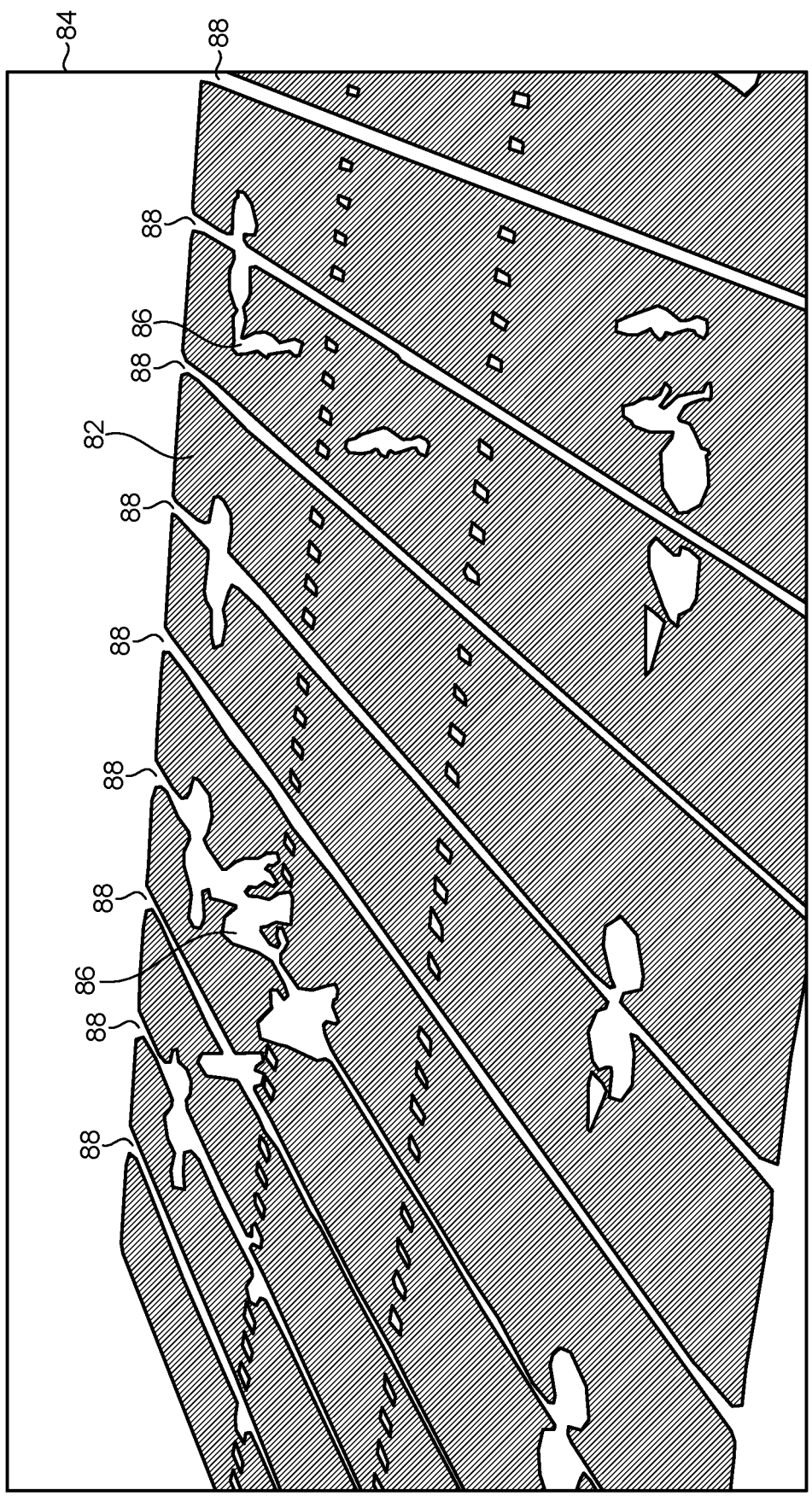
FIG. 5 depicts another part of a computer-vision analysis used to generate athlete performance data, in accordance with an embodiment of the present technology.

Referring now to FIG. 5, another part of a computer-vision process used for athlete analysis is provided, in accordance with an embodiment of the present technology. FIG. 5, in particular, depicts an example process of recognizing the geometry of an environment 82 in a frame 84, e.g., a playing field, in which athletic activity occurs. In one example process, a video is accessed, e.g., received or uploaded, and is then split into individual frames, e.g., like the frame 84 shown in FIG. 5. The frame 84 depicts athletes 86 performing in the environment 82. In each individual frame, one or more reference elements, e.g., geometric elements present in the environment 82, are detected and recognized. In this particular example, the reference elements are lines 88 on the playing field. FIG. 5 also depicts a color threshold being applied to the frame 84. In particular, there is a color applied for field color, and a color applied for marking color (e.g., to identify athletes and reference elements to be tracked). In other words, a color separation is applied between the field color and the marking color, allowing for differentiation by the computer-vision system, frame-to-frame.

Figure 6:
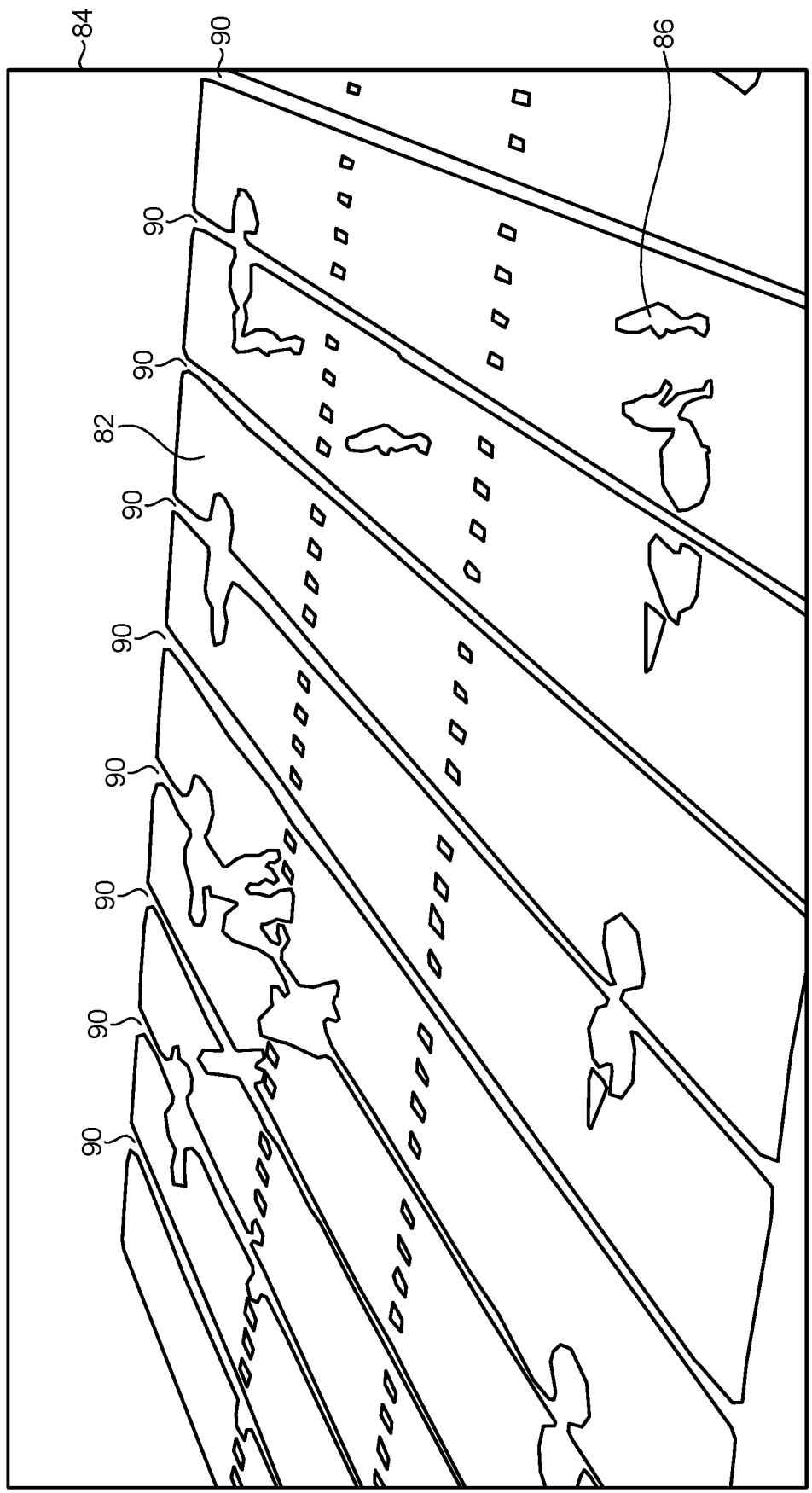
FIG. 6 depicts another part of a computer-vision analysis used to generate athlete performance data, in accordance with an embodiment of the present technology.

Referring to FIG. 6, another part of a computer-vision process used for athlete analysis is provided, in accordance with an embodiment of the present technology. FIG. 6 depicts a different representation of the frame 84 shown in FIG. 5, showing, in roughly identified form, transverse lines 90, i.e., lines extending side-to-side on a playing field, which have been identified by the computer-vision system. To recognize the transverse lines 90 in the environment 82, different processes may be used. For example, a Canny transform algorithm may be applied to the frame 84, to produce an edged image. The transform may be applied using open source platforms, e.g., such as OpenCV. Other methods of line recognition and image edging are also possible without departing from the scope of the present disclosure.

Figure 7:
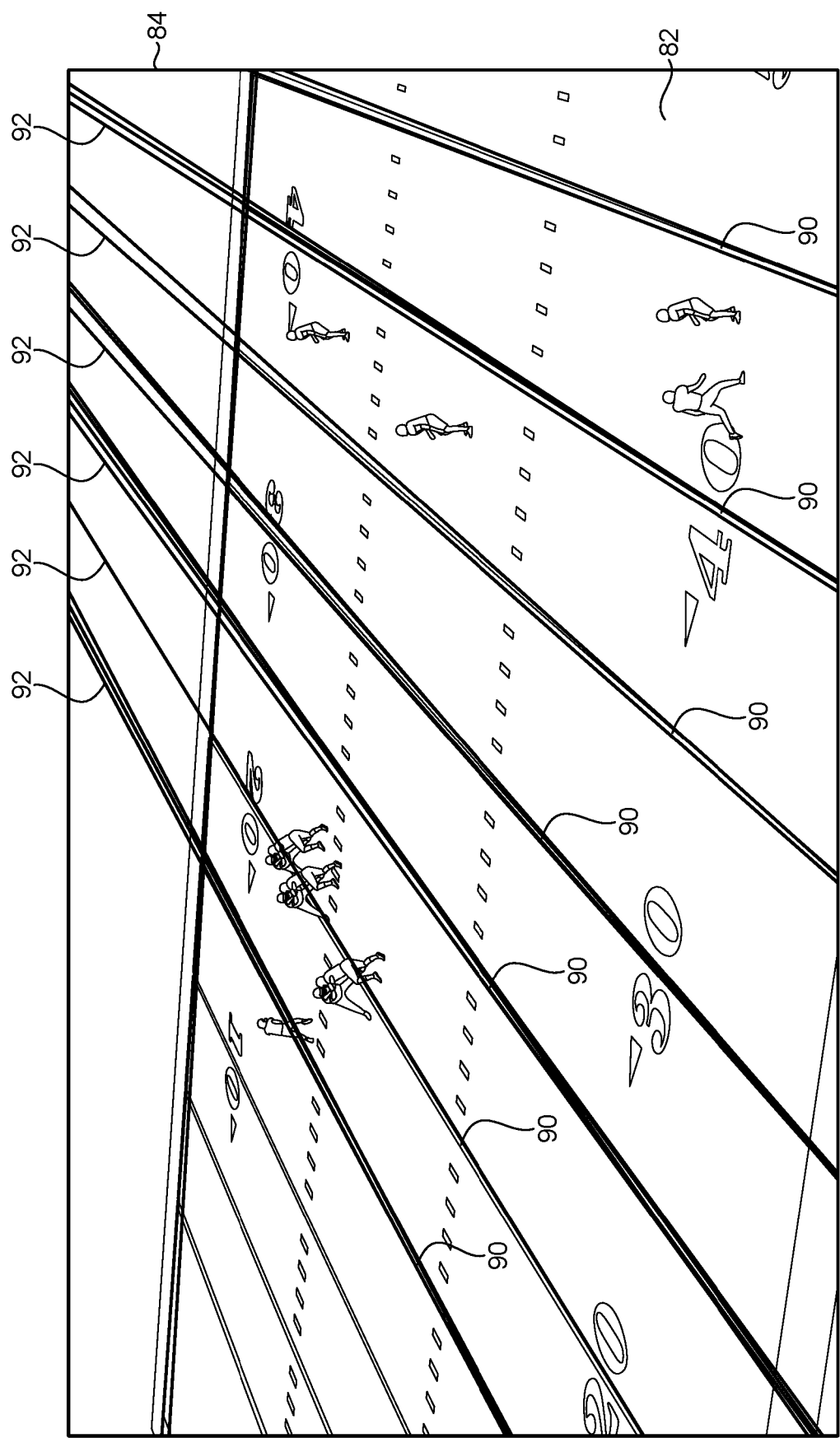
FIG. 7 depicts another part of a computer-vision analysis used to generate athlete performance data, in accordance with an embodiment of the present technology.

Referring now to FIG. 7, another part of a computer-vision process used for athlete analysis is provided, in accordance with an embodiment of the present technology. FIG. 7 depicts a different representation of the frame 84 shown in FIG. 6, in particular showing lines 92 transposed onto the lines 90 identified in the environment 82 in FIG. 6. To obtain the equations for the lines, in one aspect, a Hough transform may be used. In this process, multiple lines 92 may be transposed onto each line 90 identified in FIG. 6. In addition, clustering of the lines 92 may be performed using a scanning algorithm, e.g., such as a Density-Based Spatial Clustering of Applications with Noise (i.e., DBSCAN) algorithm, among others.

Figure 8:
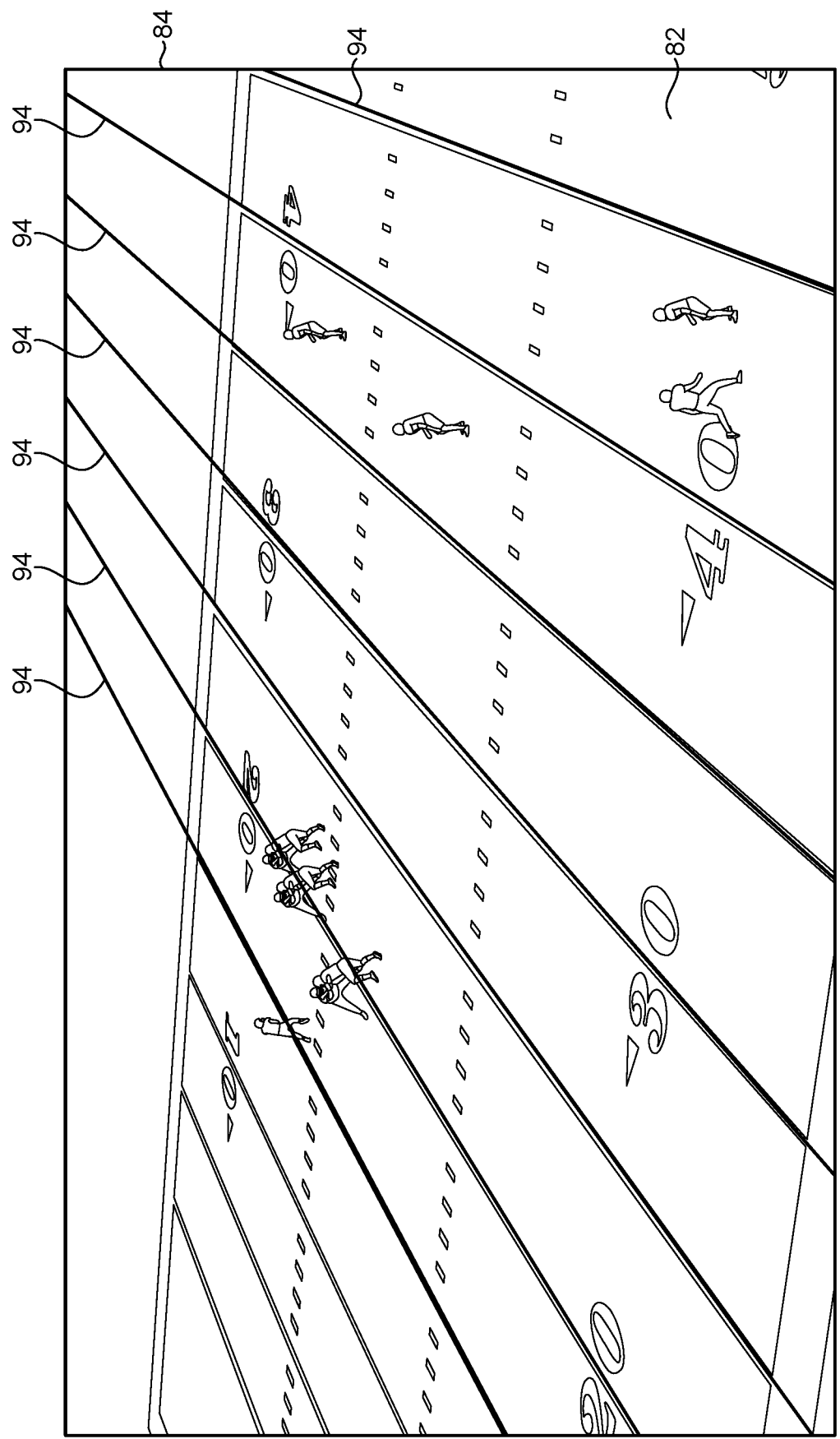
FIG. 8 depicts another part of a computer-vision analysis used to generate athlete performance data, in accordance with an embodiment of the present technology.

Referring now to FIG. 8, another part of a computer-vision process used for athlete analysis is provided, in accordance with an embodiment of the present technology. FIG. 8 in particular depicts the frame 84 of FIGS. 6 and 7, now showing single consolidated lines 94 transposed onto the actual lines 90 on the playing field in the environment 82. The consolidation of the lines 92 into common, more closely matched lines 94 provides greater precision in the tracking process. To perform this consolidation, the lines 92 shown in FIG. 7 may be averaged within each cluster corresponding to a line 90 shown in FIG. 6, and the resulting lines may then be filtered such that the lines do not intersect within the frame 84. The resulting set of lines may then pass through a series of filters to remove lines that do not closely match the actual lines on the field, resulting in the lines 94 shown in FIG. 8. This process of consolidating and/or filtering lines may be performed for each frame, e.g., automatically, to allow reference elements to be detected and used for athlete analysis.

Figure 9:
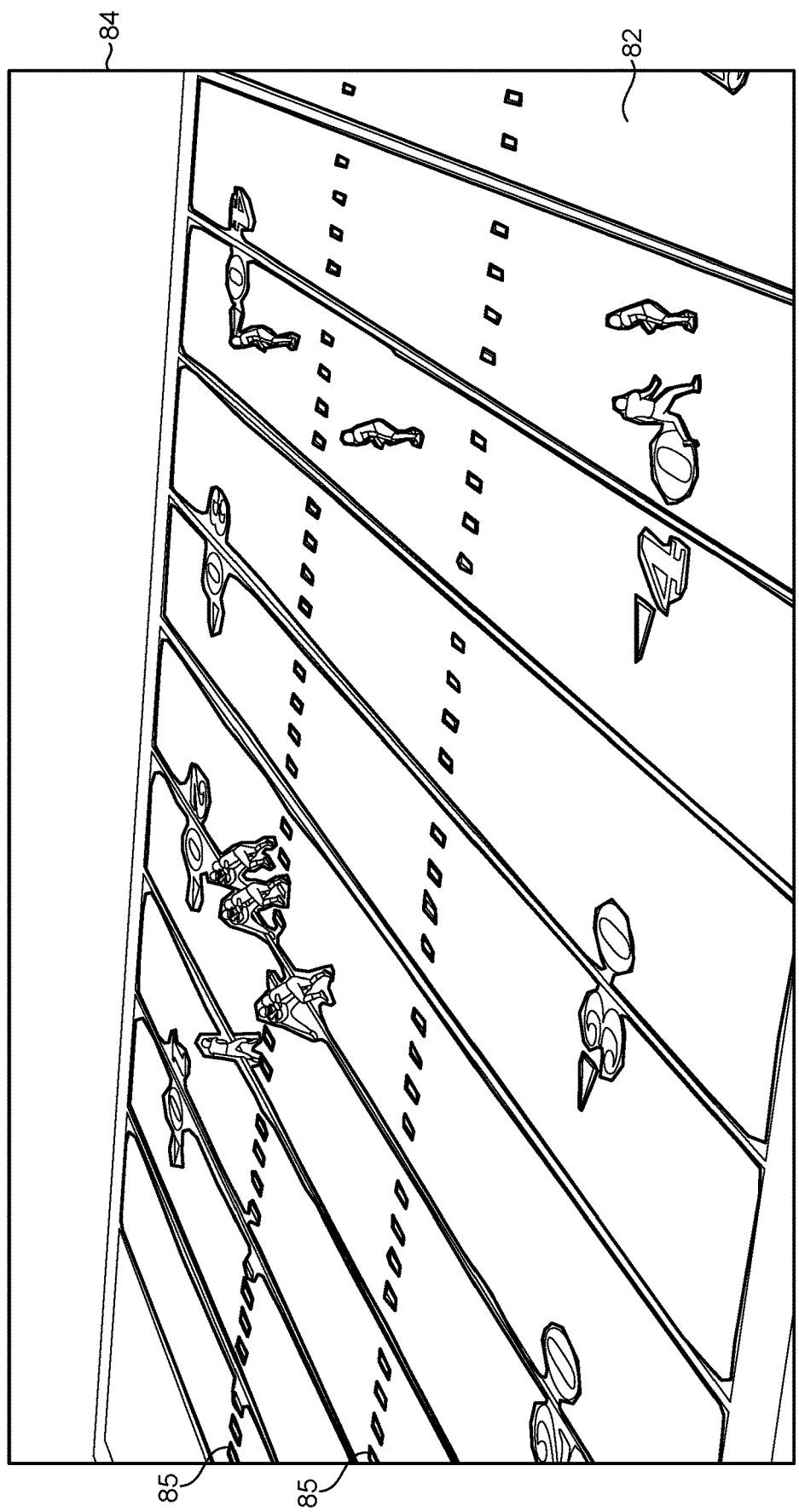
FIG. 9 depicts another part of a computer-vision analysis used to generate athlete performance data, in accordance with an embodiment of the present technology.
Figure 10:
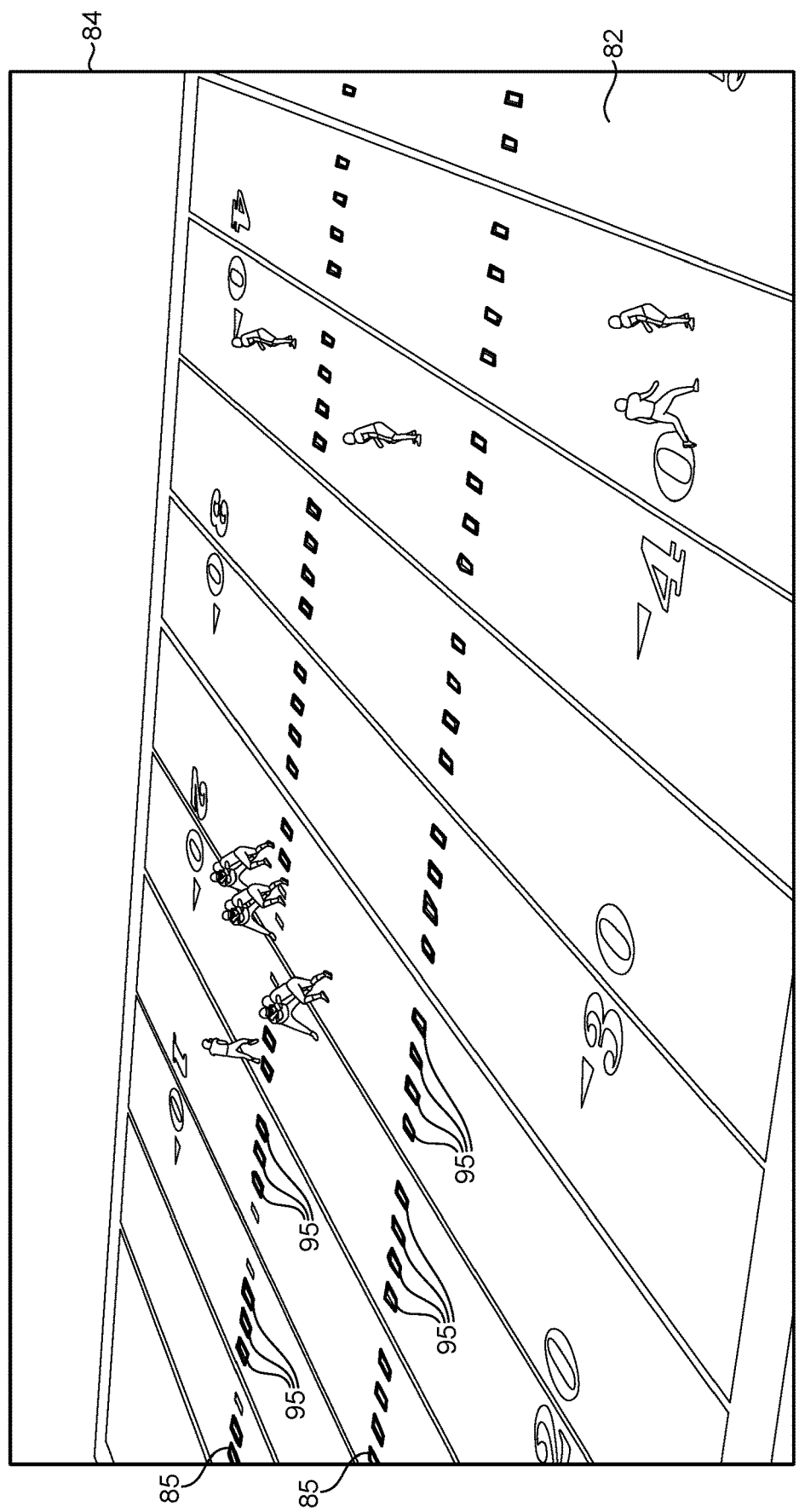
FIG. 10 depicts another part of a computer-vision analysis used to generate athlete performance data, in accordance with an embodiment of the present technology.

Referring now to FIGS. 9-10, another part of a computer-vision process used for athlete analysis is provided, in accordance with an embodiment of the present technology. FIG. 9 depicts a process by which non-solid, e.g., dashed or dotted, lines 85 may be detected in the environment 82 shown in the frame 84. Initially, all boundaries and/or lines may be identified in the frame 84 by the computer-vision system. Looking at FIG. 10, the lines and/or boundaries may then be filtered, e.g., using a DBSCAN algorithm, so that lines outside a threshold size range are removed. For example, the threshold size range may be determined based on a standard size of markings on a playing field for a particular sport (e.g., lines on a football field). The remaining lines 95 of a similar size, shape, and/or area may be considered desired objects and may be filtered by the color of the pixels inside the lines, so that pixels of a marking color, i.e., a color transposed to identify reference elements in the image, may be identified and used to determine the location of the non-solid lines extending longitudinally on the field.

Figure 11:
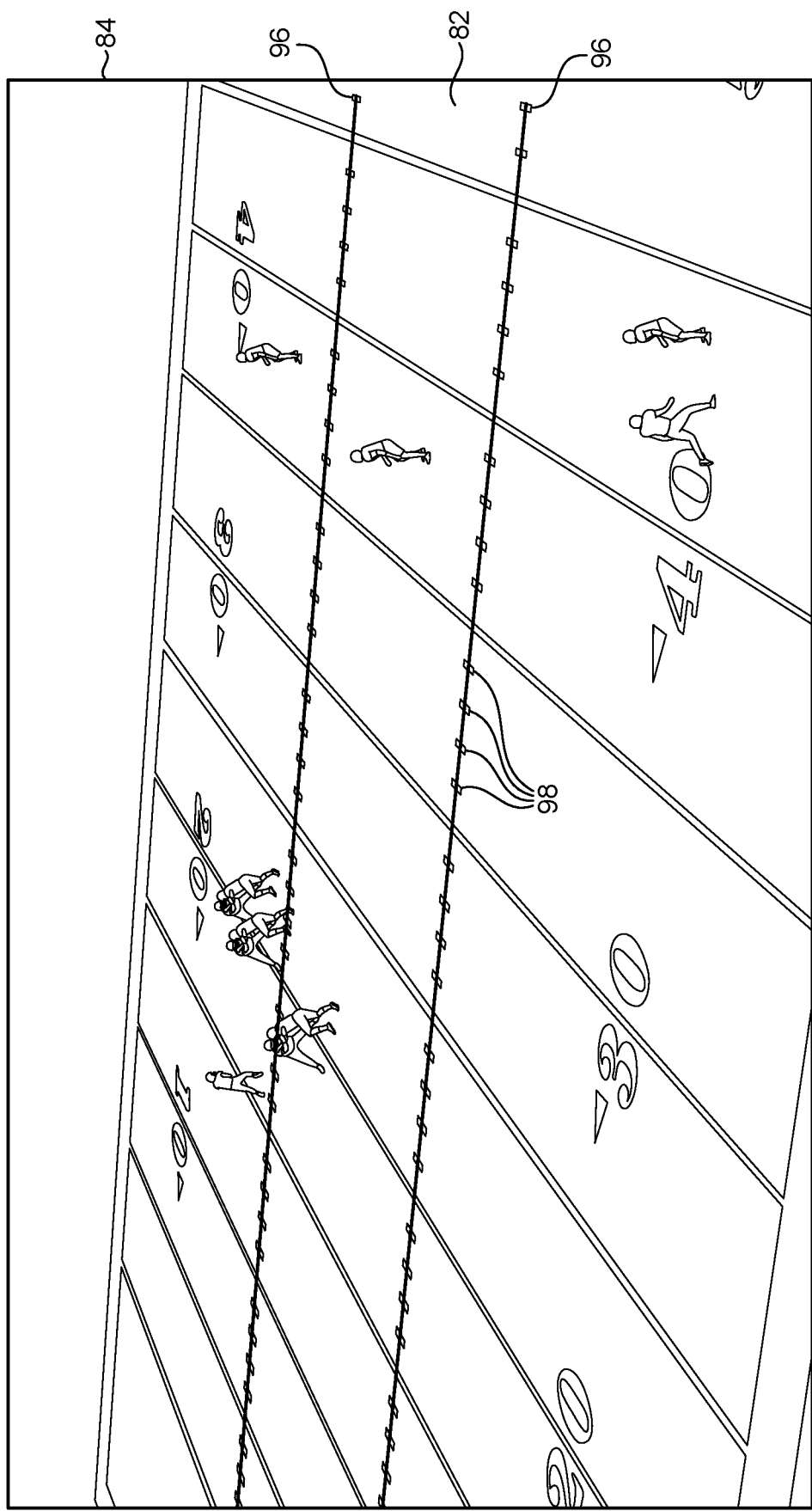
FIG. 11 depicts another part of a computer-vision analysis used to generate athlete performance data, in accordance with an embodiment of the present technology.
Figure 12:
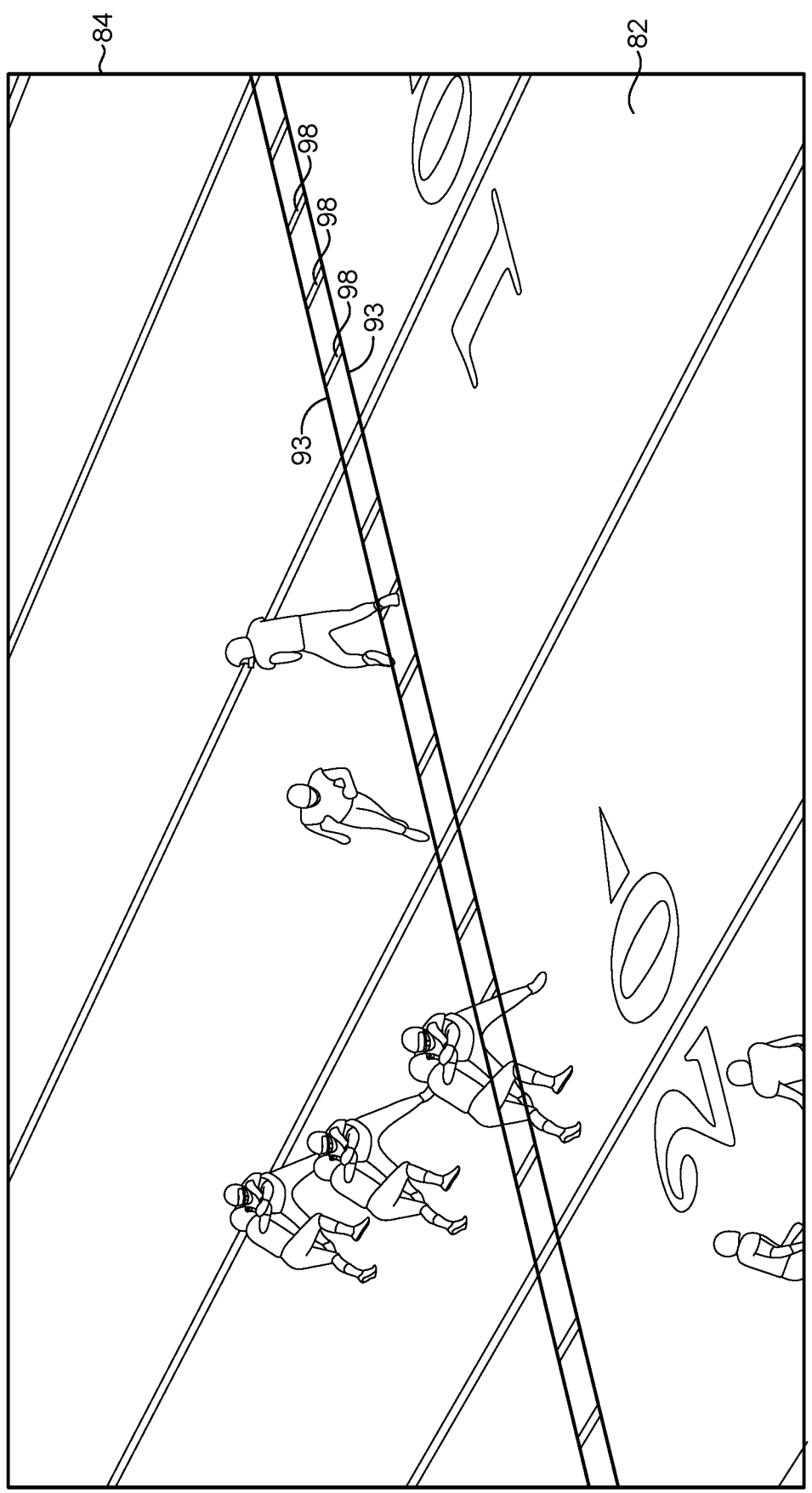
FIG. 12 depicts another part of a computer-vision analysis used to generate athlete performance data, in accordance with an embodiment of the present technology.

Referring now to FIG. 11, another part of a computer-vision process used for athlete analysis is provided, in accordance with an embodiment of the present technology. FIG. 11 depicts a process by which lines can be transposed through the centers of detected reference elements 98, e.g., dashed or dotted line elements, by the computer-vision system. To generate, and transpose, the lines 96 through the centers of the detected reference elements 98 extending in a common direction on the playing field, a Random Sample Consensus (RANSAC) algorithm or another similar algorithm may be used to locate in the frame 84 groups of geometric centers that fall, at least partially, along a common linear trajectory. The lines 96 are then extended through the geometric centers of the reference elements 98 as shown in FIG. 11. This process allows different, and more segmented, groups of reference elements to be identified and correlated. In a further aspect, if the algorithm used by the computer-vision system is unable to locate one or more lines passing through the centers of the detected reference elements, e.g., dashed or dotted line markings, extending along a common direction, then an alternative search for lines passing through end points of the reference elements extending along a common direction may be used, to identify a line that can be transposed on the reference elements. FIG. 12 depicts this alternative process of detecting reference elements 98, e.g., dashed or dotted lines, in the environment 82 depicted in the frame 84. FIG. 12 shows how if locating and/or transposing one or more lines through the centers of reference elements 98 extending in a common direction is not possible, then transposing one or more lines through end points of the reference elements may be used, as shown in FIG. 12.

Figure 13:
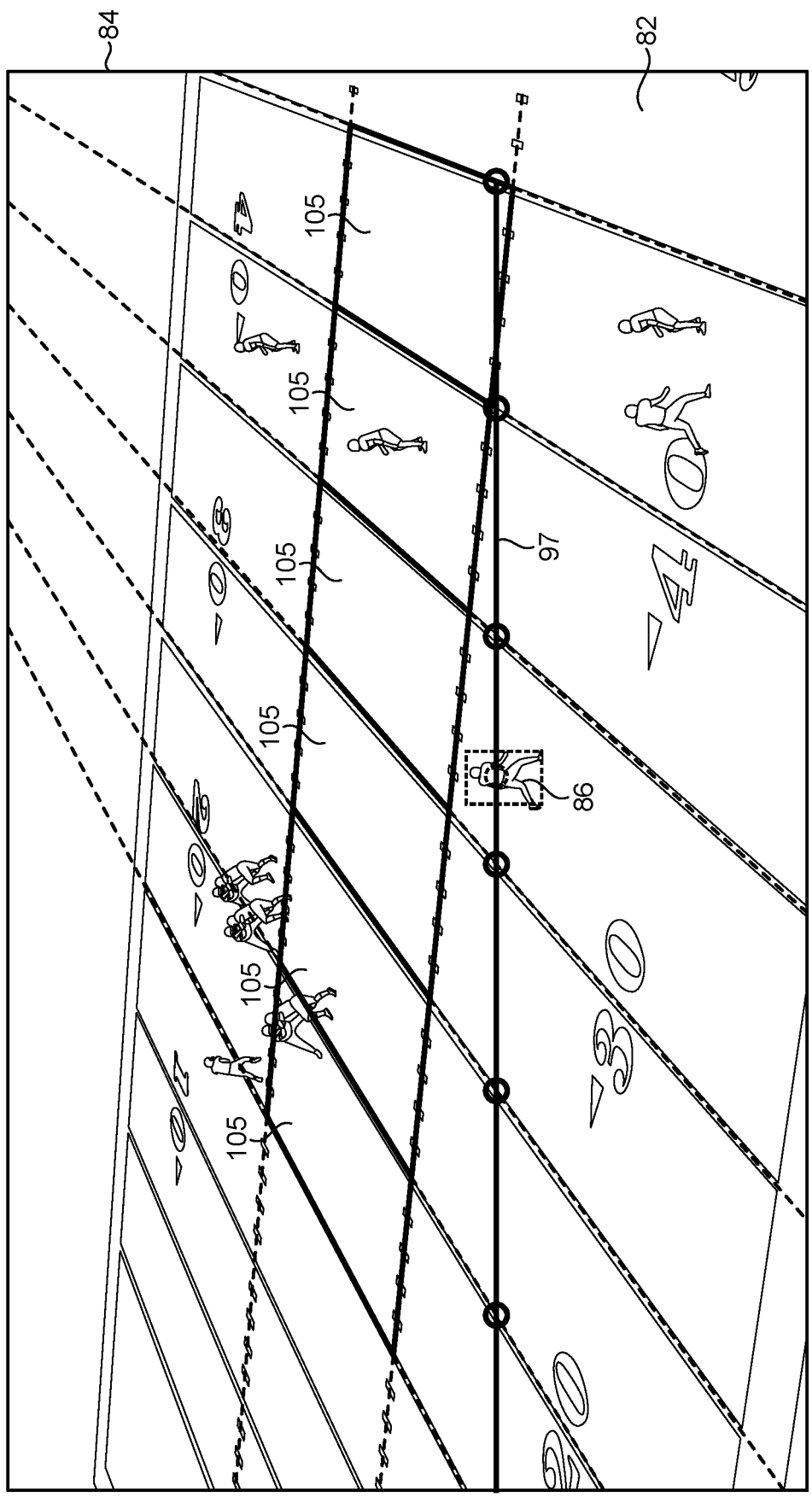
FIG. 13 depicts another part of a computer-vision analysis used to generate athlete performance data, in accordance with an embodiment of the present technology.
Figure 14:
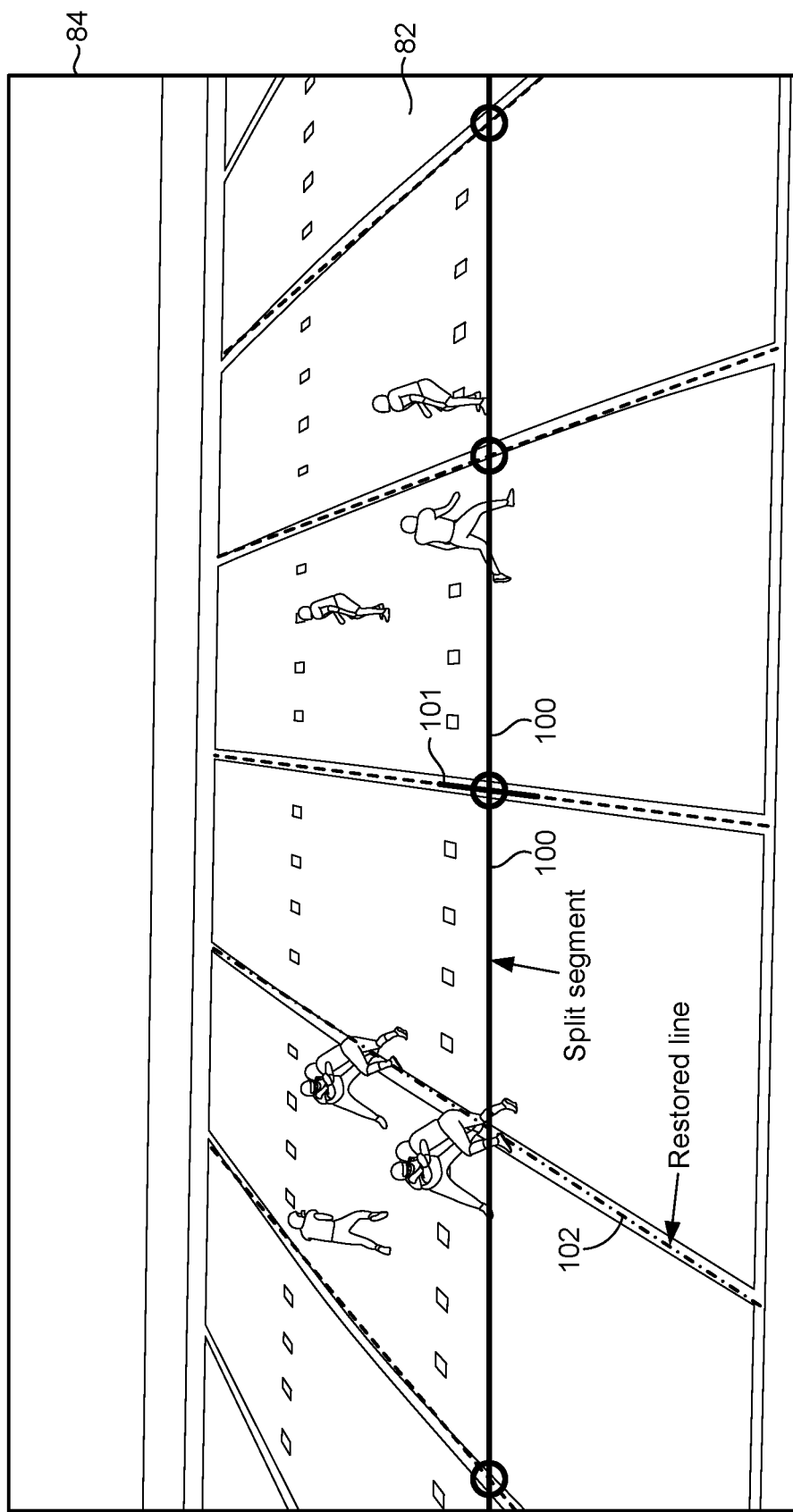
FIG. 14 depicts another part of a computer-vision analysis used to generate athlete performance data, in accordance with an embodiment of the present technology.

Referring now to FIG. 13, another part of a computer-vision process used for athlete analysis is provided, in accordance with an embodiment of the present technology. FIG. 13 depicts how the computer-vision system utilizes detected and/or transposed longitudinal and transverse lines to identify polygonal shapes 105, e.g., squares or rectangles, in the environment 82. In addition, shown in FIG. 13 is a vector line 97 of an athlete 86. During the process of identifying line segments and polygonal shapes, a filtering process may be used to refine the shapes, and restore missed lines. In addition, in instances when the longest detected line segment, e.g., longitudinal or transverse line segment, is a certain length, e.g., at least two times the average length of the other line segments, the line segment may be divided into two separate, e.g., equal, line segments. This allows a missing line segment to be restored using averaged nearby or adjacent line segments. This is shown, for example, in FIG. 14, in which two line segments 100, originally detected as a single line segment, are split at transverse line 101 to form the two equal line segments 100. In addition, a restored line 102 that has been identified and transposed by the computer-vision system is also shown in FIG. 14. This process allows for a more complete identification of reference elements in the environment 82.

Figure 15:
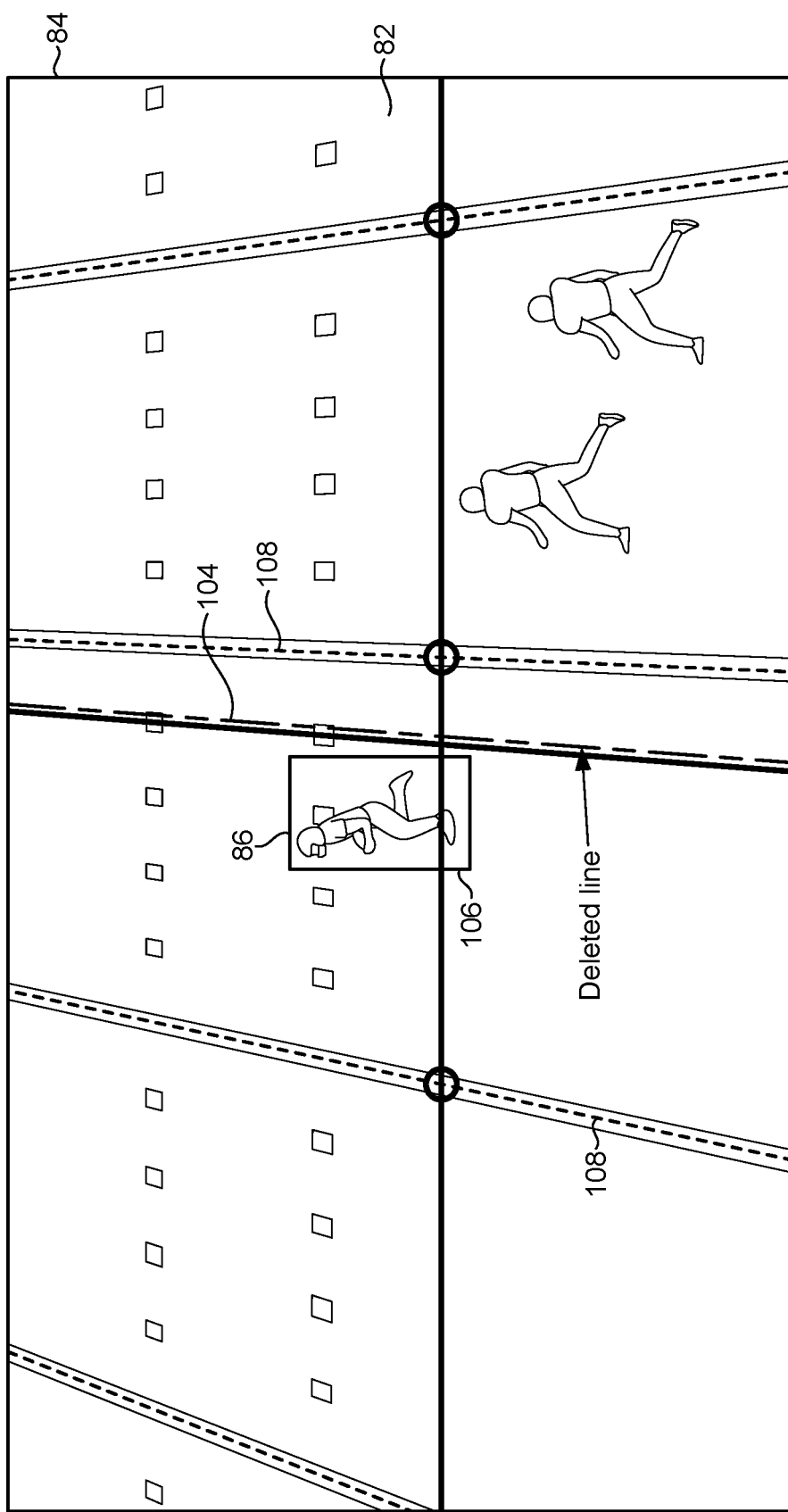
FIG. 15 depicts another part of a computer-vision analysis used to generate athlete performance data, in accordance with an embodiment of the present technology.

Referring now to FIG. 15, another part of a computer-vision process used for athlete analysis is provided, in accordance with an embodiment of the present technology. FIG. 15 in particular depicts how the computer-vision system, through an iterative process, is able to remove certain boundary lines in the frame 84. For example, if the removal of such lines leads to an increase in line segment uniformity, the deletion of the line, e.g., the deleted line 104, is maintained. In addition, when it is not possible to recognize longitudinal lines in the frame 84, e.g., due to the lines, at least in part, not being visible, then transverse line segments 108 may be identified and/or transposed. The ends of the transverse line segments 108 may be found at intersection points of a longitudinal line segment 103 passed through a position 106 of the athlete 86 and the transverse lines 108. These obtained segments may be used with a computer-vision algorithm for determining the speed of the athlete 86 in the frames of the video being analyzed.

Figure 16:
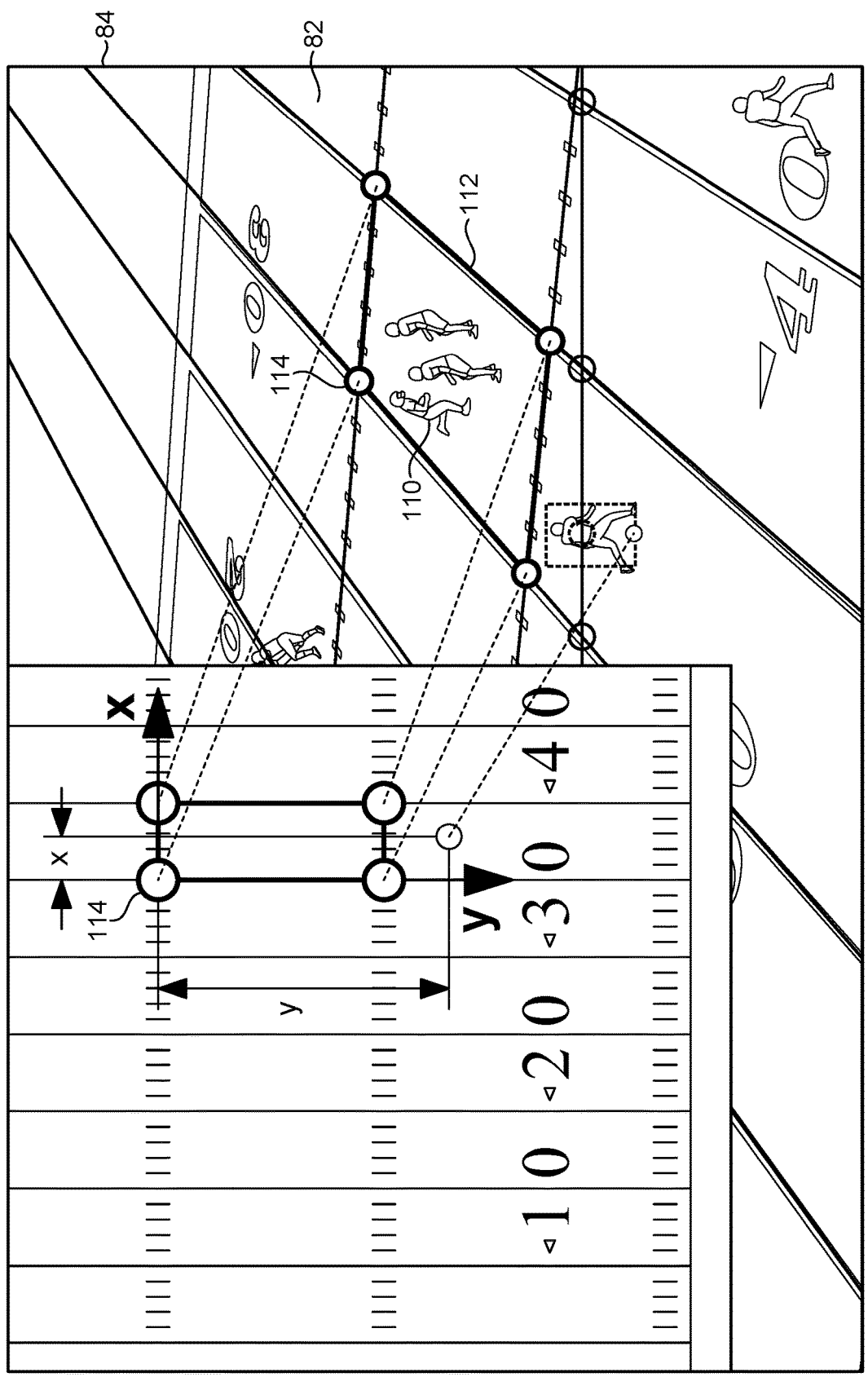
FIG. 16 depicts another part of a computer-vision analysis used to generate athlete performance data, in accordance with an embodiment of the present technology.

Referring now to FIG. 16, another part of a computer-vision process used for athlete analysis is provided, in accordance with an embodiment of the present technology. FIG. 16 in particular depicts a process of calculating the position and displacement of an athlete 110 across frames of a video, and also over a period of time (e.g., determined by time-stamps associated with the frames of the video). In order to calculate the displacement of an athlete 110 over a time interval between two frames of video, a position of the athlete 110 is determined relative to identified polygonal shapes, e.g., squares or rectangles, on two or more sequential frames of the video. Looking at the example shown in FIG. 16, the location of the athlete 110 is determined as it corresponds to the identified rectangle 112 in the environment 82. The rectangle 112 may be identified and transposed through identification of longitudinal and transverse lines in the environment 82 depicted in the frame 84, as described in the preceding section.

To determine the actual physical location of the athlete 110 in a coordinate system associated with the environment 82, a perspective transformation matrix is obtained that includes two sets of points. In FIG. 16, because the polygonal shape that is used is the rectangle 112, each of the two sets of points includes four points. The first set of points corresponds to the vertices, i.e., corners, of the identified rectangle 112 in the environment 82. These are represented as pixel coordinates. The second set of points corresponds to the vertices, i.e., corners, of the rectangle 111 shown in the two-dimensional image 109 that represents the real-dimensions of the environment 82. One corresponding vertex, e.g., the upper left vertex 114 as shown in FIG. 16, may be given coordinates (0,0). To obtain the coordinates of the athlete 110 relative to the rectangle 112, the distance traveled by the athlete 110 between the frames, in pixels, is transformed to real distance using a perspective transformation matrix. For example, knowing the coordinates of the athlete 110 relative to the identified rectangle 112 in the environment 82, displacement along the x-axis and the y-axis in the rectangle 111 in the two-dimensional image 109 can be determined using known distances in the environment 82. The distance over time (e.g., between frames) allows for calculation of athlete speed. To increase the accuracy of speed calculations, all recognized rectangles in the environment 82 may be used, and then results may be averaged. In an alternative aspect, a calibration factor may be used to convert pixel separation, i.e., a number of pixels between locations in a frame, into real world distance (e.g., feet, meters, yards, etc.). The calibration factor may utilize a pixel-to-distance conversion function that takes into account a depth value in a frame.

In certain instances, for a computer-vision system to identify geometric parameters (e.g., height, width, distance, depth, and the like) in frames of a video, it may be necessary to match at least two or more pixel coordinates in an image space with two or more points in real space (e.g., real on-field coordinates). The determination of polygonal shapes in an environment in which the athlete is performing, e.g., on a playing field, allows for determination of such geometric parameters. This information can be interpolated and/or extrapolated to determine other points in the environment as well, for calculation purposes.

In one embodiment, the process of locating and tracking an athlete through a series of frames of a video to determine the athlete's real-time location in a geographic area (e.g., a playing field) is performed by constructing a perspective transformation matrix. The perspective transformation matrix may, in certain aspects, be generated in automated or semi-automated fashion, e.g., using an athlete assessment system, and/or a computer-vision system associated with the same. The perspective transformation matrix may be generated to have a selected number of real-world geographic coordinates, e.g., four coordinates that form a polygonal shape in the environment, e.g., on the playing field. The selected coordinates may be associated with demarcations on the playing field, e.g., boundary lines, distance lines, markers, or other geographic indications. In addition, during analysis, longitudinal and transverse lengths or lines on the playing field may be identified. The longitudinal and/or transverse location of the athlete on the playing field may then be determined, e.g., relative to the demarcations on the field (e.g., lines or other markers that are identified). The athlete's actual physical distance to one or more of the demarcations, e.g., lines, may then be determined using a scale factor. The scale factor may be calculated as a ratio of the distance between identified demarcations, e.g., two lines on the playing field, in pixels of a video frame, as compared to the real-world distance between the identified demarcations, e.g. the two lines on the playing field. In addition, for the purposes of locating the athlete, the distance between the identified demarcations, e.g., the two lines on the playing field, may be calculated as a length of the segment connecting those identified demarcations so that the lowest or most close-to-the-surface point of the athlete's body lies in the segment. This scale factor and associated scaling computation may be utilized in different circumstances for distance calculation and performance data generation as described herein.

Figure 17:
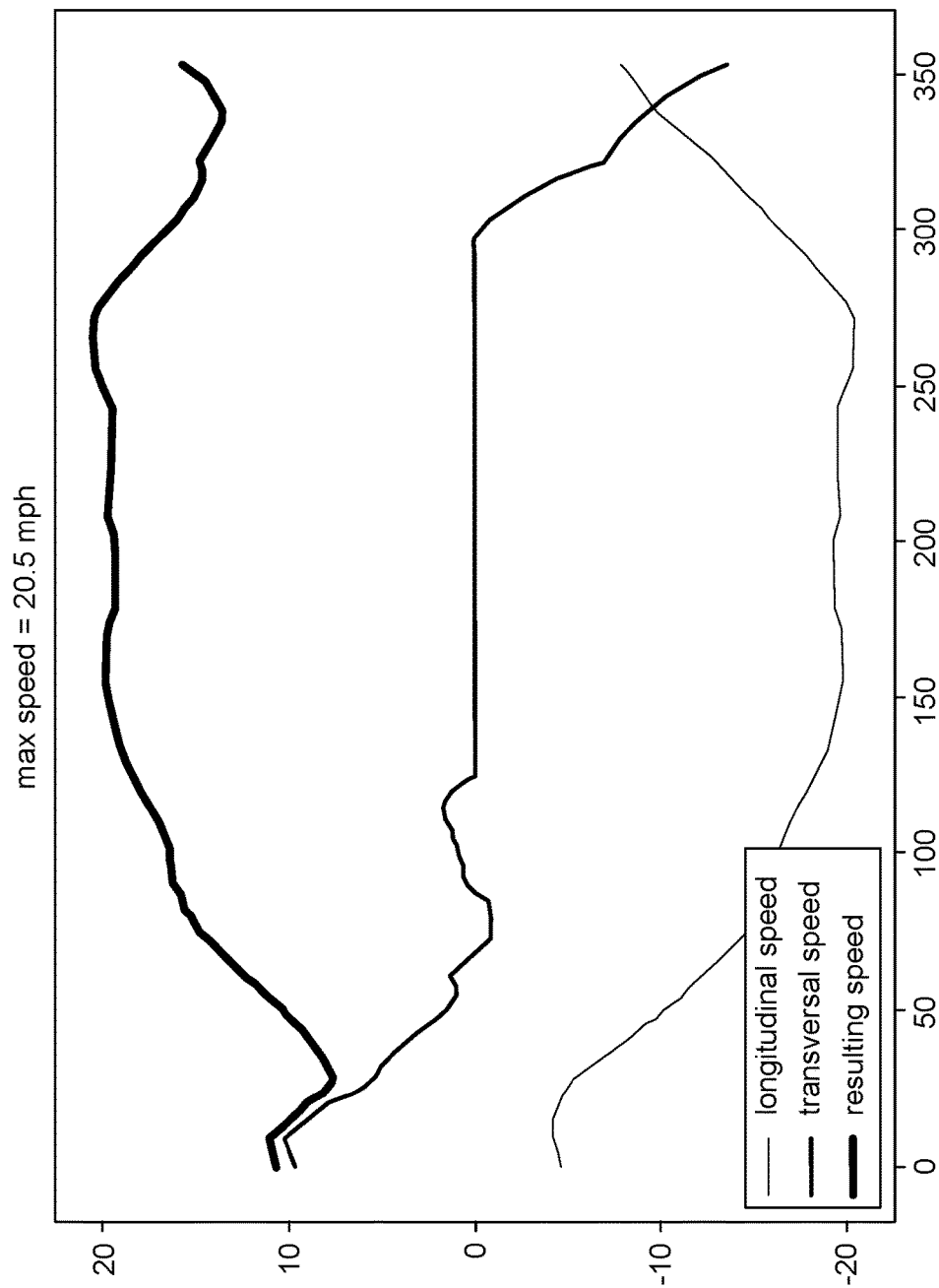
FIG. 17 depicts a graph of an athlete's speed over time, generated using computer-vision analysis, in accordance with an embodiment of the present technology.

Referring now to FIG. 17, a graph of athlete speed over frames of video is depicted, in accordance with an embodiment of the present technology. FIG. 17 in particular depicts a graph of an athlete's maximum speed. When calculating an athlete's maximum speed from frames of video, it may be taken into account that the athlete's speed may be uneven, and that there may be fluctuations in coordinates associated with the athlete in the video, and that there may be some deviation in the recognition of reference elements, e.g., lines on a playing field, in the video. Therefore, a resulting time series of an athlete's displacement may be smoothed using a moving average and also any gaps associated with line recognition due to blurry frames may be resolved using linear interpolation. The calculation of an athlete's speed may be carried out over different time intervals, e.g., 0.1, 0.2, 0.3, 0.5, 0.8, 1, 2, 3, 4, 5, 10, 20, or 30 seconds, among others. The time interval may also correspond to the video frame rate. The longitudinal speed and transverse speed of the athlete that are represented in the graph may be combined to generate a resulting speed as shown in FIG. 17. Further, the total displacement of the athlete, e.g., in pixels, and/or in corresponding physical distance, in the environment in which the athlete is performing may be determined over the particular time interval and then the athlete's speed can be calculated as the ratio of the average displacement per time interval.

Figure 18:
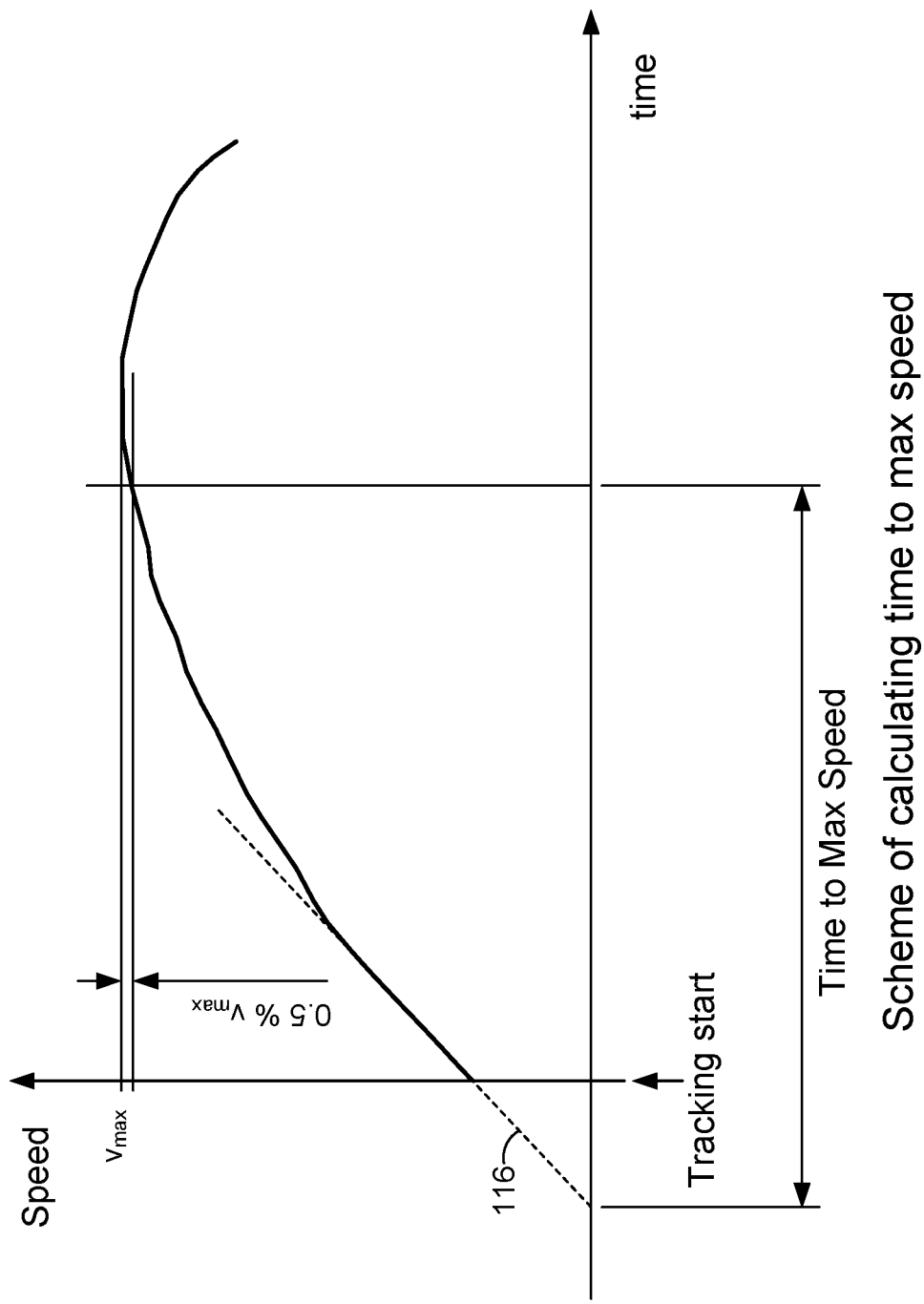
FIG. 18 depicts a graph of an athlete's time to maximum speed, generated using computer-vision analysis, in accordance with an embodiment of the present technology.

FIG. 18 depicts an example calculation of an athlete's time to maximum speed obtained from video analysis, in accordance with an embodiment of the present technology. FIG. 18 depicts a graph of speed versus time for a particular athlete. To calculate the time to maximum speed, a maximum speed of the athlete, e.g., as determined from the process described in connection with FIG. 17, may be determined. In one aspect, the maximum speed may be considered to be obtained by the athlete when the athlete's determined speed differs from the maximum speed by less than 0.1%, 0.3%, 0.5%, or 1%, or another amount. In FIG. 18, the amount is 0.5%. In another aspect, if an athlete has a certain speed already, the time to maximum speed and/or acceleration can be determined by interpolating and/or extrapolating the athlete's speed to zero at the beginning of the time scale, as shown by the portion 116 shown in FIG. 18.

Figure 19:
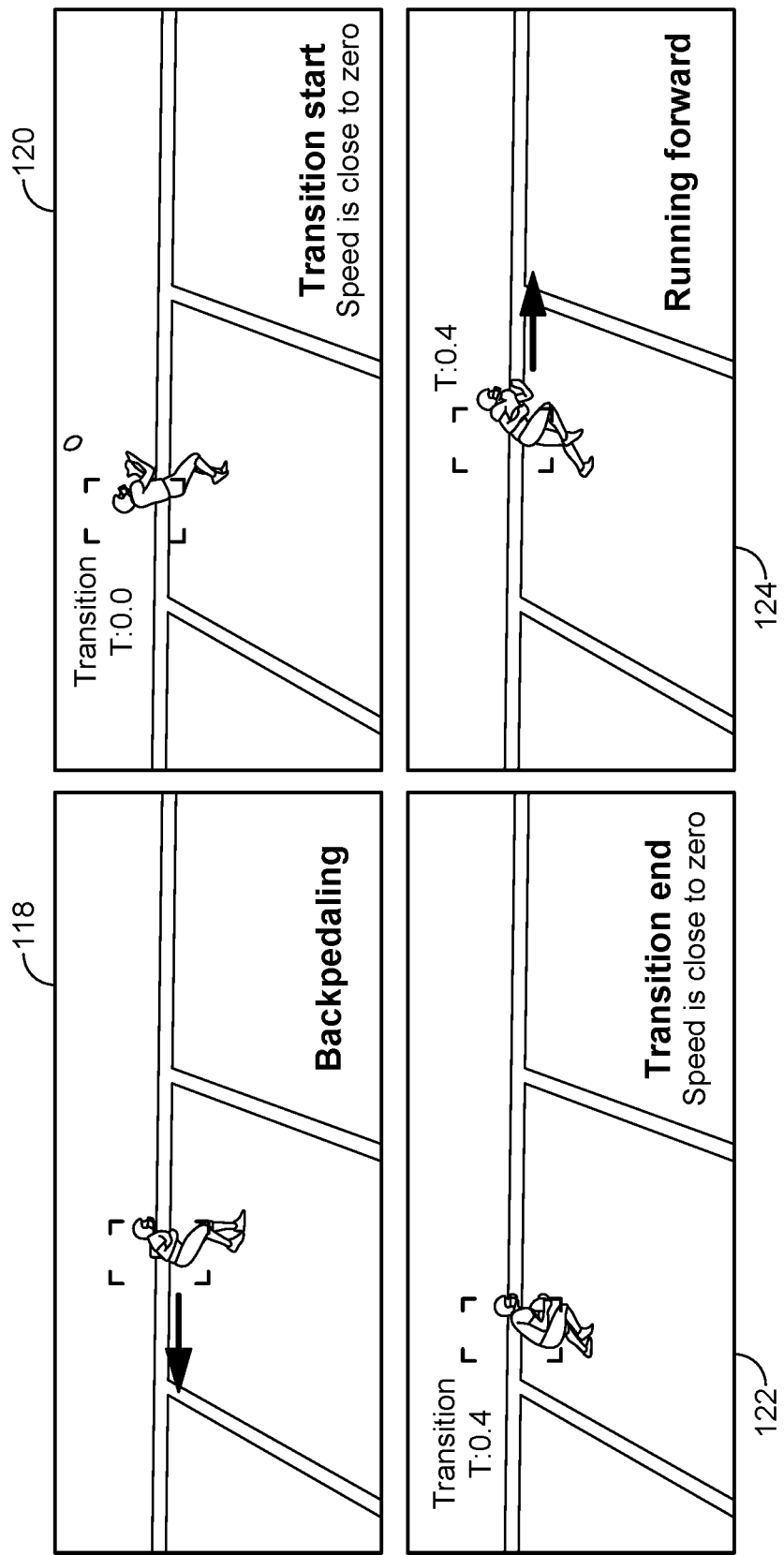
FIG. 19 depicts a frame-by-frame representation of an athlete transitioning, in accordance with an embodiment of the present technology.
Figure 20:
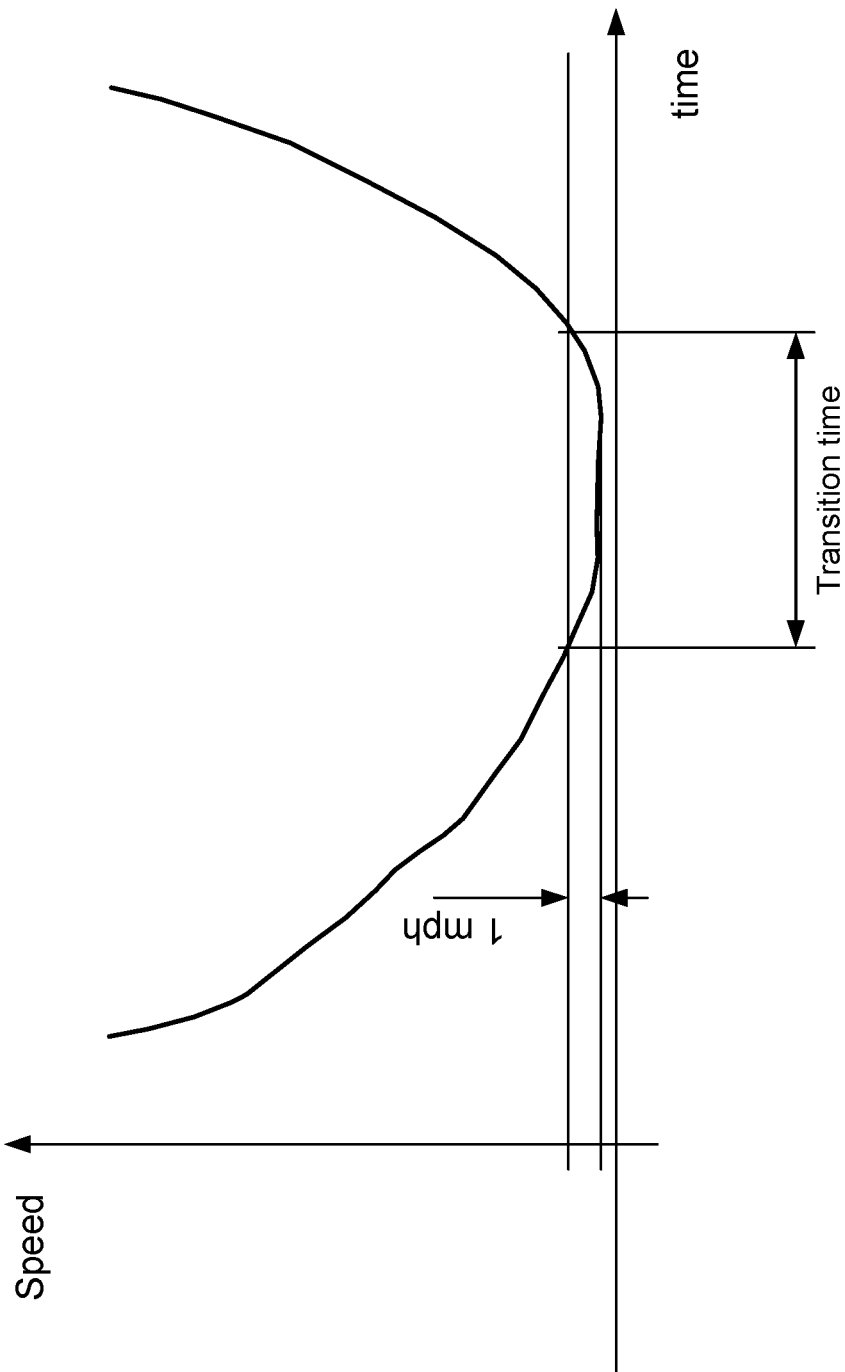
FIG. 20 depicts a graph showing an athlete's transition time, generated using computer-vision analysis, in accordance with an embodiment of the present technology.

FIG. 19 depicts a frame-by-frame example of athlete transition, in accordance with an embodiment of the present technology. To identify an athlete transition, the point in time at which an athlete changes direction of movement in a frame, as indicated by a change in the mathematical sign, is determined. For example, as shown in FIG. 19, initially an athlete may be moving, e.g., backpedaling, in a direction, as shown in the first frame 118 of FIG. 19. The athlete may then begin a transition in direction, e.g., from backpedaling to running forward, as shown in the second frame 120 of FIG. 19. This may be based on the speed of the athlete being close to zero, e.g., in a speed versus time graph, as shown in FIG. 18. The athlete may then complete the transition in direction, e.g., to running forward, as shown in the third frame 122 of FIG. 19. The athlete's speed, acceleration, and other metrics may then also be determined as the athlete continues running forward, as shown in the fourth frame 124 of FIG. 19. FIG. 20 further depicts a graph of speed versus time, identifying a transition time of the athlete on the graph. The identification of the transition may be based on different parameters, but in the example shown in FIG. 20, the athlete's transition time is calculated as the time during which the athlete's speed is less than 1 mile-per-hour ("MPH"), has dropped to zero, and then has reached 1 MPH in a different direction. FIG. 20 identifies the period of time in which this speed window is satisfied, identifying the athlete's transition time according to the 1 MPH base parameter. Other base speeds, such as 0.5 mph, 2 mph, 3 mph, 4 mph, 5 mph, or other speeds may be used as the basis for determining transition time, in different aspects. The transition speed may also be averaged for each athlete over a number of transitions identified by the computer-vision system.

Figure 21:
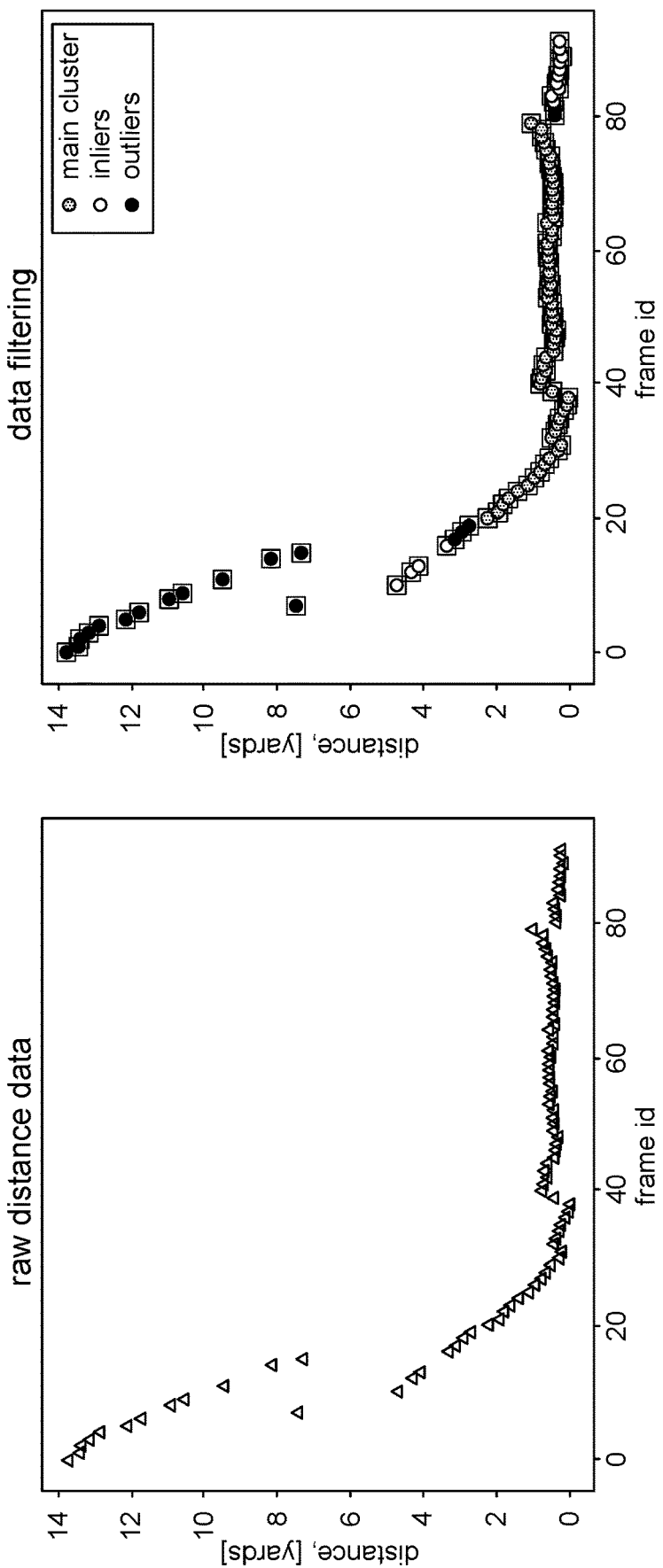
FIG. 21 depicts graphs representing athlete separation, generated using computer-vision analysis, in accordance with an embodiment of the present technology.

Referring now to FIGS. 21-22, examples of filtering distance over frames of video are provided, in accordance with embodiments of the present technology. In certain instances, computer-vision analysis of video frames may not produce smooth distance data due to errors which may occur when identifying reference elements, e.g., lines on a playing field. For example, the tremoring of lines frame-to-frame, lapses or absence of some lines or polygonal shapes, and the like, may contribute to such issues. To filter out incorrect or inconsistent data, a gradients clustering algorithm may be used to identify, and remove, outlier points. FIG. 21 shows two graphs each providing athlete distance per frame of video, with main data and outlier data represented. To remove outlier data points, a gradients clustering algorithm, or another method, may be used to identify and remove the outliers. FIG. 22 shows similar graphs with outlier data points having been removed, and with the remaining data points being smoothed using polynomial curve fitting and the least squares method.

Referring now to FIG. 23, an example analysis for determining athlete closing speed is provided, in accordance with an embodiment of the present technology. To calculate athlete closing speed, once again, the athlete location and distance calculations described herein are utilized. In addition, to recognize a closing event, e.g., an event in which an athlete closes the distance to another athlete or object, different criteria may be utilized by the computer-vision system. For example, an overlapping 115 of separate tracking designators 113 (e.g., tracking or bounding boxes) that are tagged to, or associated with, individual athletes may be utilized; the distance (e.g., in pixels) between tracking designators 113 (e.g., tracking or bounding boxes) that are tagged to, or associated with, individual athletes may be utilized; and/or the determined physical distance between athletes (e.g., in feet, yards, meters, etc.) may be utilized. In instances in which closing speed is determined based on tracking boxes overlapping, the following equation may be used:

$$\overline{A} = \frac{A_{overlapped}}{\min\{A_1, A_2\}},$$

where $A_1$ is the area of the first athlete's tracking designator, $A_2$ is the area of the second athlete's tracking designator, and $A_{overlapped}$ is the area of overlap of the tracking designators. In instances in which the distance 117 between the tracking designators 113 is utilized, the following equation may be used:

$$\overline{d} = \frac{\text{distance}}{\min\{d_1, d_2\}}$$

where $d_1$ is a geometric shape associated with at least part of the tracking designator of the first athlete, e.g., a diagonal line 119 across a tracking box 121 around the first athlete, and $d_2$ is a geometric shape associated with at least part of the tracking designator of the second athlete, e.g., a diagonal line 123 across a tracking box 125 around the second athlete, and "distance" is the distance between the geometric shapes, e.g., the distance 117 between the centers of the tracking boxes 121, 125 around the first and second athletes. This distance, as noted above, may be a pixel distance and/or may be a physical distance determined from frame analysis (e.g., using a transformation matrix and/or calibration or conversion factor).

Figure 24B:
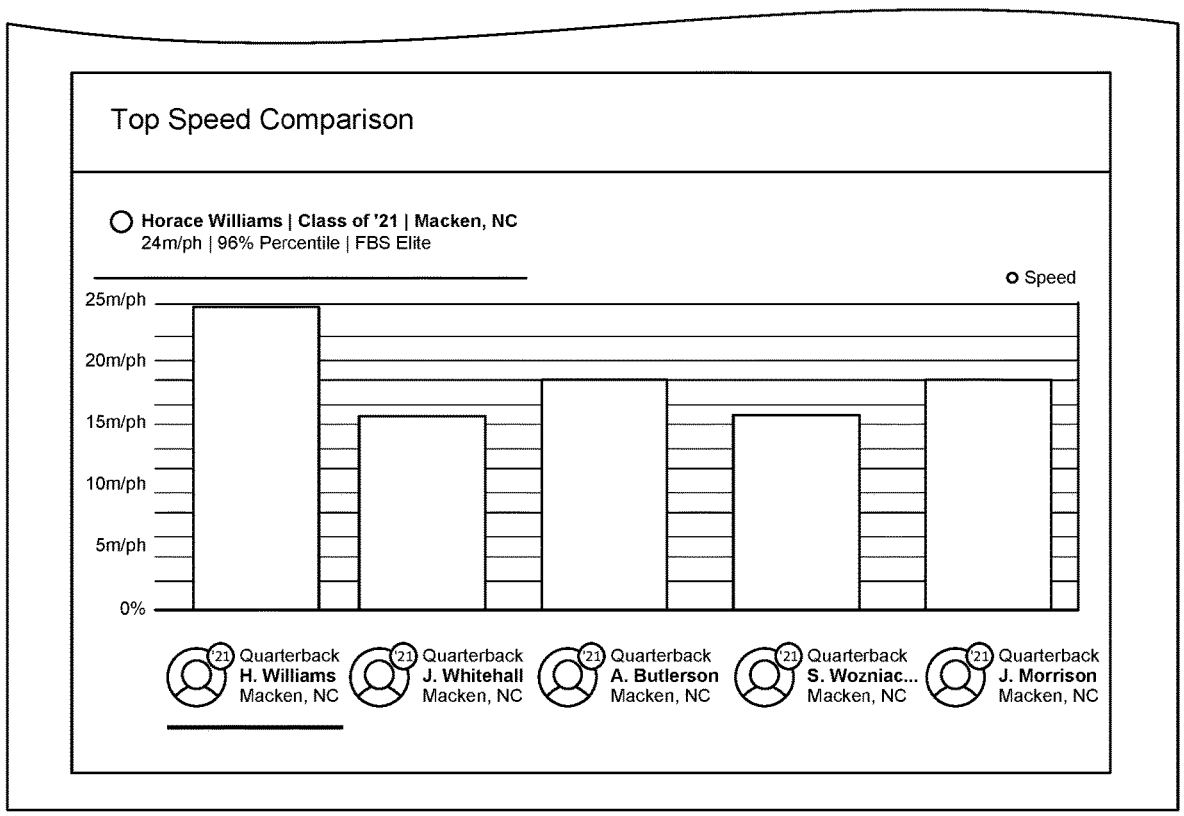

Referring now to FIG. 24, an example user-interface 126 associated with a technology platform used for athlete assessment and/or recruitment is provided, in accordance with an embodiment of the present technology. The user-interface 126 may be utilized with embodiments described herein, and includes a selection of features, including user-modifiable settings 128 for refining an athlete search, and generating top athlete prospects (e.g., for recruitment). The user-interface 126 allows different athlete parameters (e.g., film grade, athleticism score, name, classification, sport, position, or the like) to be selected for use in initiating and refining an athlete search. The user-interface 126 in FIG. 24 also depicts a plurality of generated athlete prospects 130, which may be presented based on a best-fit match between the selected parameters and the athlete's performance data. The user-interface 126 further presents a plurality of under-recruited athletes 132. These athletes 132 may represent candidates matching, to some threshold degree, the selected parameters, but have not yet been recruited, or have been recruited less than other athletes by a minimum amount, indicating a higher possibility of successful recruitment. The user-interface 126 may be modifiable and/or customizable, in different aspects. FIG. 24 also depicts a selection of athletes 134 at the bottom of the user-interface 126 that are compared based on a particular metric, which in this instance, is top speed. As shown in FIG. 24, each athlete's name, top speed, location, and position, among other possible data representations, are shown. The data used to generate the user-interface 126 may be generated, compiled, and/or transformed using the technology described herein.

Figure 25B:

Referring now to FIG. 25, the user-interface 126 of FIG. 24 with different information presented is shown, in accordance with an embodiment of the present technology. In particular, FIG. 25 depicts the user-interface 126 showing, or categorizing, identified athletes based on their social engagement, e.g., social media activity. In particular, the user-interface 126 depicts notable, or significant, social media activity 136 of the athletes 130, 132 at the bottom of FIG. 25.

Figure 26:
FIG. 26 depicts another user-interface associated with a technology platform used for athlete assessment and/or recruiting and/or scouting, in accordance with an embodiment of the present technology.

Referring now to FIG. 26, another user-interface 138 associated with a technology platform used for athlete assessment and/or recruitment is provided, in accordance with an embodiment of the present technology. The user-interface 138 shown in FIG. 26 allows for numerous user-modifiable parameters to be adjusted, allowing athletes analyzed using the technology described herein to be identified based on best-fit matches with the selected parameters. For example purposes, user-modifiable parameters such as athlete classification, offers, film grade, sport position, ratings (e.g., star ratings), vertical jump, academic characteristics (e.g., SAT score), sprint time (e.g., 40-yard dash and short-shuttle), height, weight, GPA minimum, geographic region or location, and the like may be included and selectable or modifiable for athlete search and refinement purposes.

Figure 27:
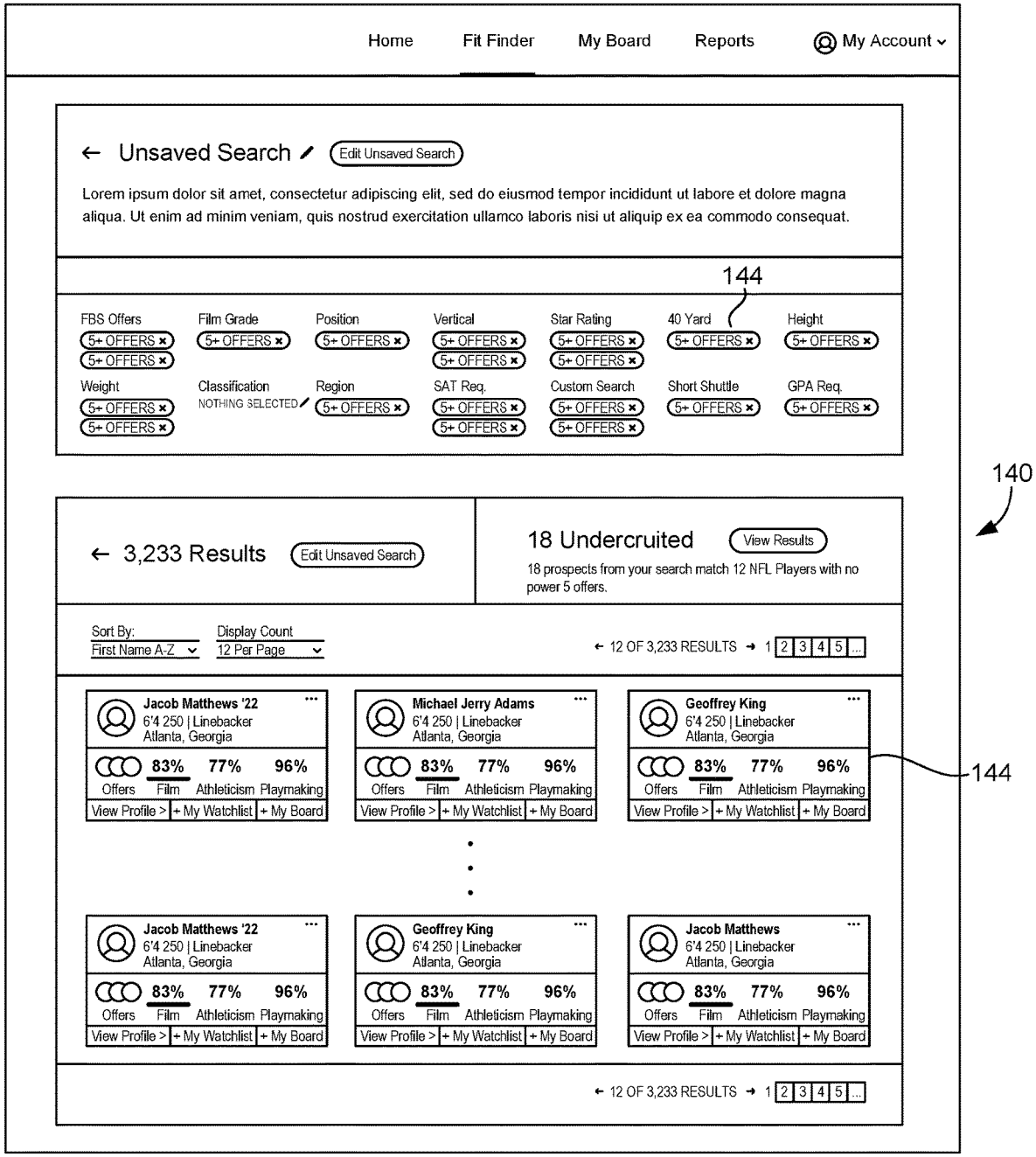
FIG. 27 depicts another user-interface associated with a technology platform used for athlete assessment and/or recruiting and/or scouting, in accordance with an embodiment of the present technology.

Referring now to FIG. 27, a user-interface 140 associated with a technology platform used for athlete assessment and/or recruitment is provided, in accordance with an embodiment of the present technology. FIG. 27 in particular depicts generated athlete matches 144 that have been refined based on the user-selected search parameters 142, with percentage matches being provided for certain categories. In addition, along with each identified athlete, a selection of characteristics are shown, e.g., offers (e.g., college, franchise, institution, or the like), film grade (e.g., how closely the athlete's film matched the user-selected parameters), athleticism (e.g., based on a score determined from weighted combinations of different athlete attributes such as the athlete's maximum speed, maximum acceleration, transition time, closing speed, and/or other characteristics, and/or any combination thereof), in addition to each athlete's name, height, weight, position, and geographic location. Different selections of displayed information and data are possible in different aspects as well. This refinement, and presentation, of athletes may be generated based on performance data obtained for the athletes through computer-vision analysis of athlete video (e.g., practice or game film), allowing the process of identifying suitable athlete candidates and recruiting them to be performed more quickly, efficiently, and with greater precision.

Referring now to FIG. 28, a user-interface 146 associated with a technology platform used for athlete assessment, scouting, evaluation, and/or recruiting is provided, in accordance with an embodiment of the present technology. The user-interface 146 shown in FIG. 28 in particular is presenting comparisons of athletes at different levels, e.g., high school, college, or professional level. One comparison example is "undercruited" or "under-recruited" athletes, e.g., athletes that are identified as being suitable, desirable, or ideal prospects based on the parameters selected for the search, but that have comparatively fewer, or no, offers to join schools, teams, or organizations, or the like, thereby enhancing their status as a prospect. In other embodiments, in addition to "undercruited" athletes, other types of athlete comparisons and recommendations may be presented, e.g., those specific to high school, college, or professional organizations. For example, recommendations for best athlete (e.g., all conference high school or college athlete) or best starter (e.g., in a high school, college, or professional league), or best playoff athlete (e.g., in a high school, college, or professional sport), or the like, may be presented as well.

Figure 29B:
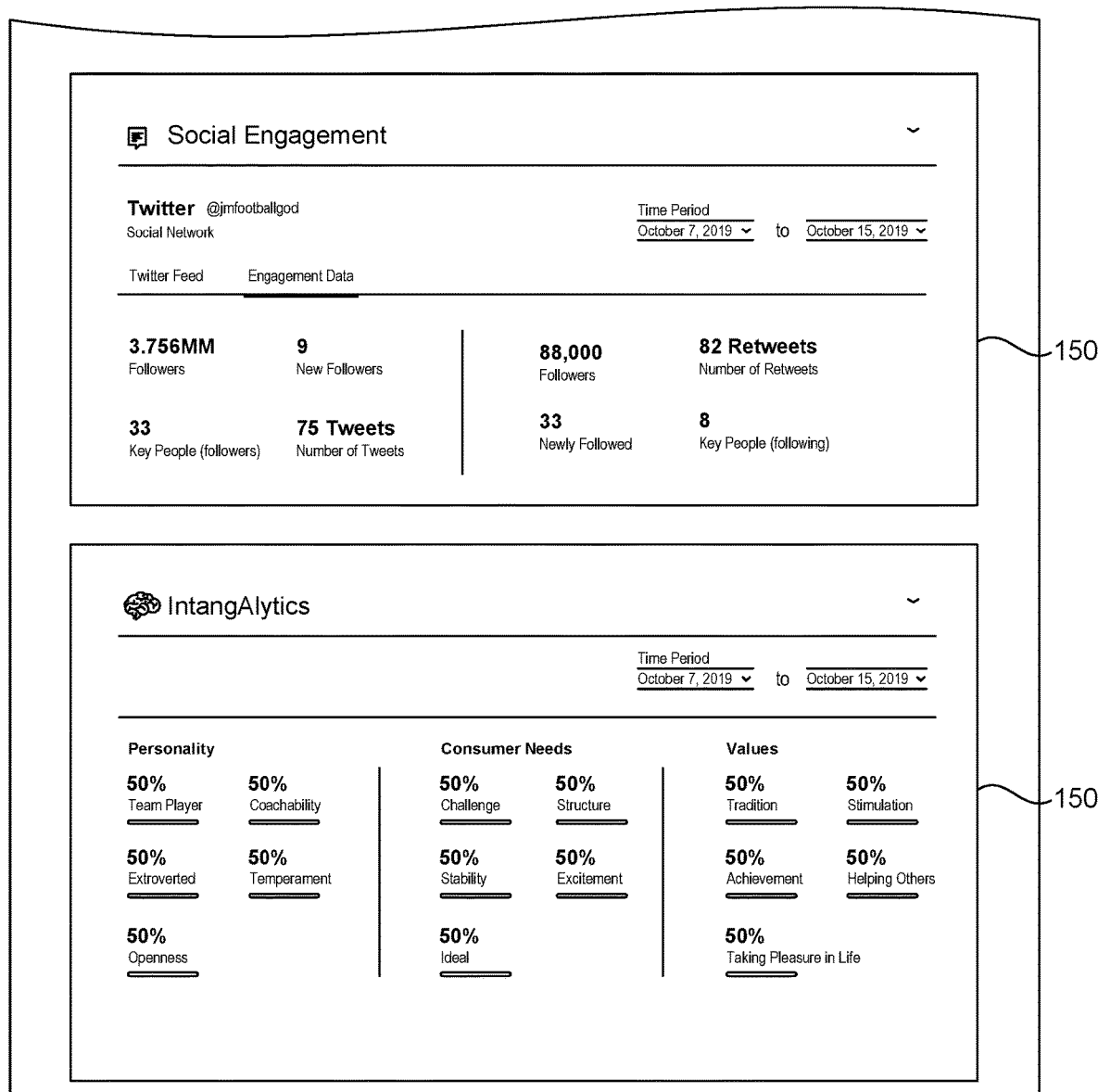

Referring now to FIG. 29, another user-interface 148 associated with a technology platform used for athlete assessment and/or recruitment is provided, in accordance with an embodiment of the present technology. FIG. 29 in particular shows a profile 150 for an athlete 152. The profile 150, as shown in FIG. 29, provides performance data for a high-school athlete, e.g., for the purposes of analyzing the athlete for recruitment for a college organization. The profile 150 further includes athlete data, some of which may be generated and/or compiled using the technology described herein. For example, the profile 150 depicted in FIG. 29 includes athlete details such as class, sport, position, height, weight, offers, and visits to recruiting organizations. The profile 150 further includes athlete performance data which may be generated using the technology described herein and includes, e.g., maximum speed, transition time, closing speed and/or time, time to top speed, average play completion rate, average separation, catch rate, and average yards after catch completion, explosive plays allowed, and other data. In addition, the profile includes social engagement information, e.g., social media information, such as number of followers on a particular social media platform, new followers, number of notable followers, number of posts, and the like, including over a particular time period. The profile 150 further includes data on intangible aspects of the athlete, such as personality, which may be obtained from different objective and subject sources. The profile 150 also includes rankings for characteristics such as team player, coachability, extrovert, introvert, temperament, and openness. The intangible aspects may further include athlete needs, such as challenge, structure, stability, excitement, and idealness. The intangible aspects of the profile 150 may further include athlete values, such as tradition, stimulation, achievement, helping others, and taking pleasure in life, in addition, to provide a more comprehensive picture of the candidate athlete.

Figure 30:
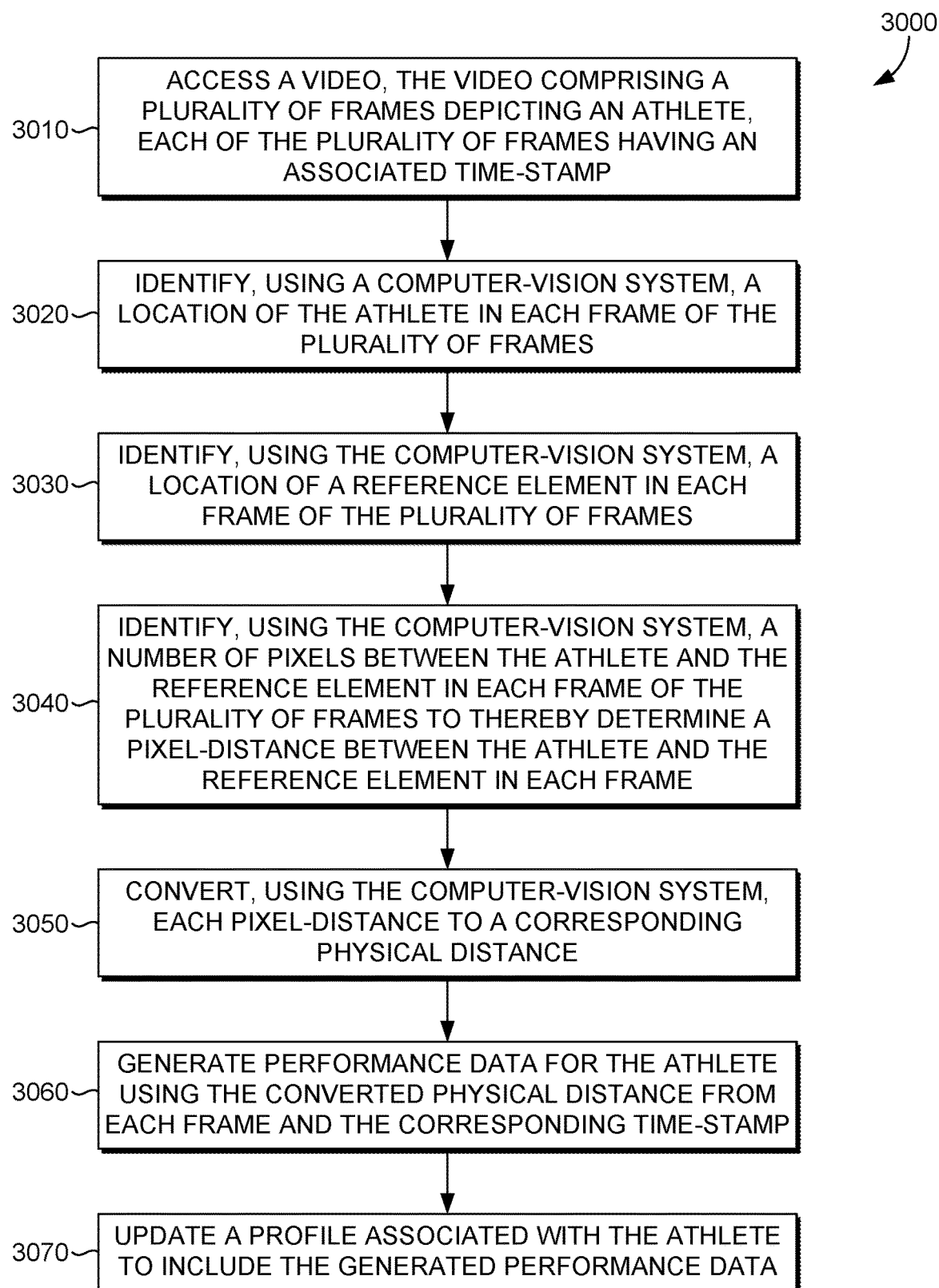
FIG. 30 depicts a block diagram of a method of generating athlete performance data using computer-vision analysis, in accordance with an embodiment of the present technology.

FIG. 30 depicts a block diagram of a method 3000 of generating athlete performance data using computer-vision analysis, in accordance with an embodiment of the present technology. The method is represented by blocks 3010-3070. At block 3010, the method includes accessing a video, the video comprising a plurality of frames depicting an athlete, each of the plurality of frames having an associated time-stamp. At block 3020, the method includes identifying, using a computer-vision system, a location of the athlete in each frame of the plurality of frames. In one aspect, the athlete location may be associated with a designator, e.g., a tag, bounding box, or other indicator. At block 3030, the method includes identifying, using the computer-vision system, a location of a reference element in each frame of the plurality of frames. In different aspects, the reference elements may be fixed, e.g., being geometric fixtures or markers, such as lines, or may be movable, e.g., being other athletes. At block 3040, the method includes identifying, using the computer-vision system, a number of pixels between the athlete and the reference element in each frame of the plurality of frames to thereby determine a pixel-distance between the athlete and the reference element in each frame. At block 3050, the method includes converting, using the computer-vision system, each pixel-distance to a corresponding physical distance using a conversion process. In different aspects, this may be performed using a calibration factor, and/or a transformation matrix, as described herein. At block 3060, the method includes generating performance data for the athlete using the converted physical distance at each time-stamp. At block 3070, the method includes updating a profile associated with the athlete to include the generated performance data.

Figure 31:
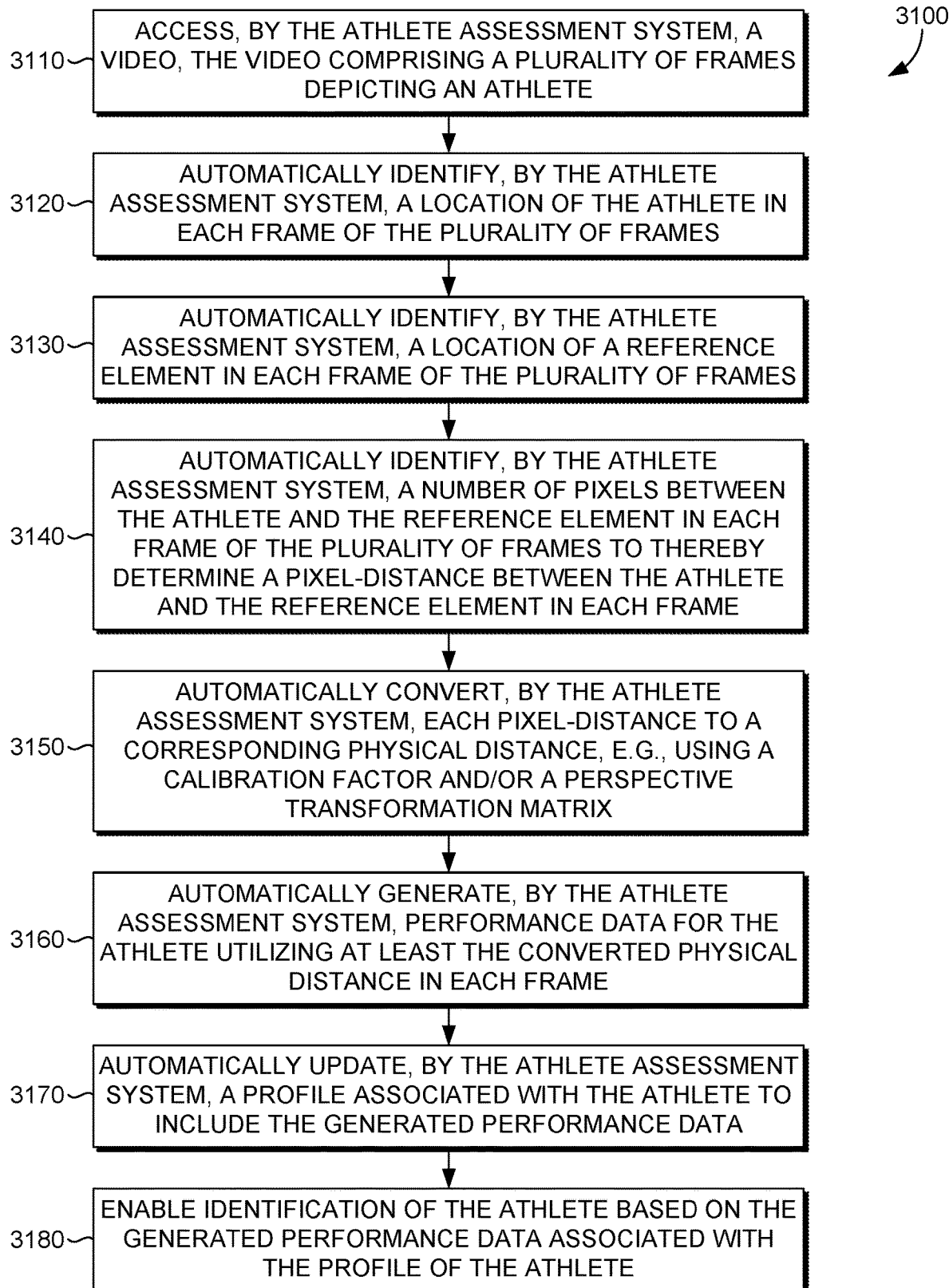
FIG. 31 depicts a block diagram of a method for generating athlete performance data in automated or semi-automated fashion using an athlete assessment system, in accordance with an embodiment of the present technology.

FIG. 31 depicts a block diagram of a method 3100 for generating athlete performance data in automated or semi-automated fashion using an athlete assessment system, in accordance with an embodiment of the present technology. The method is represented by blocks 3110-3180. At block 3110, the method includes accessing, by the athlete assessment system, a video, the video comprising a plurality of frames depicting an athlete. At block 3120, the method includes automatically identifying, by the athlete assessment system, a location of the athlete in each frame of the plurality of frames. At block 3130, the method includes automatically identifying, by the athlete assessment system, a location of a reference element in each frame of the plurality of frames. At block 3140, the method includes automatically identifying, by the athlete assessment system, a number of pixels between the athlete and the reference element in each frame of the plurality of frames to thereby determine a pixel-distance between the athlete and the reference element in each frame. At block 3150, the method includes automatically converting, by the athlete assessment system, each pixel-distance to a corresponding physical distance, e.g., using a calibration factor and/or a perspective transformation matrix and/or a scale factor. At block 3160, the method includes automatically generating, by the athlete assessment system, performance data for the athlete utilizing at least the converted physical distance in each frame. At block 3170, the method includes automatically updating, by the athlete assessment system, a profile associated with the athlete to include the generated performance data. At block 3180, the method includes enabling identification of the athlete based on the generated performance data associated with the profile of the athlete.

Figure 32:
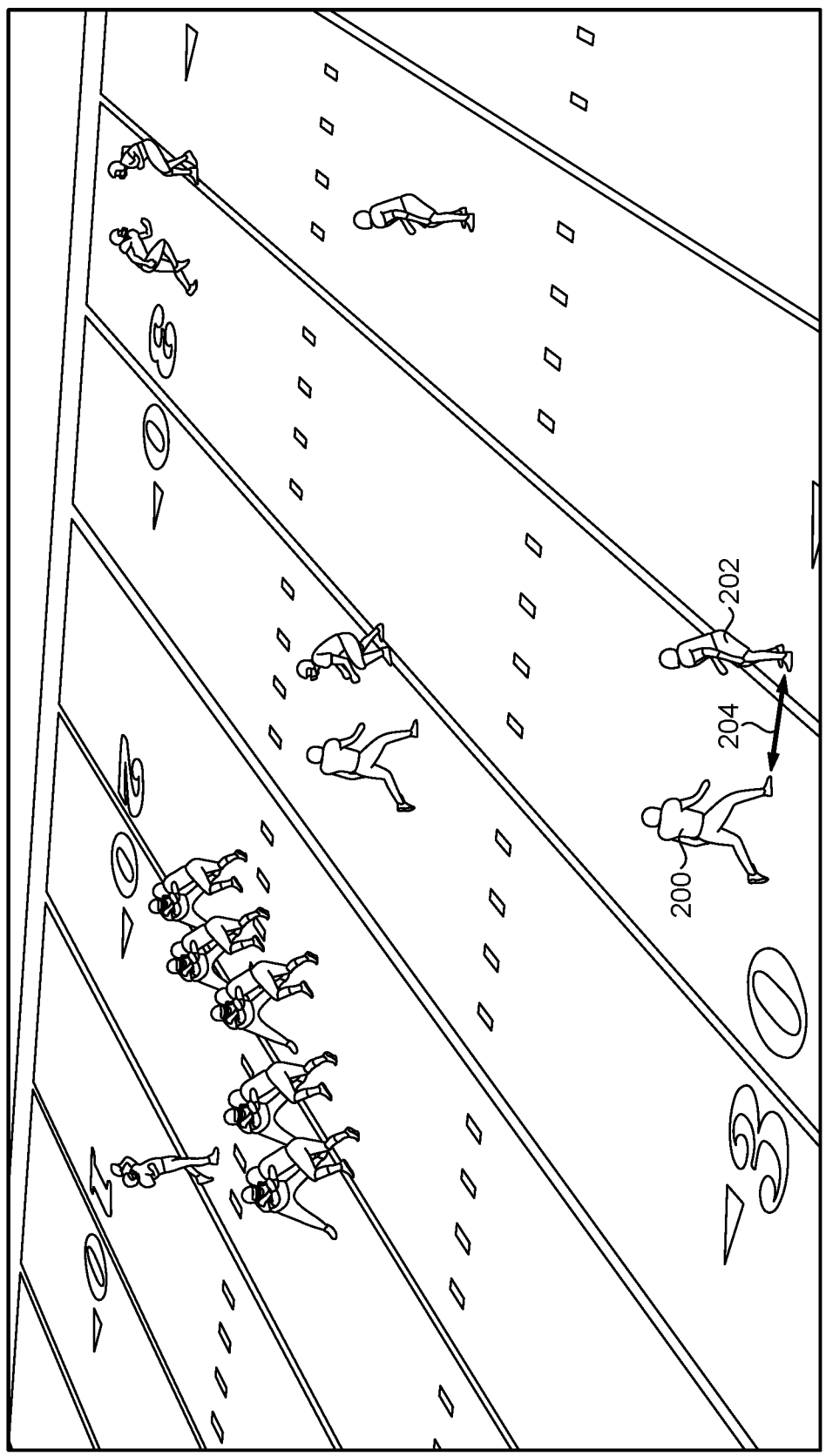
FIG. 32 depicts part of a computer-vision analysis used to determine separation distance between athletes, in accordance with an embodiment of the present technology.

FIG. 32 depicts part of a computer-vision analysis used to determine a separation distance between athletes under different circumstances, in accordance with an embodiment of the present technology. In particular, FIG. 32 depicts how, using a computer-vision system, the location of an offensive athlete 200 can be identified, and the location of a defensive athlete 202 can be identified, and then using the locating processes described herein, the pixel distance 204 between the athletes 200, 202 can be determined, from which a corresponding real-world distance can be determined. To provide one example, in football, a distance, e.g., in yards, between a quarterback and a nearest defender at the time a ball is thrown by the quarterback may be determined. The identified separation distance 204 shown in FIG. 32 may be used to generate performance data and update profiles of the athletes 200 and/or 202. This may enable assessment of certain athletes in particular, e.g., those that catch a ball during gameplay (e.g., wide receivers in football, among others).

Figure 33A:
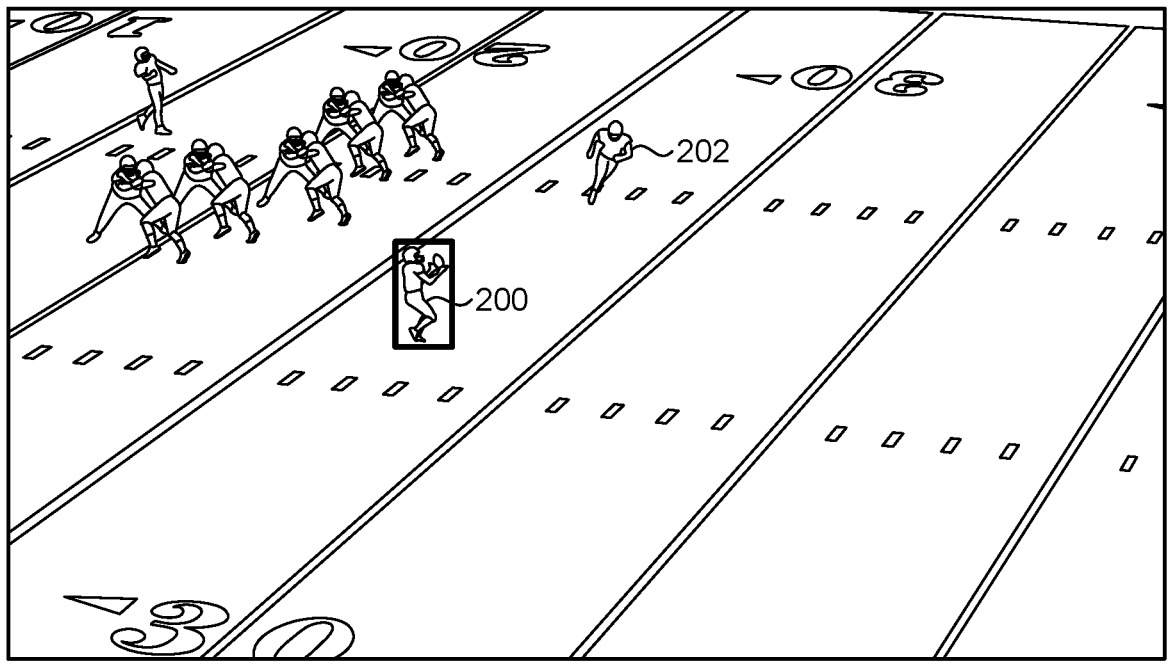
FIGS. 33A-33B depict part of a computer-vision analysis used to determine distance after catch completion, in accordance with an embodiment of the present technology.
Figure 33B:
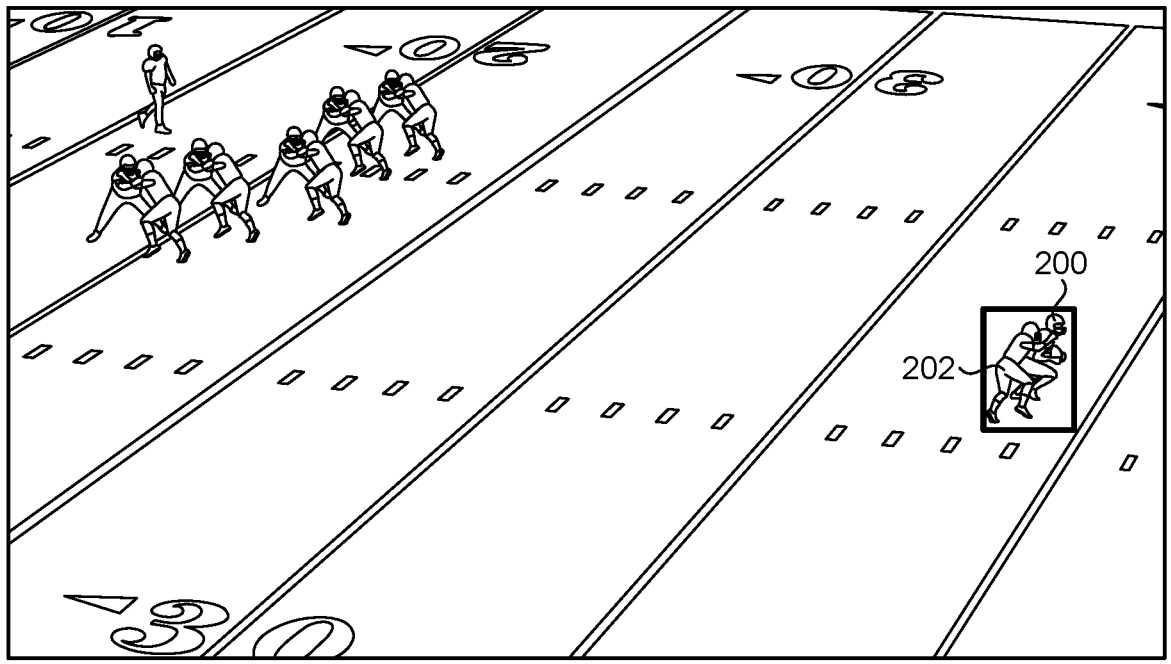

FIGS. 33A-33B depict part of a computer-vision analysis used to determine a distance traveled by an athlete after completing a catch, in accordance with an embodiment of the present technology. FIG. 33A depicts a video frame at which the athlete 200 catches a ball, e.g., a football, as shown in FIG. 33A. FIG. 33B depicts a subsequent video frame in which another athlete 202 has reached the athlete 200 to stop the play. The distance between the location of the athlete 200 in the frame shown in FIG. 33A and the location of the athlete 200 in the frame shown in FIG. 33B can then be determined using the distance calculating processes described herein to determine the distance traveled by the athlete 200 after completing the catch. This distance data may be used to generate performance data for the athletes 200 and/or 202, which can be used for assessment of certain athletes, e.g., those that catch a ball during gameplay (e.g., wide receivers in football, among others).

Figure 34A:
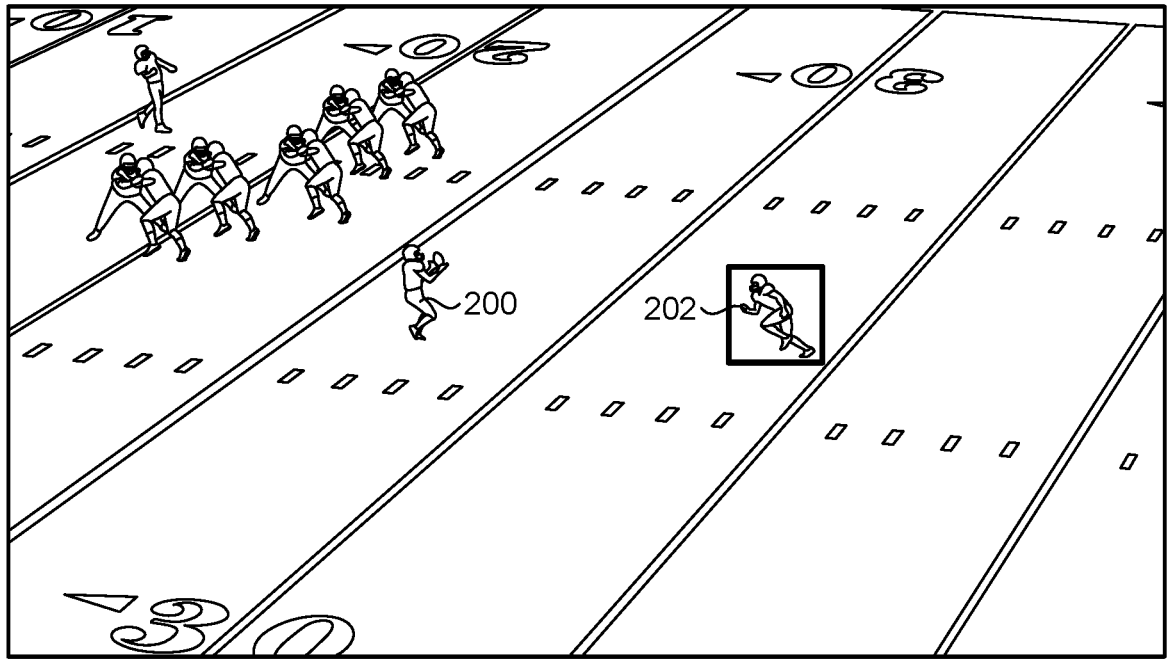
FIGS. 34A-34B depict part of a computer-vision analysis used to determine athlete closing time, in accordance with an embodiment of the present technology.
Figure 34B:
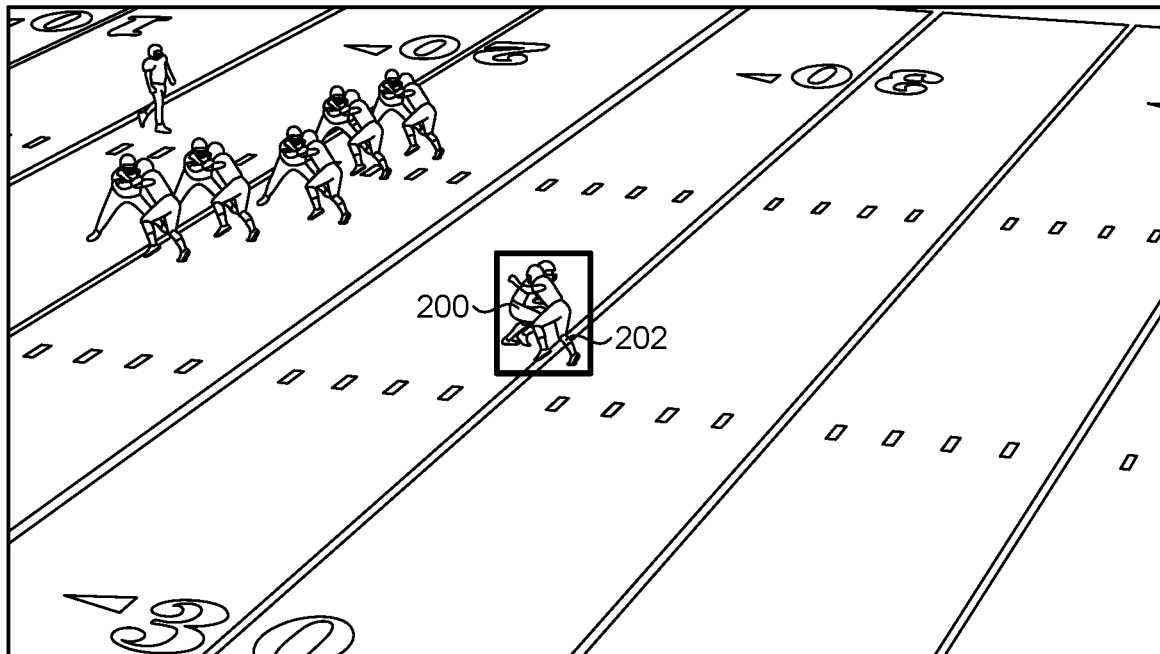

FIGS. 34A-34B depict part of a computer-vision analysis used to determine athlete closing time, in accordance with an embodiment of the present technology. FIG. 34A depicts a point in time at which an athlete 200 catches a ball, but instead with a location of the athlete 202 identified for tracking purposes. The tracking of the athlete 202 may begin once the athlete 202 begins closing on the other athlete 200 with the ball. The athlete 202 depicted in FIGS. 34A-34B represents for the purposes of explanation a defensive athlete. The distance between the athletes 200, 202 in each frame of video may be determined until it is determined that the athlete 202 has closed the distance with the athlete 200 as shown in FIG. 34B. From this, the time required for the athlete 202 to close the distance to the athlete 200 can be determined. This may be used to generate performance data for the athletes 200 and/or 202, e.g., a closing speed, acceleration, or time to close the distance between the athletes 200, 202. This performance data may be used for assessment of certain athletes, e.g., defensive athletes (e.g., defensive backs in football).

Figure 35A:
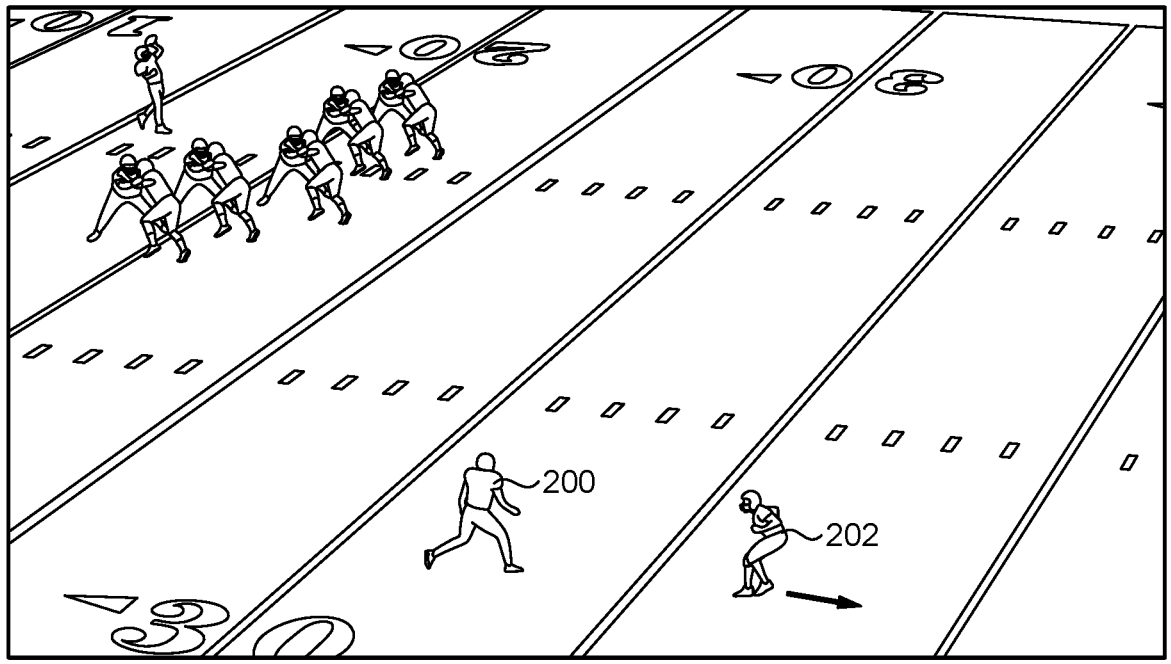
FIGS. 35A-35B depict part of a computer-vision analysis used to determine one aspect of athlete transition time, in accordance with an embodiment of the present technology.
Figure 35B:
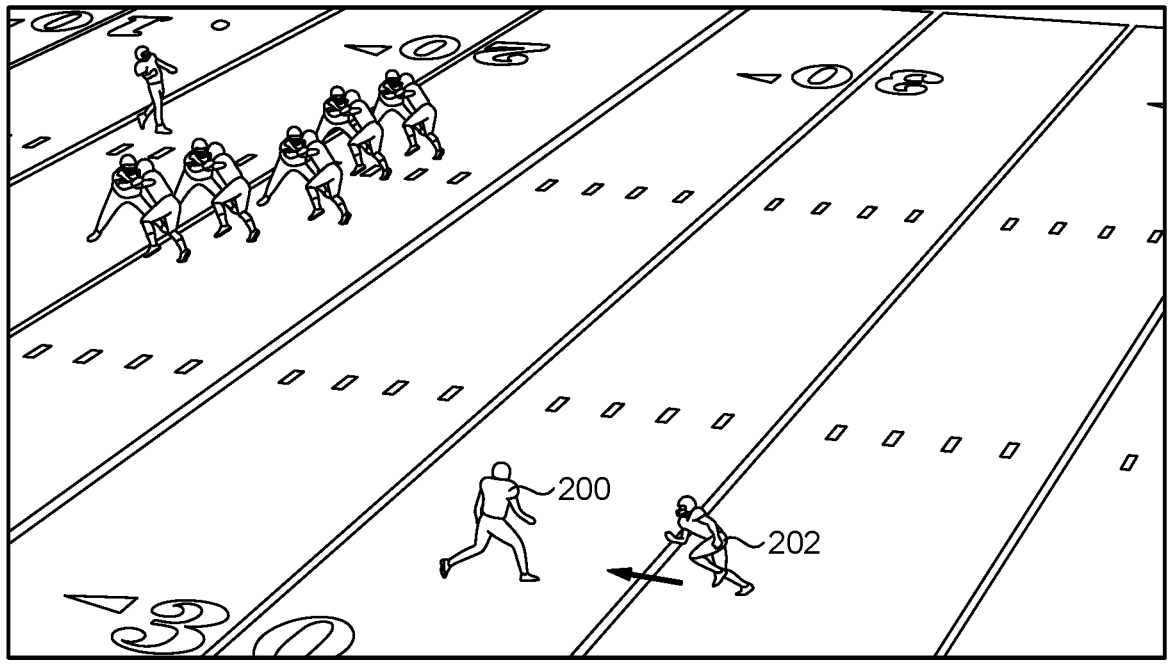
Figure 36A:
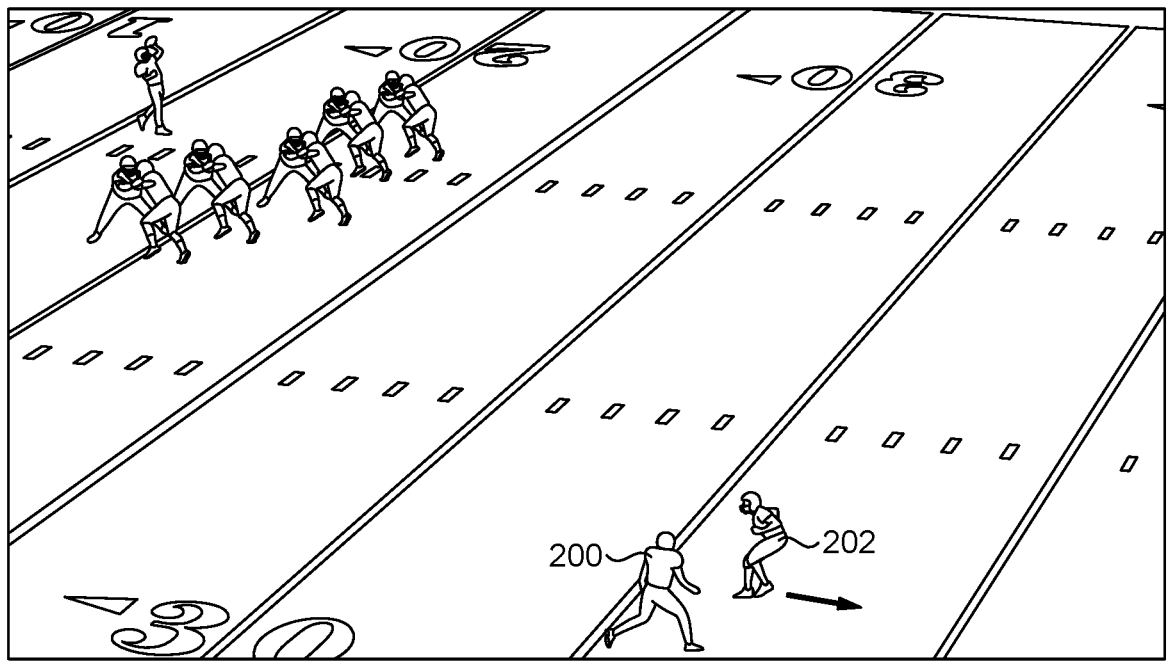
FIGS. 36A-36B depict part of a computer-vision analysis used to determine another aspect of athlete transition time, in accordance with an embodiment of the present technology.
Figure 36B:
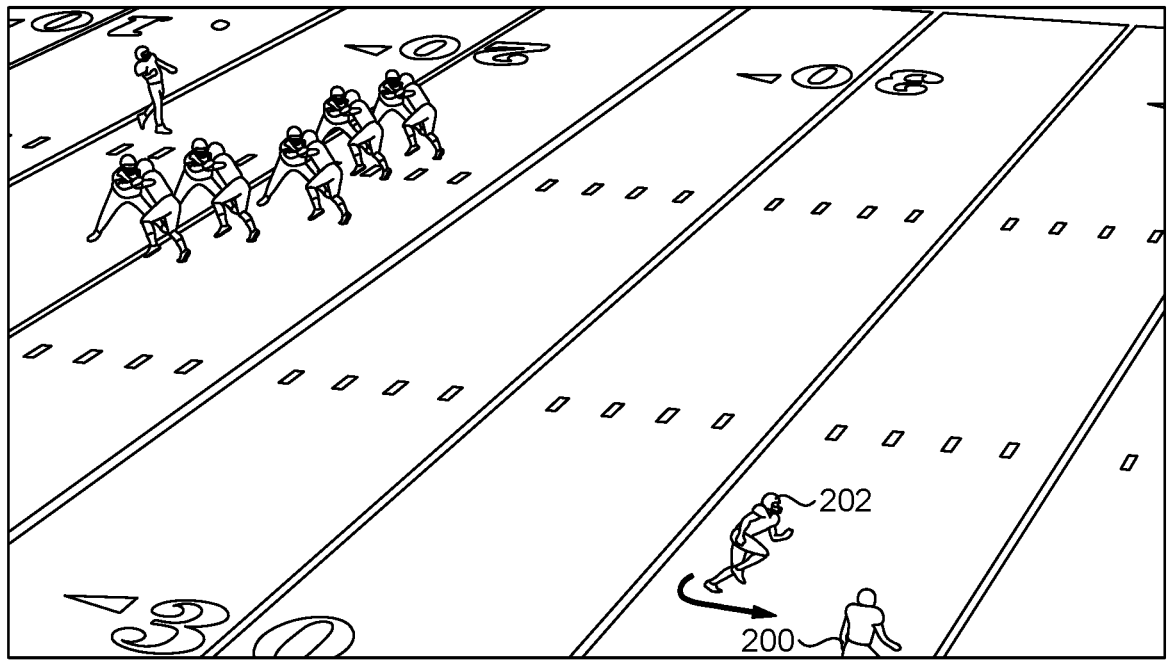
Figure 37A:
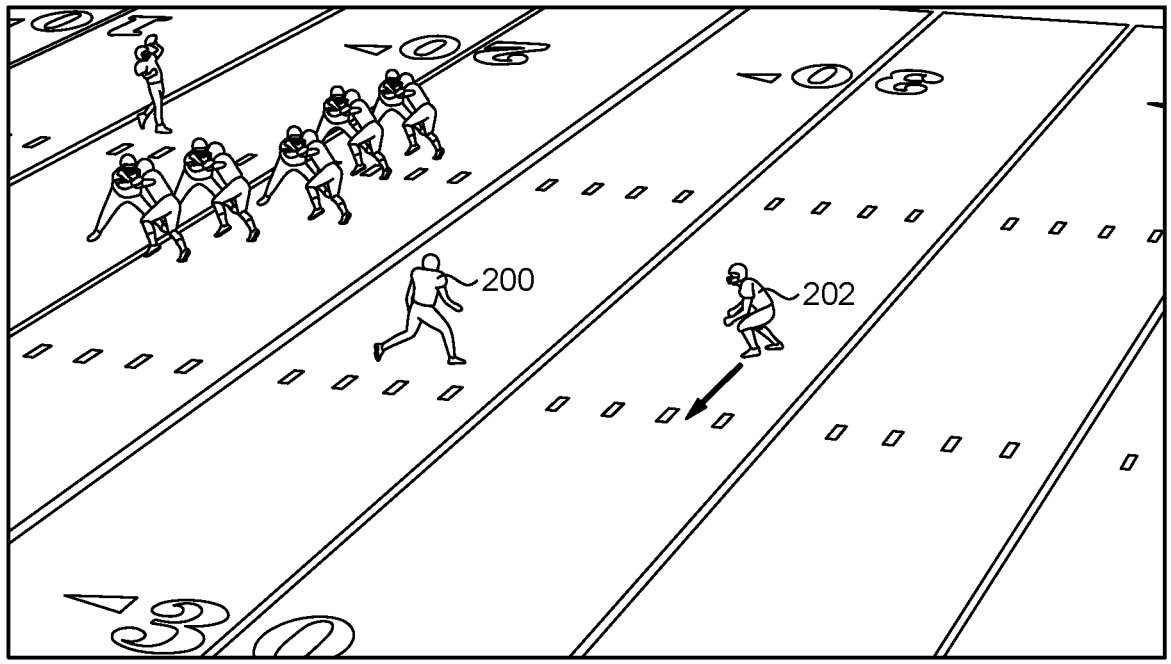
FIGS. 37A-37B depict part of a computer-vision analysis used to determine another aspect of athlete transition time, in accordance with an embodiment of the present technology.
Figure 37B:
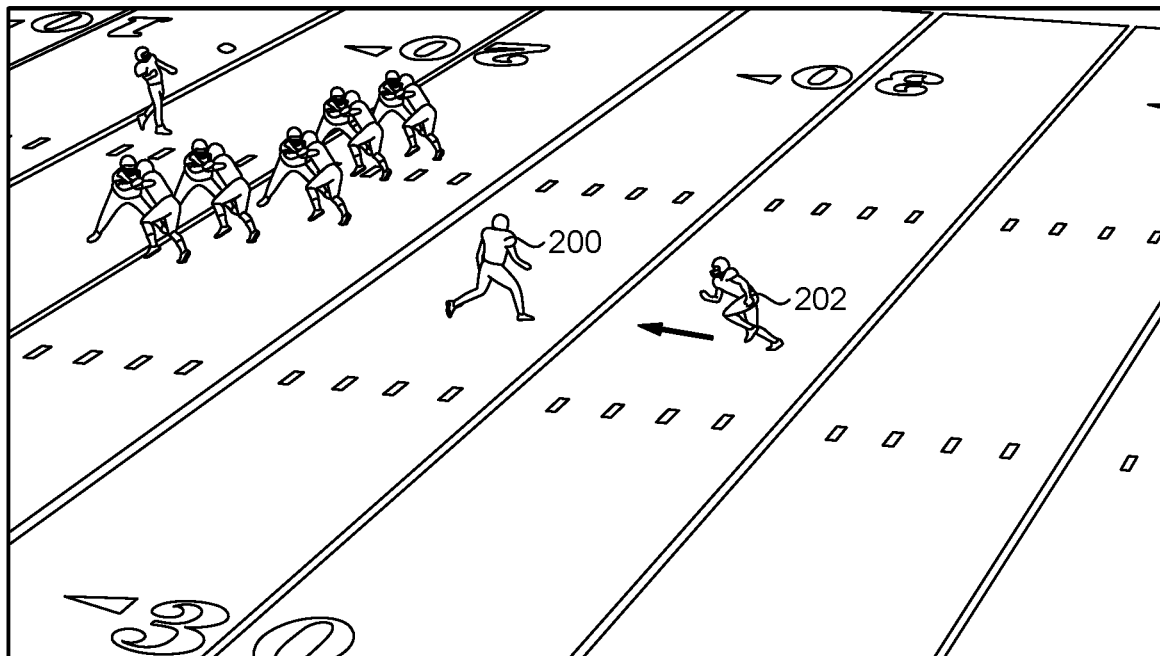
Figure 38A:
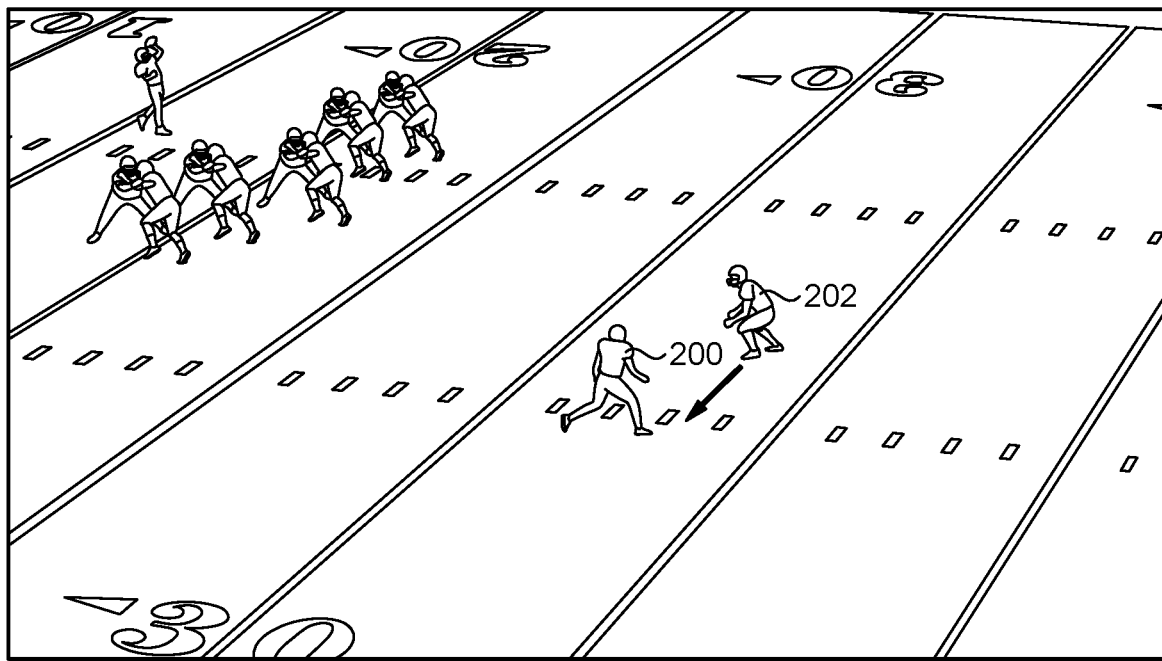
FIGS. 38A-38B depict part of a computer-vision analysis used to determine another aspect of athlete transition time, in accordance with an embodiment of the present technology.
Figure 38B:
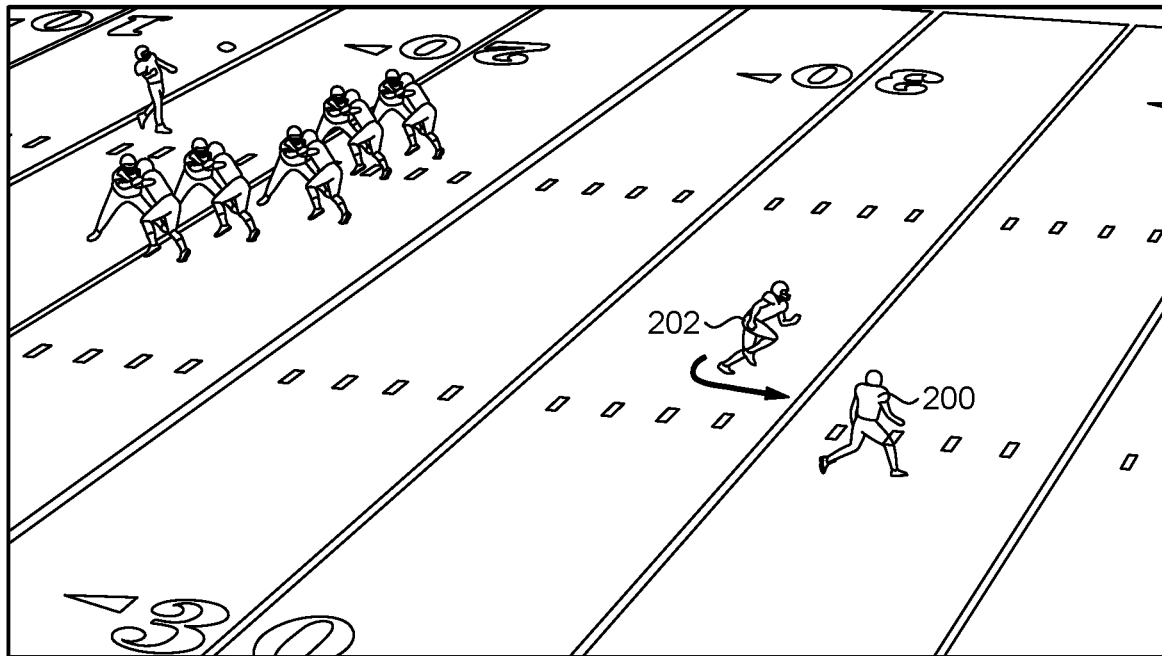
Figure 39A:
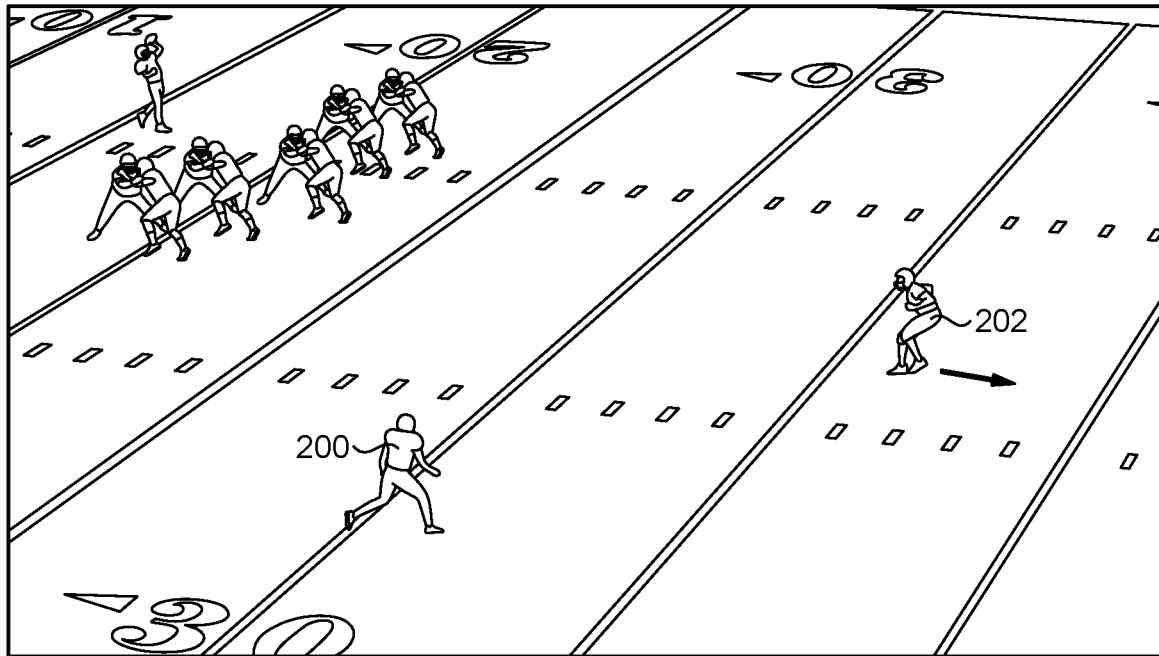
FIGS. 39A-39B depict part of a computer-vision analysis used to determine another aspect of athlete transition time, in accordance with an embodiment of the present technology.
Figure 39B:
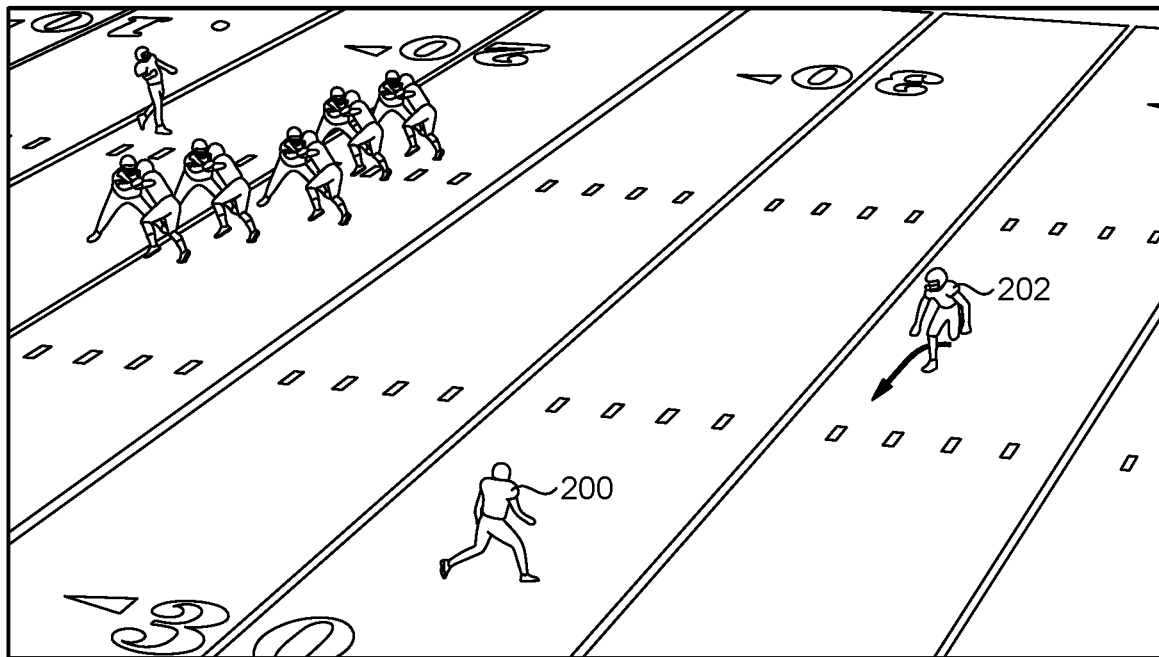
Figure 40A:
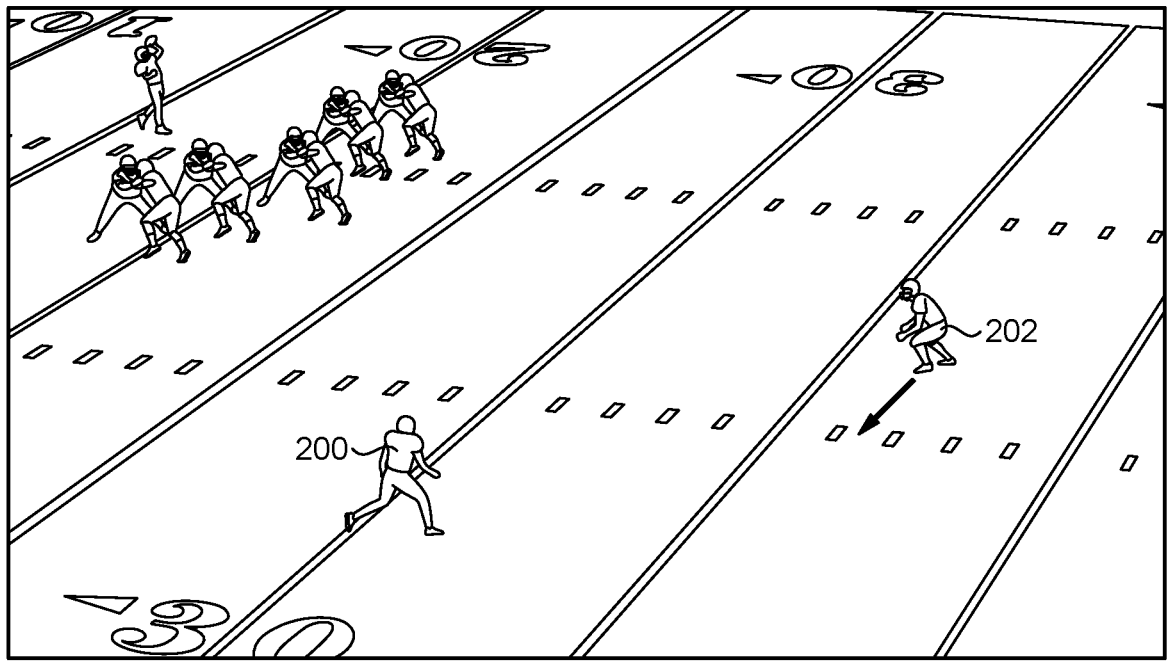
FIGS. 40A-40B depict part of a computer-vision analysis used to determine another aspect of athlete transition time, in accordance with an embodiment of the present technology.
Figure 40B:
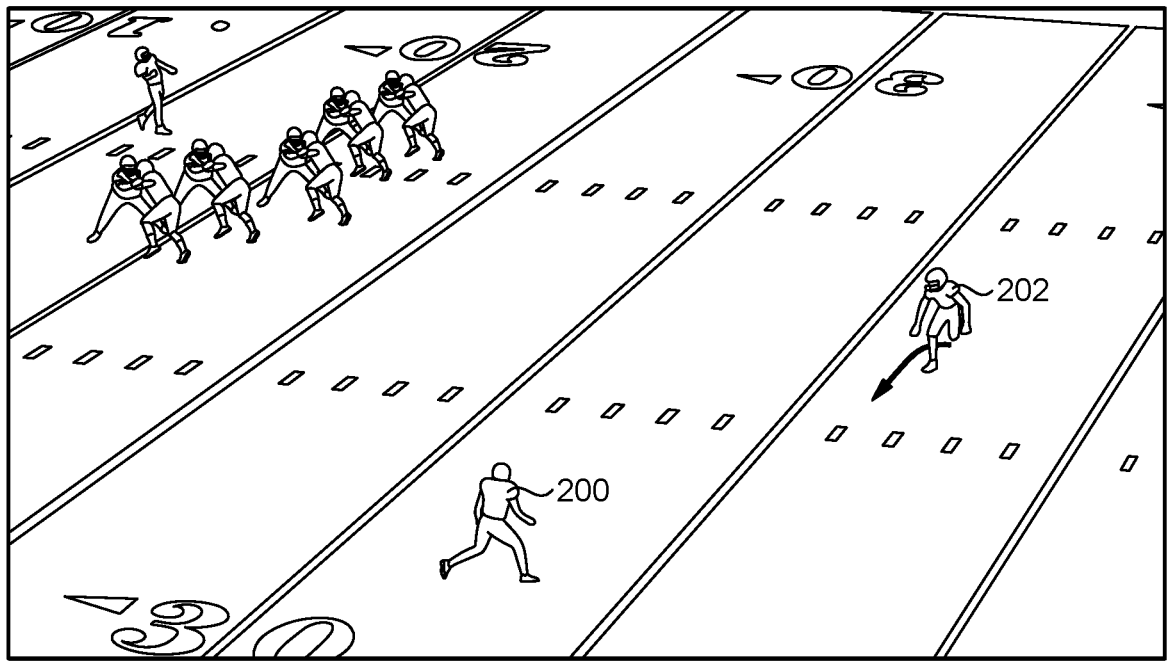

FIGS. 35A-35B depict part of a computer-vision analysis used to determine one form of athlete transition time, in accordance with an embodiment of the present technology. In general, athlete transition time may be determined as the time between an athlete's last step in one direction and the athlete's first step in another direction. FIGS. 35A-35B depict the athletes 200, 202 during gameplay, with the athlete 202 transitioning from backpedaling in a first direction as shown in FIG. 35A, to forward running in a second opposite direction as shown in FIG. 35B. Using the frame-by-frame analysis and distance calculation processes described herein, the time required for the athlete 202 to complete the transition to the new direction of travel may be determined, and may be used to generate performance data for the athlete 202. This may be used for assessment of certain athletes, e.g., defensive athletes. FIGS. 36A-36B, similarly, depict the athletes 200, 202 with the athlete 202 transitioning from backpedaling to forward running, but in addition, with the athlete 202 completing a turn to transition to the new direction. FIGS. 37A-37B, similarly, depict the athletes 200, 202, but instead with the athlete 202 transitioning from sideways running, e.g., shuffling, to forward running without turning. FIGS. 38A-38B, similarly, depict the athletes 200, 202, but with the athlete 202 transitioning from sideways running to forward running with the athlete 202 turning to travel in a new direction. FIGS. 39A-39B, similarly, depict the athletes 200, 202, but with the athlete 202 transitioning from backpedaling to forward running with the athlete 202 completing a partial turn during the transition. FIGS. 40A-40B, similarly, depict the athletes 200, 202, but with the athlete 202 transitioning from sideways running, e.g., shuffling, to forward running with the athlete 202 completing a partial turn during the transition. The transition time determined in each of the aforementioned circumstances may be used to generate athlete performance data, which may be used to assess different types of athletes, e.g., offensive or defensive athletes, depending on the sport and circumstance.

Figure 41A:
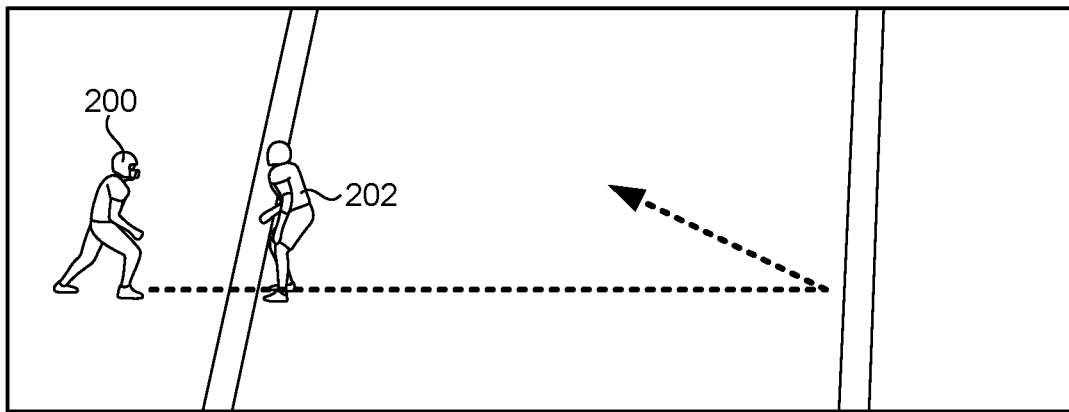
FIGS. 41A-41C depict part of a computer-vision analysis used to determine another aspect of athlete transition time, in accordance with an embodiment of the present technology.
Figure 41B:
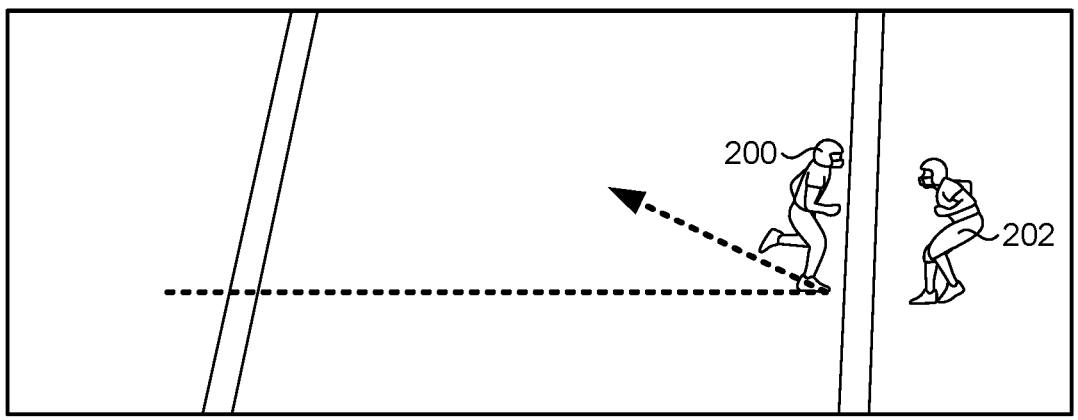
Figure 41C:
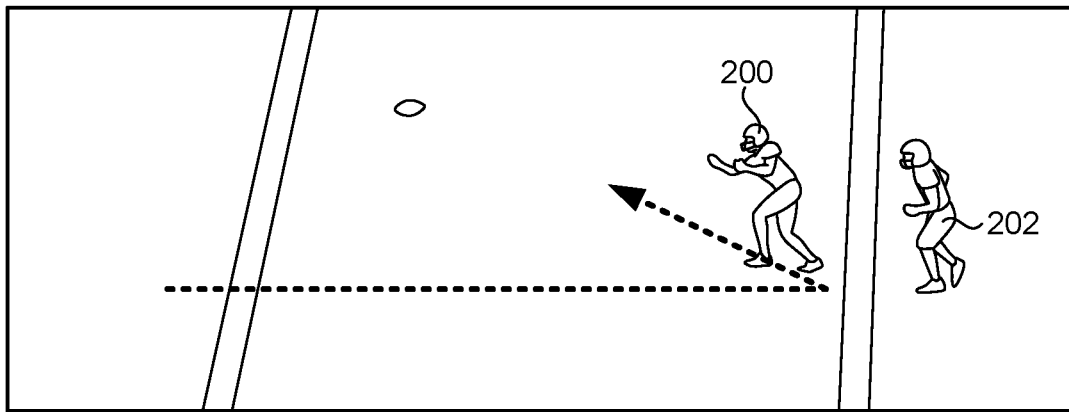

FIGS. 41A-41C depict another part of a computer-vision analysis used to determine athlete transition time, in accordance with an embodiment of the present technology. FIGS. 41A-41C show a frame-by-frame process for identifying the time required for an athlete 200 to transition from the last step in a first direction, e.g., along a first route, as shown in FIG. 41B, to the first step of moving, e.g., sprinting, in a new direction, e.g., along a second route, as shown in FIG. 41C. Through use of the frame-by-frame analysis described herein, the time required for the athlete 200 to complete the transition, with or without turning, may be determined. The transition time may be used to generate athlete performance data, which may be used to assess different types of athletes, e.g., offensive or defensive athletes, depending on the sport and circumstance.

Figure 42A:
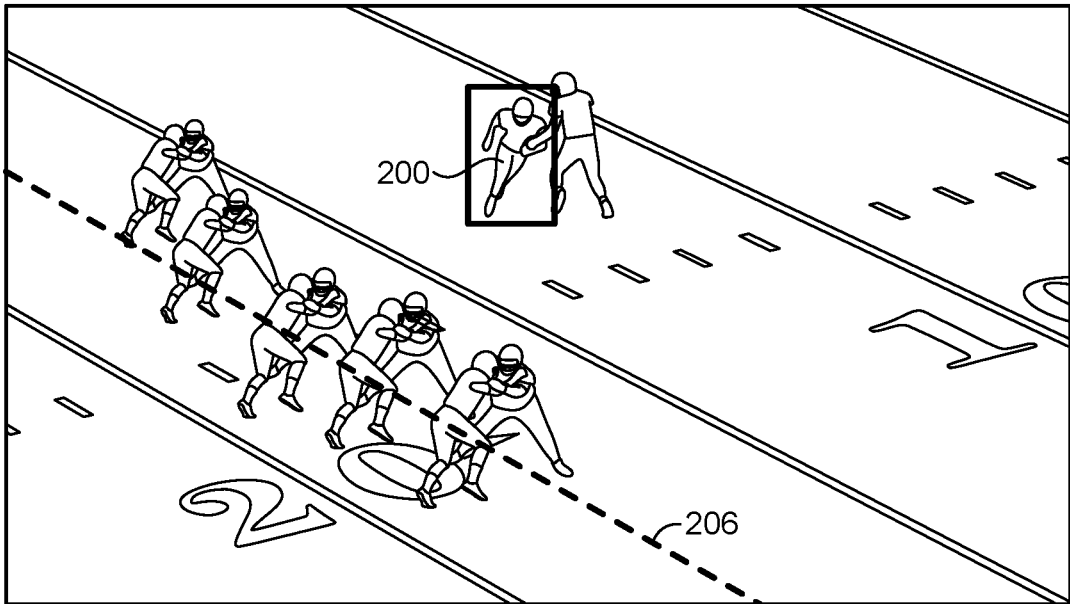
FIGS. 42A-42B depict part of a computer-vision analysis used to determine the time an athlete spends behind a particular demarcation on a playing field, in accordance with an embodiment of the present technology.
Figure 42B:
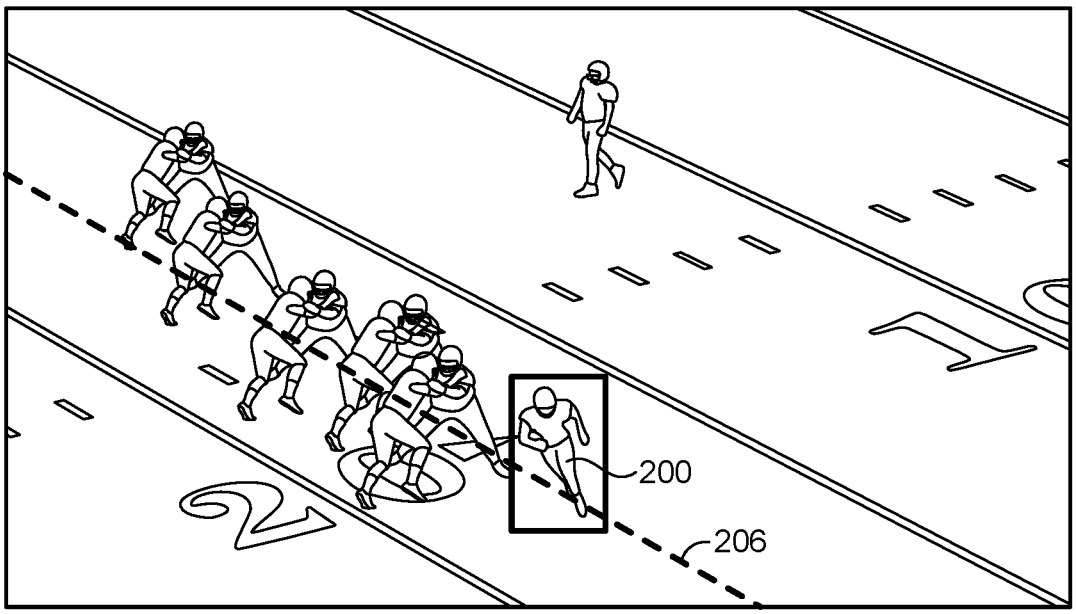

FIGS. 42A-42B depict part of a computer-vision process used to determine the time an athlete spends behind a particular demarcation in a playing field, in accordance with an embodiment of the present technology. In particular, in FIGS. 42A-42B, the athlete 200 is identified, and using frame-by-frame analysis, the position of the athlete 200 in the environment is tracked, allowing the amount of time the athlete 200 spends behind a particular demarcation, e.g., a line of scrimmage 206, to be determined. This information may be used to generate athlete performance data, which may be used to assess different types of athletes, e.g., offensive or defensive athletes, depending on the sport and circumstance.

Figure 43A:
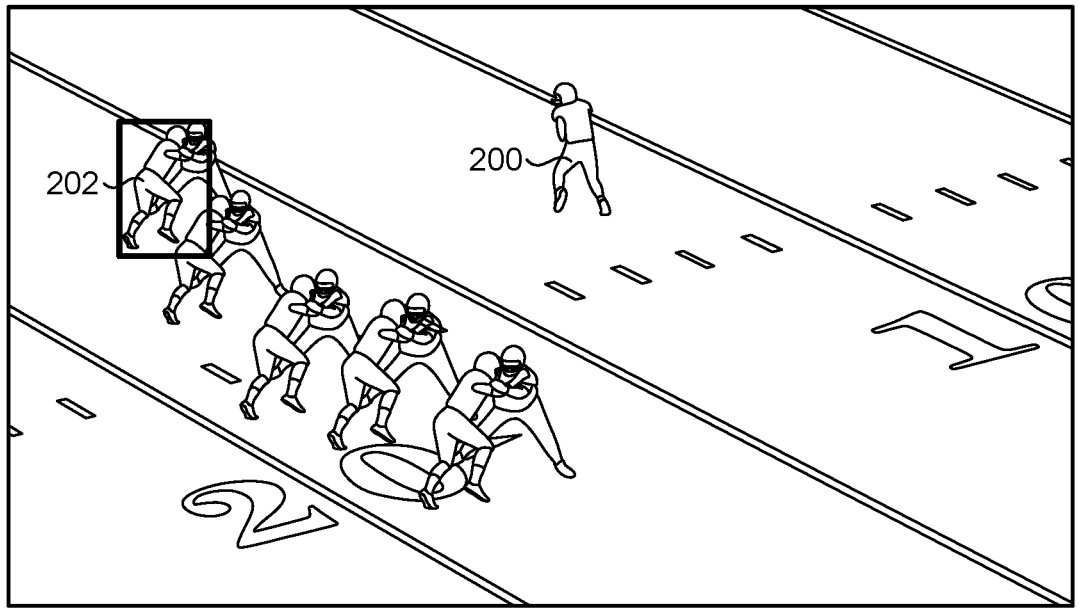
FIGS. 43A-43B depict part of a computer-vision analysis used to determine the time required for an athlete to stop another athlete during gameplay, in accordance with an embodiment of the present technology.
Figure 43B:
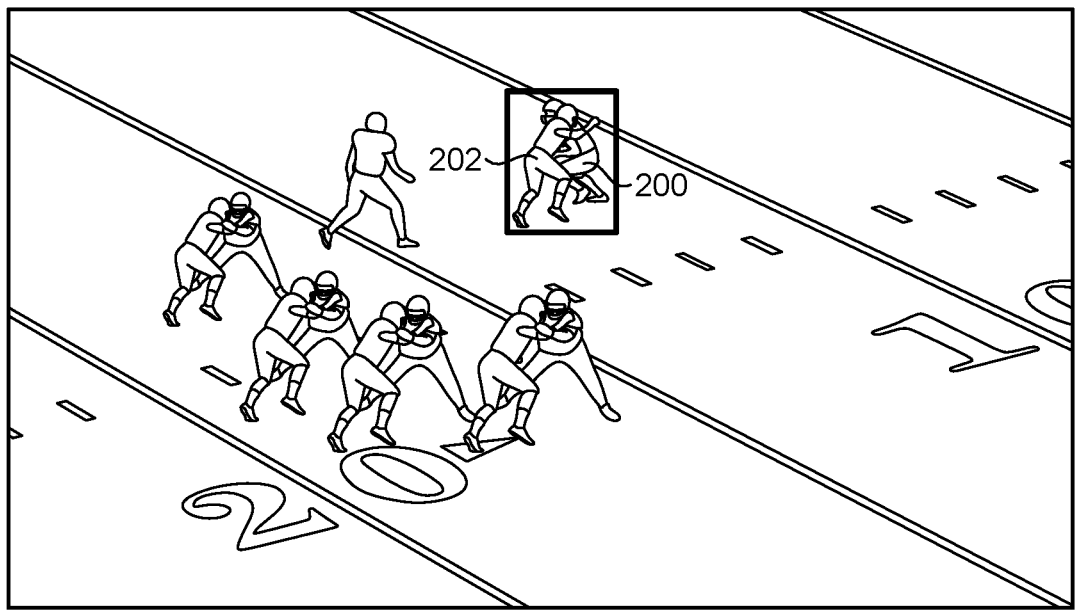

FIGS. 43A-43B depict part of a computer-vision process used to determine the time required for an athlete to reach/stop/tackle another athlete, in accordance with an embodiment of the present technology. FIG. 43B in particular depicts the athletes 200, 202 at a point at which the athlete 202 has reached the athlete 200 to stop a play, e.g., tackle the athlete 200. The athletes 200, 202, while in contact, can be tracked using a frame-by-frame analysis, and then the time required for the athlete 202 to completely stop the athlete 200 can be determined, e.g., based on when the athlete 200 is brought to the ground, or based on another interaction. This information may be used to generate athlete performance data, which may be used to assess different types of athletes, e.g., offensive or defensive athletes, depending on the sport and circumstance.

Figure 44A:
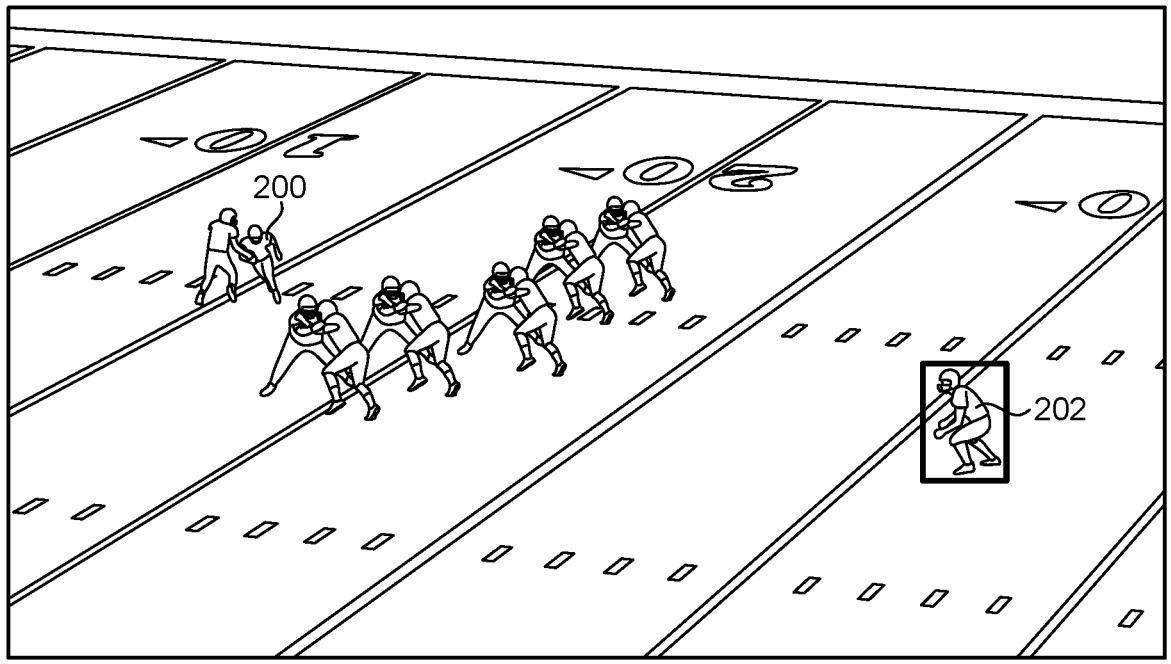
FIGS. 44A-44B depict part of a computer-vision analysis used to determine the time required for an athlete to close the distance to another athlete carrying a game ball, in accordance with an embodiment of the present technology.
Figure 44B:
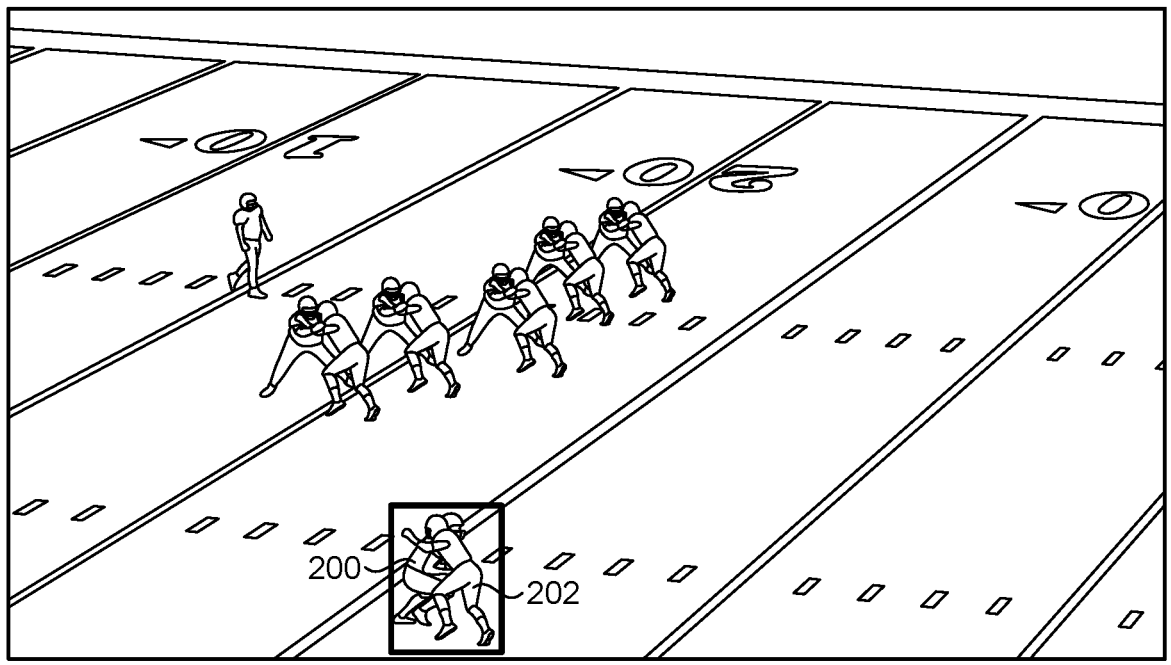

FIGS. 44A-44B depict part of a computer-vision process used to determine the time required for an athlete to close the distance to another athlete carrying a game ball, in accordance with an embodiment of the present technology. FIGS. 44A-44B depict the athletes 200, 202, with the athlete 200 carrying a game ball, and the athlete 202 sprinting to reach the athlete 200. Through use of the frame-by-frame analysis described herein, the time required for the athlete 202 to reach the athlete 200 that is carrying the ball may be determined. This information may be used to generate athlete performance data, which may be used to assess different types of athletes, e.g., offensive or defensive athletes, depending on the sport and circumstance.

Figure 45A:
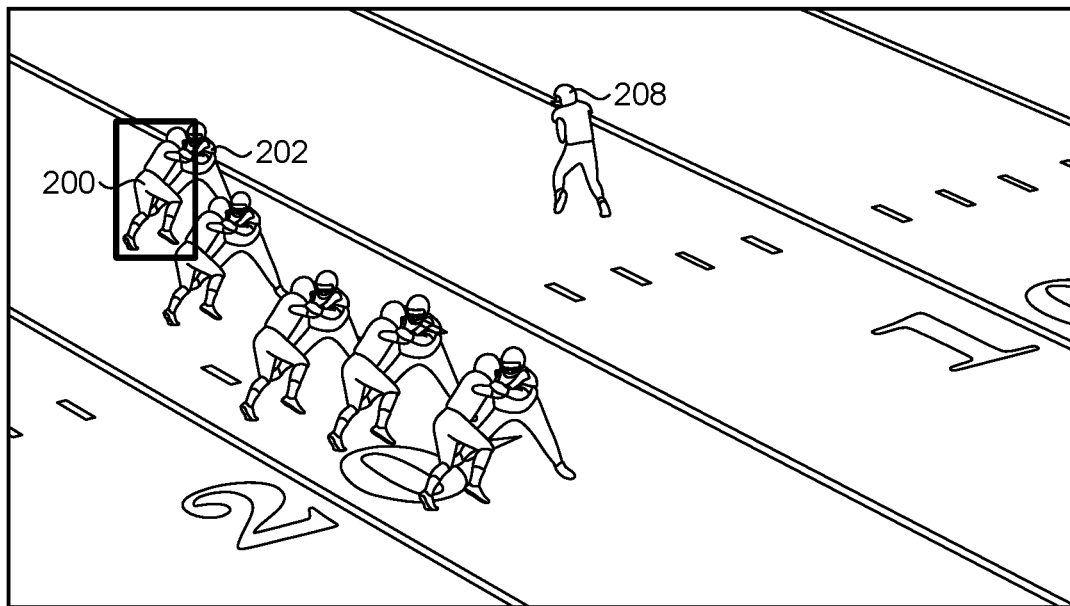
FIGS. 45A-45B depict part of a computer-vision analysis used to determine the time required for an athlete to stop another athlete during gameplay, in accordance with an embodiment of the present technology.
Figure 45B:
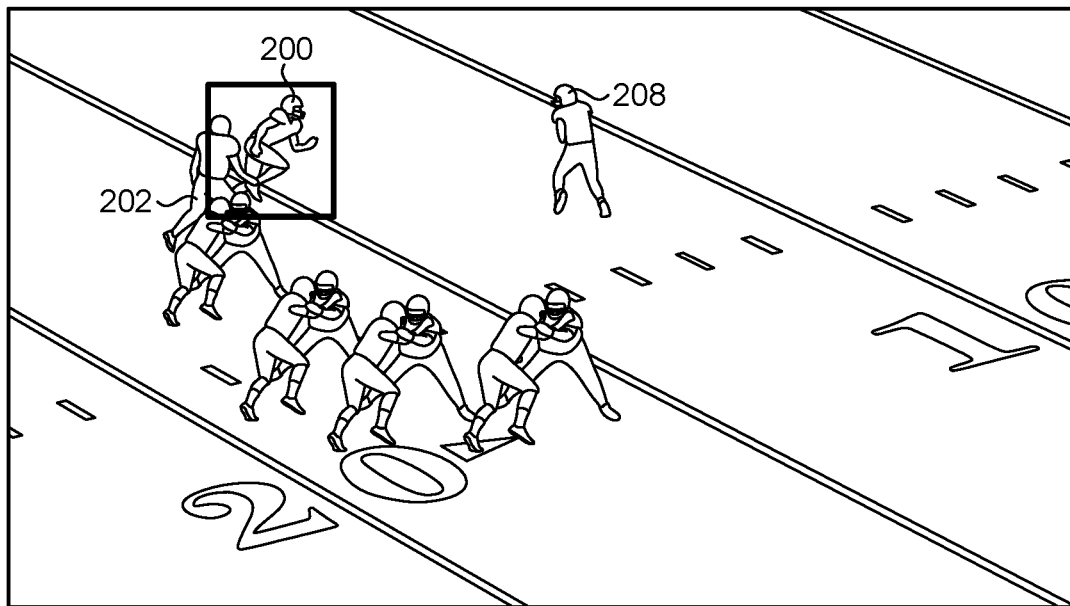

FIGS. 45A-45B depict another part of a computer-vision process used to determine the time required for an athlete to close the distance to another athlete trying to pass a game ball, in accordance with an embodiment of the present technology. FIGS. 45A-45B depict the athletes 200, 202, with the athlete 200 attempting to stop an athlete 208 from throwing a game ball, and the athlete 202 blocking. Through use of the frame-by-frame analysis described herein, the time required for the athlete 200 to reach the athlete 208 that is carrying the ball, and/or sack the athlete 208, may be determined. This information may be used to generate athlete performance data, which may be used to assess different types of athletes, e.g., offensive or defensive athletes, depending on the sport and circumstance.

In addition to tracking the location, speed, and direction of athletes in video, a game implement may also be tracked in video, using the processes described herein. The data generated from this tracking process may also be used to generate performance data for an associated athlete and may be used to update an athlete profile. For example, when the tracked game implement is a game ball, the speed, acceleration, trajectory, and/or distance the game ball travels may be determined using the processes described herein. To provide a further example specific to football, the time from when a football is acquired by a quarterback, to the time when the football is thrown by the quarterback, may be tracked and used to generate performance data for the quarterback. In another circumstance, a speed, trajectory, and distance a ball travels, e.g., when it is thrown or hit, may be tracked using the tracking processes described herein. In another aspect, when the game implement is a game object, such as a golf club, baseball bat, hockey stick, tennis racket, or the like, associated with the athlete, the game object may also be tracked, thereby allowing a speed, acceleration, and/or movement of the game object to be determined, allowing additional performance data to be generated for the associated athlete.

Clause 1. A computer-implemented method for generating athlete performance data using computer-vision analysis, the method comprising accessing a video, the video comprising a plurality of frames depicting an athlete, each of the plurality of frames having an associated time-stamp; identifying, using a computer-vision system, a location of the athlete in each frame of the plurality of frames; identifying, using the computer-vision system, a location of a reference element in each frame of the plurality of frames; identifying, using the computer-vision system, a number of pixels between the athlete and the reference element in each frame of the plurality of frames to thereby determine a pixel-distance between the athlete and the reference element in each frame; converting, using the computer-vision system, each pixel-distance to a corresponding physical distance using a conversion process; generating performance data for the athlete using the converted physical distance at each time-stamp; and updating a profile associated with the athlete to include the generated performance data.

Clause 2. The computer-implemented method of clause 1, wherein the reference element is a fixed object in an environment.

Clause 3. The computer-implemented method of any of clauses 1-2, wherein the performance data is a maximum speed achieved by the athlete over a period of time.

Clause 4. The computer-implemented method of any of clauses 1-3, wherein the performance data is a maximum acceleration achieved by the athlete over a period of time.

Clause 5. The computer-implemented method of any of clauses 1-4, wherein the performance data comprises a transition time for the athlete over a period of time.

Clause 6. The computer-implemented method of any of clauses 1-5, wherein the reference element comprises one of a solid line, a dashed line, or a geometric shape.

Clause 7. The computer-implemented method of any of clauses 1-6, wherein the athlete is a first athlete, wherein the plurality of frames further depict a second athlete, and wherein the reference element is the second athlete.

Clause 8. The computer-implemented method of any of clauses 1-7, wherein the performance data comprises an average physical separation between the first athlete and the second athlete.

Clause 9. The computer-implemented method of any of clauses 1-8, wherein the performance data comprises a closing speed of the first athlete relative to the second athlete over a period of time.

Clause 10. The computer-implemented method of any of clauses 1-9, wherein the conversion process uses at least one of a calibration factor and a transformation matrix.

Clause 11. One or more computer-readable media having computer-executable instructions stored thereon that, when executed by one or more computer processors, perform a method for generating athlete performance data through computer-vision analysis, the method comprising accessing a video, the video comprising a plurality of frames depicting an athlete, each of the plurality of frames having an associated time-stamp; identifying, using a computer-vision system, a location of the athlete in each frame of the plurality of frames; identifying, using the computer-vision system, a location of a reference element in each frame of the plurality of frames; identifying, using the computer-vision system, a number of pixels between the athlete and the reference element in each frame of the plurality of frames to thereby determine a pixel-distance between the athlete and the reference element in each frame; converting, using the computer-vision system, each pixel-distance to a corresponding physical distance using a conversion process; generating performance data for the athlete using the converted physical distance at each time-stamp; and updating a profile associated with the athlete to include the generated performance data.

Clause 12. The one or more computer-readable media of clause 11, wherein the reference element is a fixed object in an environment.

Clause 13. The one or more computer-readable media of any of clauses 11-12, wherein the performance data is a maximum speed achieved by the athlete over a period of time.

Clause 14. The one or more computer-readable media of any of clauses 11-13, wherein the performance data of the athlete is a maximum acceleration achieved by the athlete over a period of time.

Clause 15. The one or more computer-readable media of any of clauses 11-14, wherein the performance data comprises a transition time for the athlete over a period of time.

Clause 16. The one or more computer-readable media of any of clauses 11-15, wherein the athlete is a first athlete, wherein the plurality of frames further depict a second athlete, and the wherein the reference element is the second athlete.

Clause 17. The one or more computer-readable media of any of clauses 11-16, wherein the performance data comprises a physical separation between the first athlete and the second athlete at a particular time-stamp.

Clause 18. The one or more computer-readable media of any of clauses 11-17, wherein the performance data comprises a closing speed of the first athlete relative to the second athlete over a period of time.

Clause 19. The one or more computer-readable media of any of clauses 11-18, wherein the conversion process uses at least one of a calibration factor and a transformation matrix.

Clause 20. A computer system configured for generating athlete performance data using computer-vision analysis, the system comprising at least one processor; and one or more computer-readable media having computer-executable instructions stored thereon that, when executed by the at least one processor, perform a method comprising accessing a video, the video comprising a plurality of frames depicting an athlete, each of the plurality of frames having an associated time-stamp; identifying, using a computer-vision system, a location of the athlete in each frame of the plurality of frames; identifying, using the computer-vision system, a location of a reference element in each frame of the plurality of frames; identifying, using the computer-vision system, a number of pixels between the athlete and the reference element in each frame of the plurality of frames to thereby determine a pixel-distance between the athlete and the reference element in each frame; converting, using the computer-vision system, each pixel-distance to a corresponding physical distance; generating performance data for the athlete using the converted physical distance at each time-stamp; and updating a profile associated with the athlete to include the generated performance data.

Clause 21. A computer-implemented method for generating athlete performance data in automated or semi-automated fashion using an athlete assessment system, the method comprising accessing, by the athlete assessment system, a video, the video comprising a plurality of frames depicting an athlete; automatically identifying, by the athlete assessment system, a location of the athlete in each frame of the plurality of frames; automatically identifying, by the athlete assessment system, a location of a reference element in each frame of the plurality of frames; automatically identifying, by the athlete assessment system, a number of pixels between the athlete and the reference element in each frame of the plurality of frames to thereby determine a pixel-distance between the athlete and the reference element in each frame; automatically converting, by the athlete assessment system, each pixel-distance to a corresponding physical distance, e.g., using a calibration factor and/or a perspective transformation matrix; automatically generating, by the athlete assessment system, performance data for the athlete utilizing at least the converted physical distance in each frame; automatically updating, by the athlete assessment system, a profile associated with the athlete to include the generated performance data; and enabling identification of the athlete based on the generated performance data associated with the profile of the athlete.

Clause 22. An athlete assessment system used for generating athlete performance data in automated or semi-automated fashion, the system comprising at least one computer processor; at least one computer memory; and one or more computer-readable media having computer executable instructions stored thereon that, when executed by the at least one processor, perform a method comprising accessing, by the athlete assessment system, a video, the video comprising a plurality of frames depicting an athlete; automatically identifying, by the athlete assessment system, a location of the athlete in each frame of the plurality of frames; automatically identifying, by the athlete assessment system, a location of a reference element in each frame of the plurality of frames; automatically identifying, by the athlete assessment system, a number of pixels between the athlete and the reference element in each frame of the plurality of frames to thereby determine a pixel-distance between the athlete and the reference element in each frame; automatically converting, by the athlete assessment system, each pixel-distance to a corresponding physical distance, e.g., using a calibration factor and/or a perspective transformation matrix; automatically generating, by the athlete assessment system, performance data for the athlete utilizing at least the converted physical distance in each frame; automatically updating, by the athlete assessment system, a profile associated with the athlete to include the generated performance data; and enabling identification of the athlete based on the generated performance data associated with the profile of the athlete.

Clause 23. Any of the preceding clauses in any combination.

In some embodiments, this disclosure may include the language, for example, "at least one of [element A] and [element B]." This language may refer to one or more of the elements. For example, "at least one of A and B" may refer to "A," "B," or "A and B." In other words, "at least one of A and B" may refer to "at least one of A and at least one of B," or "at least either of A or B." In some embodiments, this disclosure may include the language, for example, "[element A], [element B], and/or [element C]." This language may refer to either of the elements or any combination thereof. In other words, "A, B, and/or C" may refer to "A," "B," "C," "A and B," "A and C," "B and C," or "A, B, and C."

The subject matter of this disclosure has been described in relation to particular embodiments, which are intended in all respects to be illustrative rather than restrictive. Alternative embodiments will become apparent to those of ordinary skill in the art to which the present subject matter pertains without departing from the scope hereof. Different combinations of elements, as well as use of elements not shown, are also possible and contemplated.

What is claimed is:

1. A computer-implemented method for generating athlete performance data using computer-vision analysis and identifying athletes with desired characteristics, the method comprising:
   accessing a video, the video comprising a plurality of frames depicting an athlete, each of the plurality of frames having an associated time-stamp;
   identifying, using a computer-vision system, a location of the athlete in each frame of the plurality of frames;
   identifying, using the computer-vision system, a location of a reference element in each frame of the plurality of frames;
   identifying, using the computer-vision system, a number of pixels between the athlete and the reference element in each frame of the plurality of frames to thereby determine a pixel-distance between the athlete and the reference element in each frame;
   converting, using the computer-vision system, each pixel-distance to a corresponding physical distance;
   generating performance data for the athlete using the converted physical distance at each time-stamp;
   updating an athlete profile associated with the athlete to include the generated performance data;
   receiving one or more inputs comprising athlete data;
   updating the athlete profile associated with the athlete to include the athlete data;
   receiving a plurality of user-selected parameters associated with at least one desired characteristic;
   selecting the athlete profile from a plurality of athlete profiles based on a comparison of the user-selected parameters and the athlete profile including the athlete data thereof and the generated performance data thereof; and
   identifying the athlete profile as a best-fit match with the user-selected parameters.

2. The computer-implemented method of claim 1, wherein the reference element is a fixed object in an environment.

3. The computer-implemented method of claim 2, wherein the performance data is a maximum speed achieved by the athlete over a period of time.

4. The computer-implemented method of claim 2, wherein the performance data is a maximum acceleration achieved by the athlete over a period of time.

5. The computer-implemented method of claim 2, wherein the performance data comprises a transition time for the athlete over a period of time.

6. The computer-implemented method of claim 1, wherein the reference element comprises one of:
   a solid line,
   a dashed line, or
   a geometric shape.

7. The computer-implemented method of claim 1, wherein the athlete is a first athlete, wherein the plurality of frames further depict a second athlete, and wherein the reference element is the second athlete.

8. The computer-implemented method of claim 7, wherein the performance data comprises an average physical separation between the first athlete and the second athlete.

9. The computer-implemented method of claim 7, wherein the performance data is a closing speed of the first athlete relative to the second athlete over a period of time.

10. The computer-implemented method of claim 1, wherein the athlete data comprises one or more test scores of the athlete.

11. The computer-implemented method of claim 1, wherein the athlete data comprises a grade point average ("GPA") for the athlete.

12. The computer-implemented method of claim 1, wherein the athlete data comprises a location of the athlete.

13. The computer-implemented method of claim 1, wherein the athlete data comprises a sport and a position played by the athlete.

14. The computer-implemented method of claim 1, wherein the athlete data comprises a number of visits to recruiting organizations.

15. The computer-implemented method of claim 1, wherein the athlete data comprises one or more offers to join a school, team, or organization.

16. The computer-implemented method of claim 1, wherein the athlete data comprises a number of followers on social media.

17. The computer-implemented method of claim 1, wherein the best-fit match comprises a plurality of percentage matches each associated with one of the plurality of user-selected parameters.

18. A computer system configured for generating athlete performance data using computer-vision analysis and identifying athletes with desired characteristics, the system comprising:
at least one processor; and
one or more computer-readable media having computer-executable instructions stored thereon that, when executed by the at least one processor, perform a method comprising:
accessing a video, the video comprising a plurality of frames depicting an athlete, each of the plurality of frames having an associated time-stamp;
identifying, using a computer-vision system, a location of the athlete in each frame of the plurality of frames;
identifying, using the computer-vision system, a location of a reference element in each frame of the plurality of frames;
identifying, using the computer-vision system, a number of pixels between the athlete and the reference element in each frame of the plurality of frames to thereby determine a pixel-distance between the athlete and the reference element in each frame;
converting, using the computer-vision system, each pixel-distance to a corresponding physical distance;
generating performance data for the athlete using the converted physical distance at each time-stamp;
updating an athlete profile associated with the athlete to include the generated performance data;
receiving one or more inputs comprising athlete data;
updating the athlete profile associated with the athlete to include the athlete data;
receiving a plurality of user-selected parameters associated with at least one desired characteristic;
selecting the athlete profile from a plurality of athlete profiles based on a comparison of the user-selected parameters and the athlete profile including the athlete data thereof and the generated performance data thereof; and
identifying the athlete profile as a best-fit match with the user-selected parameters.

19. A computer-implemented method for generating athlete performance data using computer-vision analysis and identifying athletes with desired characteristics, the method comprising:
accessing a video, the video comprising a plurality of frames depicting an athlete during gameplay, each of the plurality of frames having an associated time-stamp;
identifying, using a computer-vision system, a location of the athlete in each frame of the plurality of frames;
identifying, using the computer-vision system, a location of a reference element in each frame of the plurality of frames;
identifying, using the computer-vision system, a number of pixels between the athlete and the reference element in each frame of the plurality of frames to thereby determine a pixel-distance between the athlete and the reference element in each frame;
converting, using the computer-vision system, each pixel-distance to a corresponding physical distance;
generating performance data for the athlete using the converted physical distance at each time-stamp, wherein the generated performance data comprises a plurality of athlete metrics;
generating an athleticism score for the athlete, wherein the athleticism score comprises a weighted combination of the plurality of athlete metrics associated with the performance data, and wherein the athleticism score is associated with a particular sport position;
updating an athlete profile associated with the athlete to include the athleticism score;
receiving a plurality of user-selected parameters for at least one desired characteristic; and
identifying the athlete profile based at least in part on the athleticism score.

20. The computer-implemented method of claim 19, wherein the plurality of athlete metrics included in the weighted combination comprise:
maximum speed,
time to maximum speed,
maximum acceleration,
closing speed,
transition time, and
average separation distance between the athlete and another athlete.

* * * * *